US009271780B2

(12) United States Patent
Noon et al.

(10) Patent No.: US 9,271,780 B2
(45) Date of Patent: Mar. 1, 2016

(54) DISTRACTOR WITH REMOVABLE FOOTPLATES

(71) Applicant: DePuy Synthes Products, Inc., Raynham, MA (US)

(72) Inventors: John M. Noon, West Chester, PA (US); Ryan Sellman, West Chester, PA (US); Timothy M. Sellers, San Jose, CA (US); Matthew Shanaman, Baltimore, MD (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/485,134

(22) Filed: Sep. 12, 2014

(65) Prior Publication Data

US 2014/0378983 A1 Dec. 25, 2014

Related U.S. Application Data

(62) Division of application No. 12/890,026, filed on Sep. 24, 2010, now Pat. No. 8,858,566.

(60) Provisional application No. 61/245,561, filed on Sep. 24, 2009.

(51) Int. Cl.
    *A61B 17/58* (2006.01)
    *A61B 17/60* (2006.01)
    *A61F 2/00* (2006.01)
    *A61B 17/88* (2006.01)
    *A61B 17/66* (2006.01)
    *A61B 17/80* (2006.01)

(52) U.S. Cl.
    CPC ............ *A61B 17/885* (2013.01); *A61B 17/663* (2013.01); *A61B 17/8004* (2013.01); *A61B 17/8071* (2013.01)

(58) Field of Classification Search
    USPC .............................................. 606/57, 90, 105
    See application file for complete search history.

(56) References Cited

U.S. PATENT DOCUMENTS 5,885,290 A  3/1999  Guerrero et al.
6,036,690 A  3/2000  De La Plaza Fernandez
(Continued)

FOREIGN PATENT DOCUMENTS

CN  2354513 Y  12/1999
DE  20012536    1/2001
(Continued)

OTHER PUBLICATIONS

Notification of the First Office Action dated Apr. 10, 2014; Chinese Patent Application 201080051035.8.

*Primary Examiner* — Sameh Boles
(74) *Attorney, Agent, or Firm* — Baker & Hostetler LLP

(57) ABSTRACT

A bone distractor assembly configured to distract first and second bone segments on opposite sides of a bone gap is provided. In one embodiment the distractor assembly includes a distractor having a first coupler and a second coupler, a first footplate releasably coupled to the first coupler, a second footplate releasably coupled to the second coupler, and a locking mechanism releasably coupling the first and second footplates to the first and second couplers. The first and second footplates releasably are each configured to attach to bone. The locking mechanism includes a tube, wherein removal of the tube releases the first and second footplates from the first and second couplers.

14 Claims, 52 Drawing Sheets

(56) References Cited

U.S. PATENT DOCUMENTS

| | | |
|---|---|---|
| 6,113,599 A | 9/2000 | Landsberger |
| 6,277,124 B1 * | 8/2001 | Haag .................. 606/105 |
| 6,293,947 B1 | 9/2001 | Buchbinder |
| 6,423,069 B1 | 7/2002 | Sellers |
| 6,471,706 B1 | 10/2002 | Schumacher et al. |
| 6,565,576 B1 | 5/2003 | Stauch et al. |
| 6,786,910 B2 | 9/2004 | Cohen et al. |
| 6,972,020 B1 | 12/2005 | Grayson et al. |
| 2002/0035368 A1 | 3/2002 | Schumacher |
| 2002/0040225 A1 | 4/2002 | Sellers et al. |
| 2002/0072747 A1 | 6/2002 | Cohen et al. |
| 2002/0116002 A1 | 8/2002 | Sellers |
| 2003/0233093 A1 | 12/2003 | Moles et al. |
| 2005/0119659 A1 | 6/2005 | Pfefferle et al. |
| 2005/0256526 A1 | 11/2005 | Johnston |
| 2006/0015118 A1 | 1/2006 | Richter et al. |
| 2006/0079902 A1 | 4/2006 | Johnston |
| 2007/0043370 A1 | 2/2007 | Ueda et al. |
| 2007/0162045 A1 | 7/2007 | Ahmad |
| 2011/0125162 A1 | 5/2011 | Noon et al. |

FOREIGN PATENT DOCUMENTS

| | | |
|---|---|---|
| JP | 2002-538931 | 11/2002 |
| WO | WO 01/30249 | 5/2001 |
| WO | WO 2011/038209 | 5/2011 |

* cited by examiner

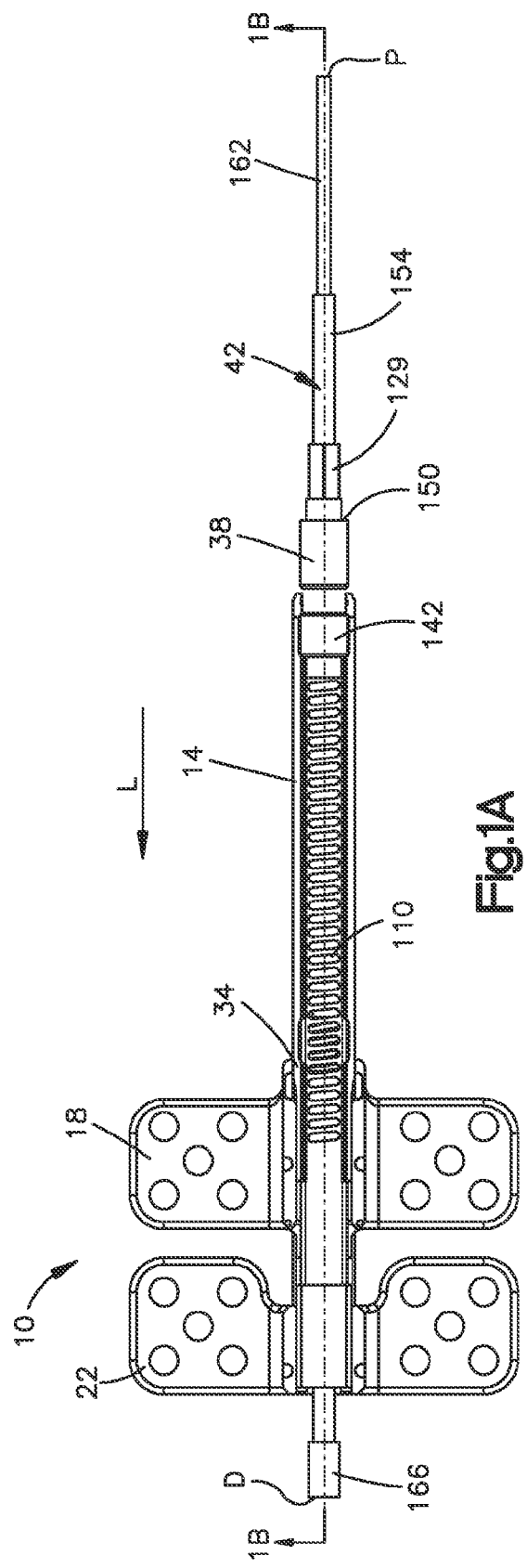
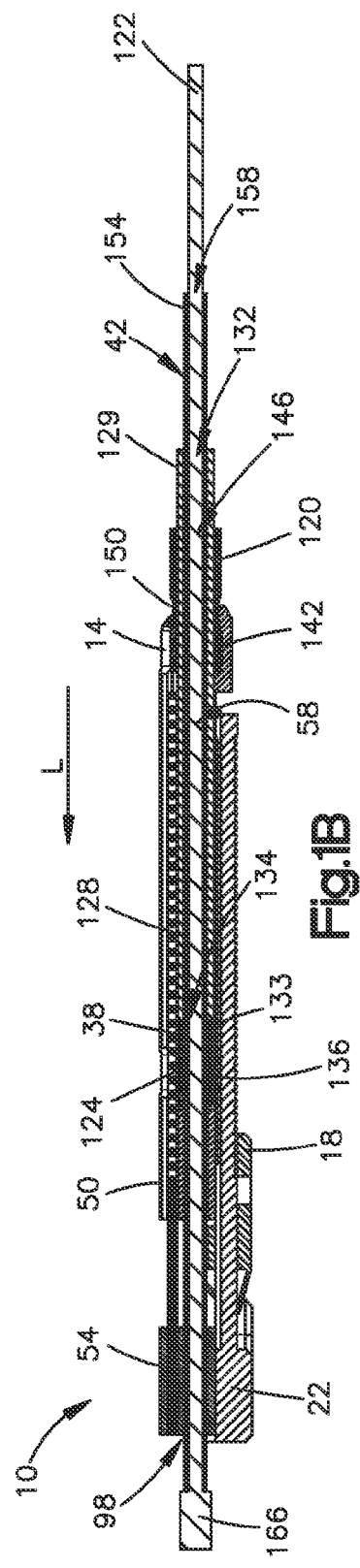

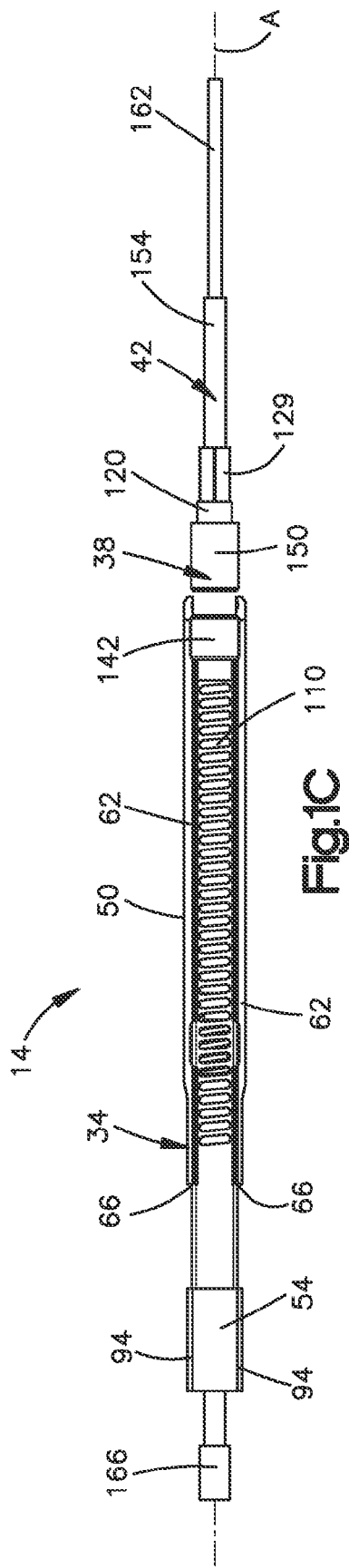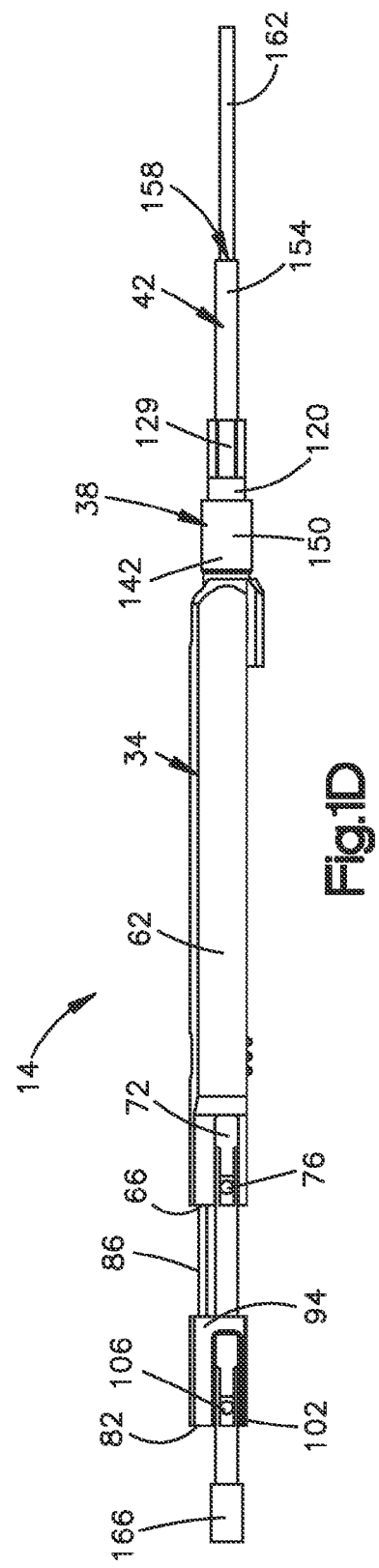

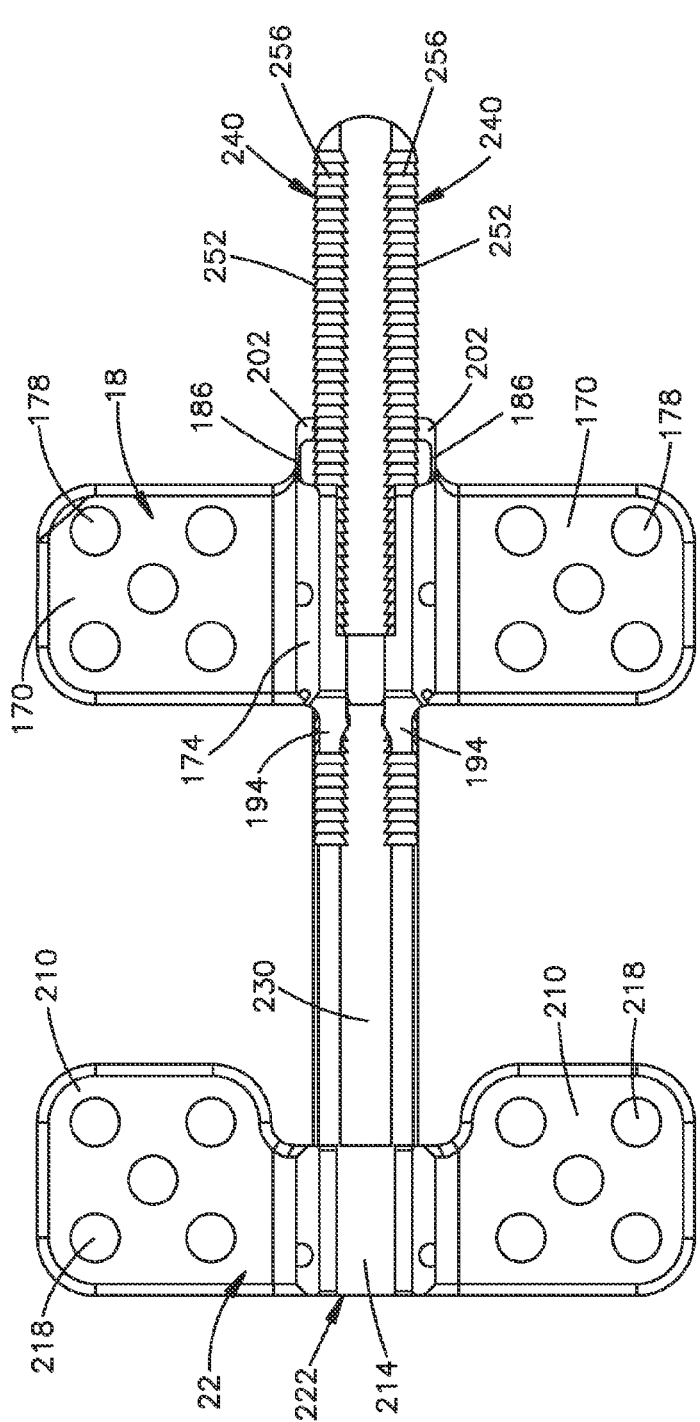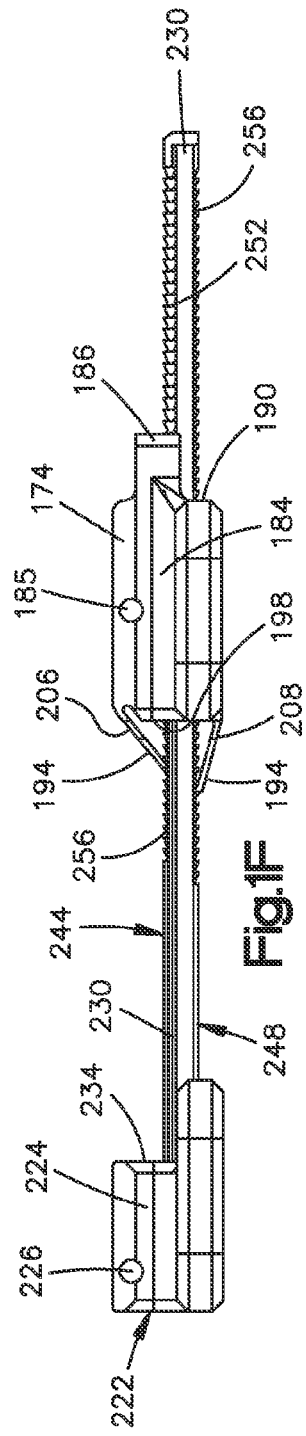

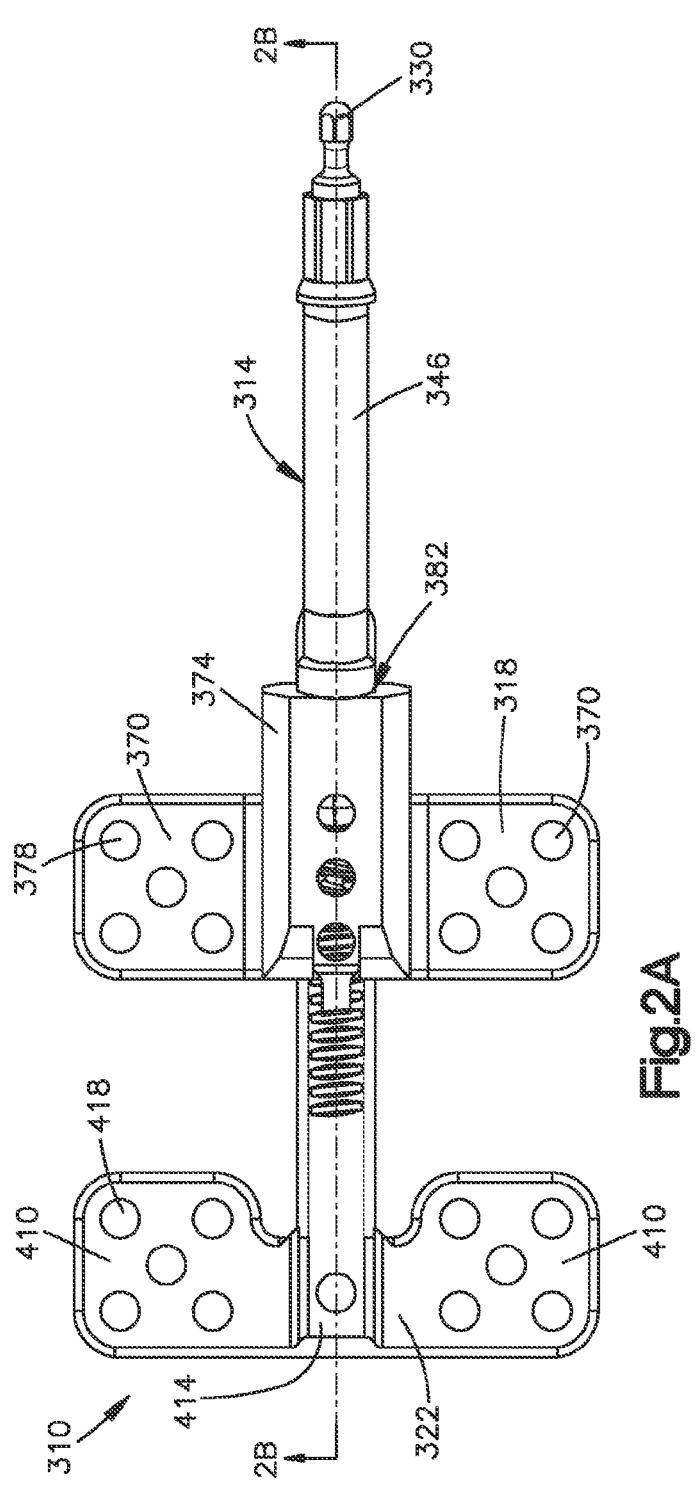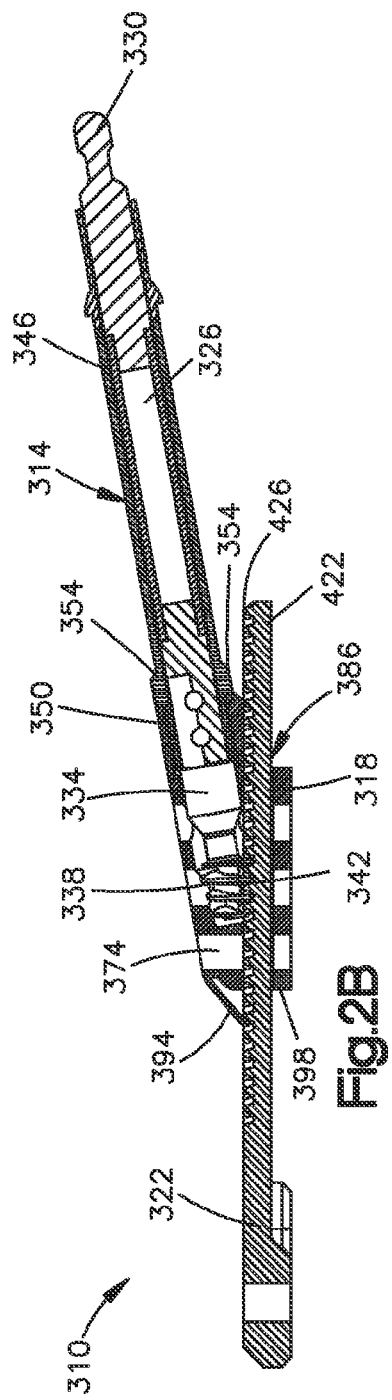

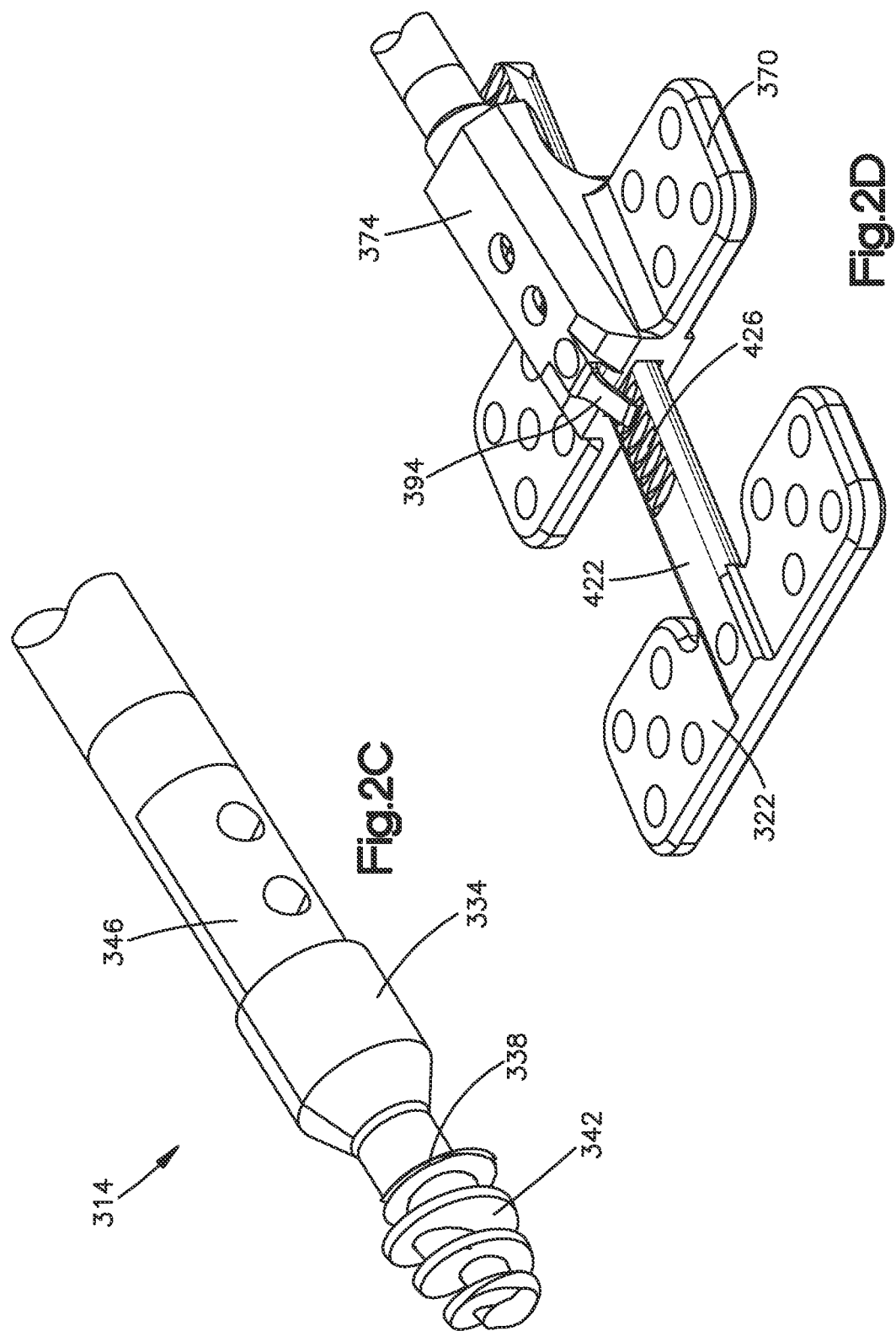

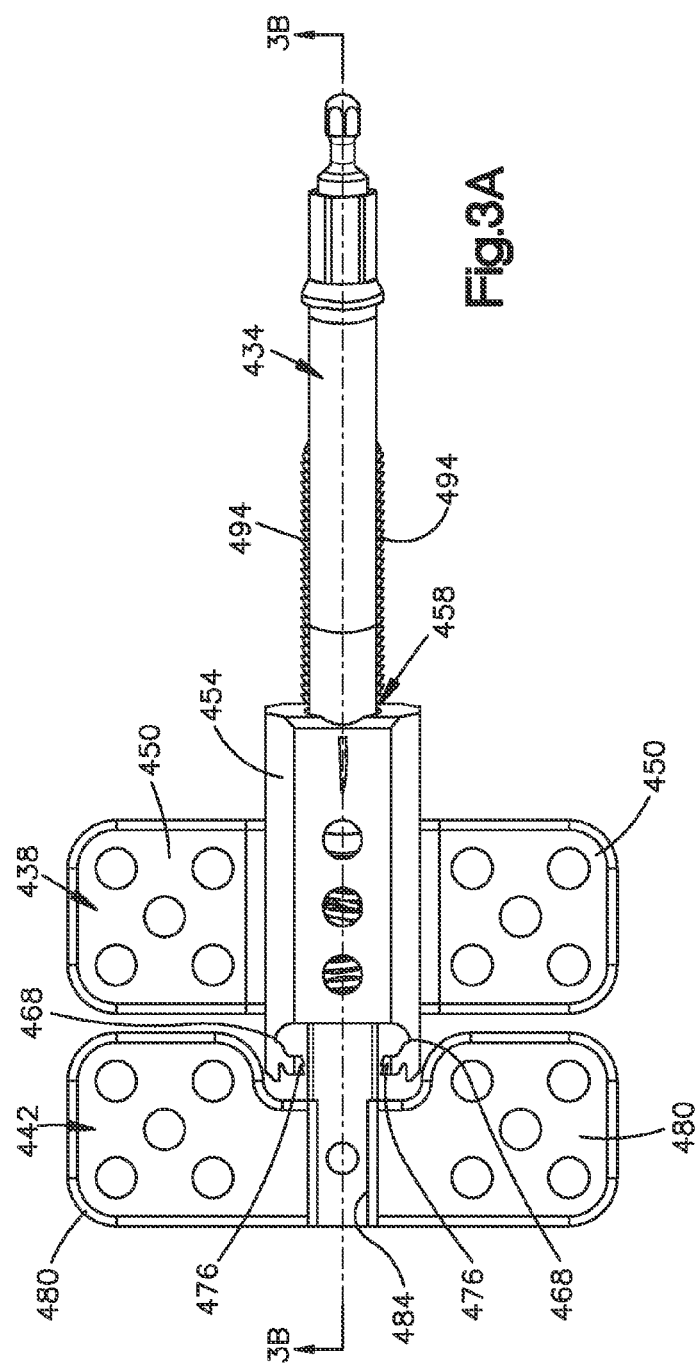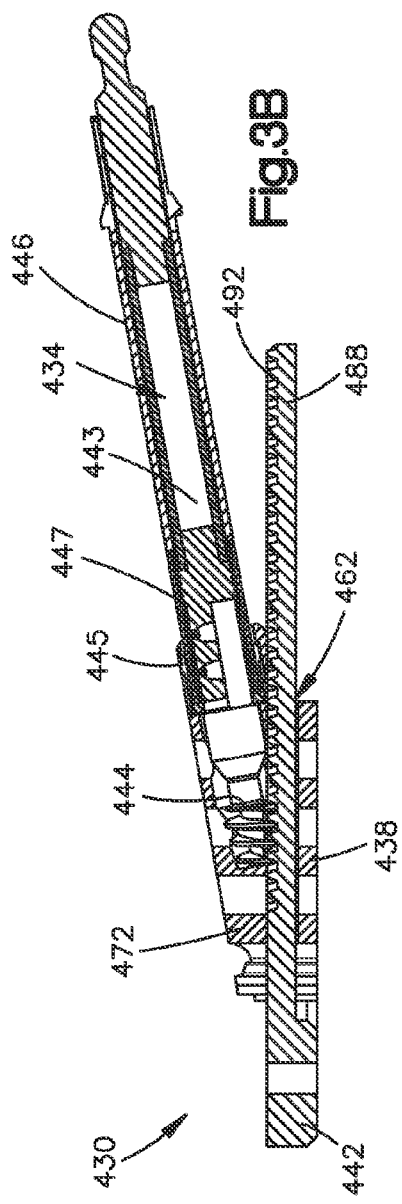

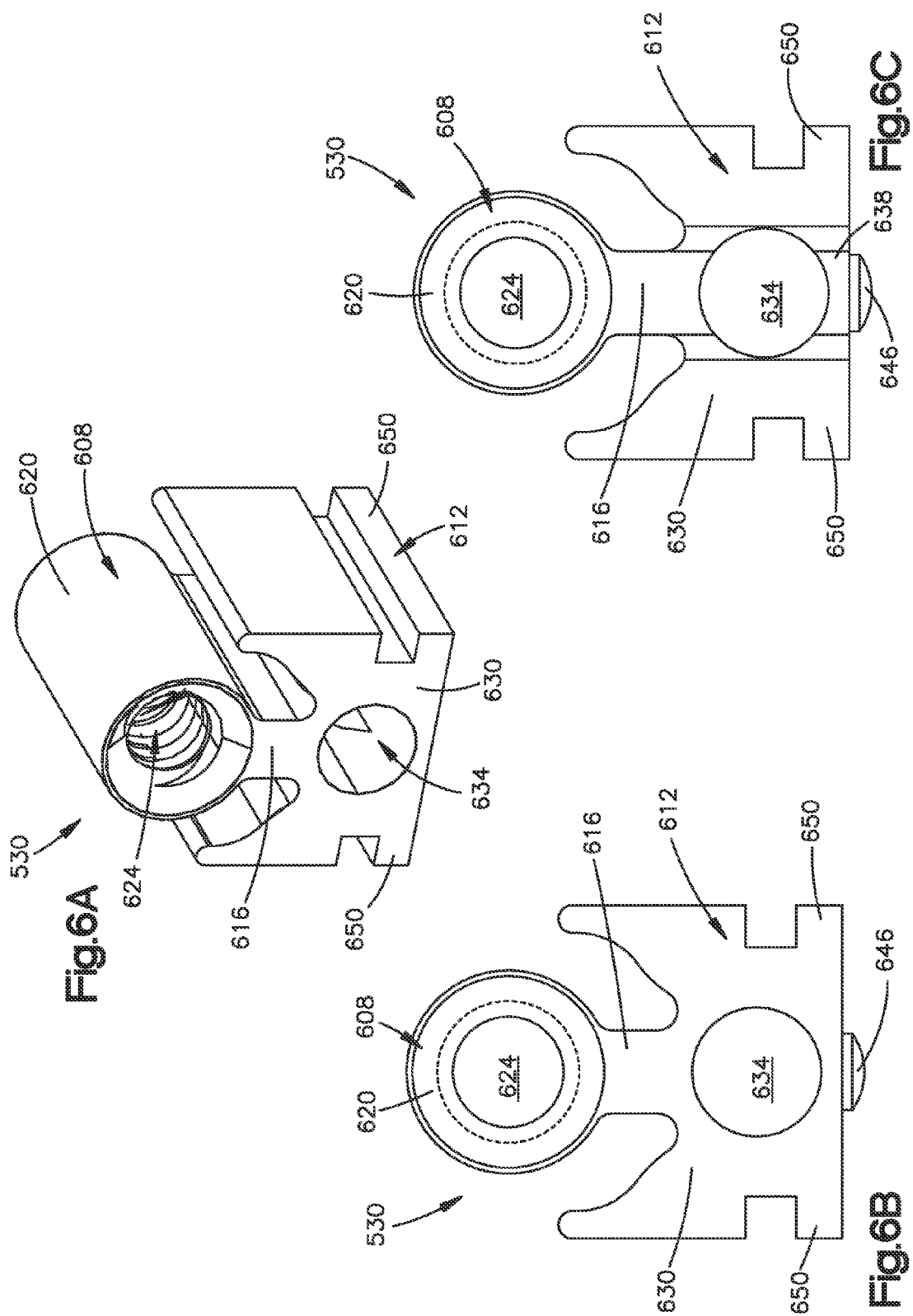

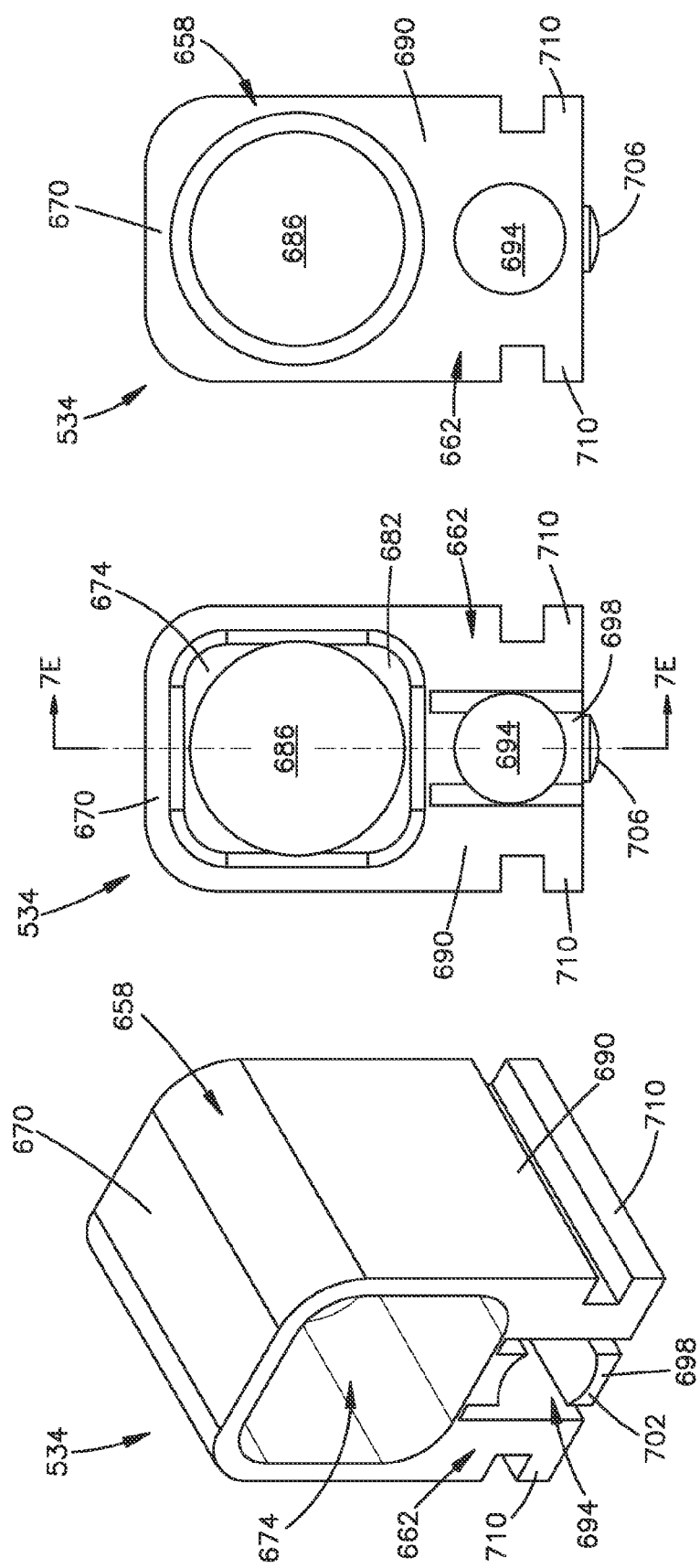

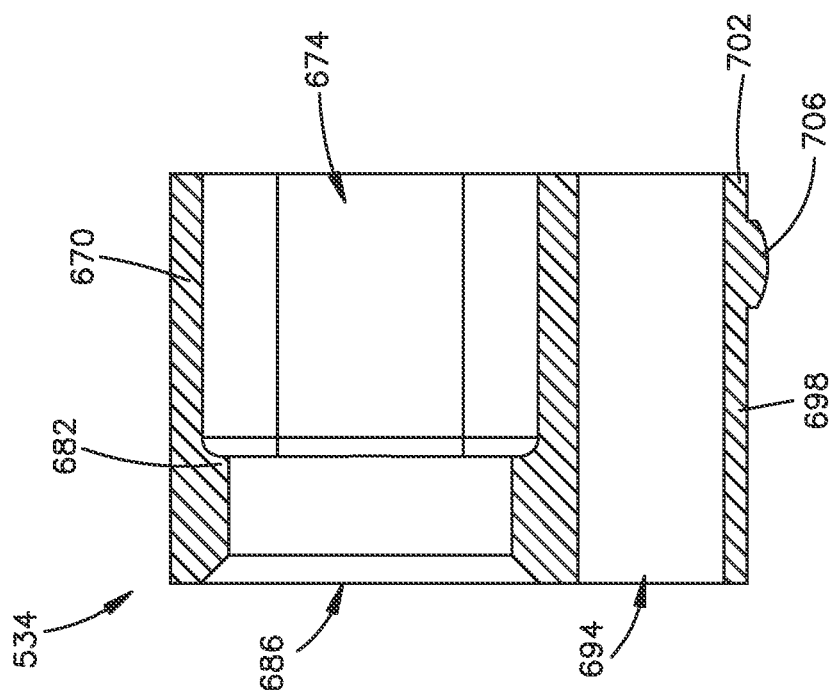
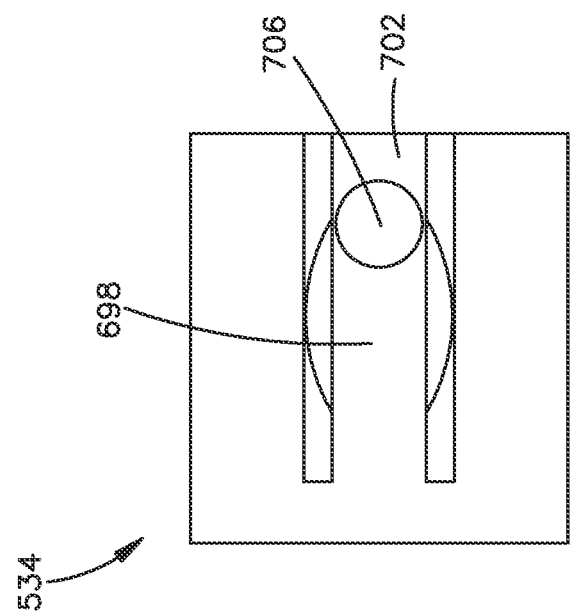

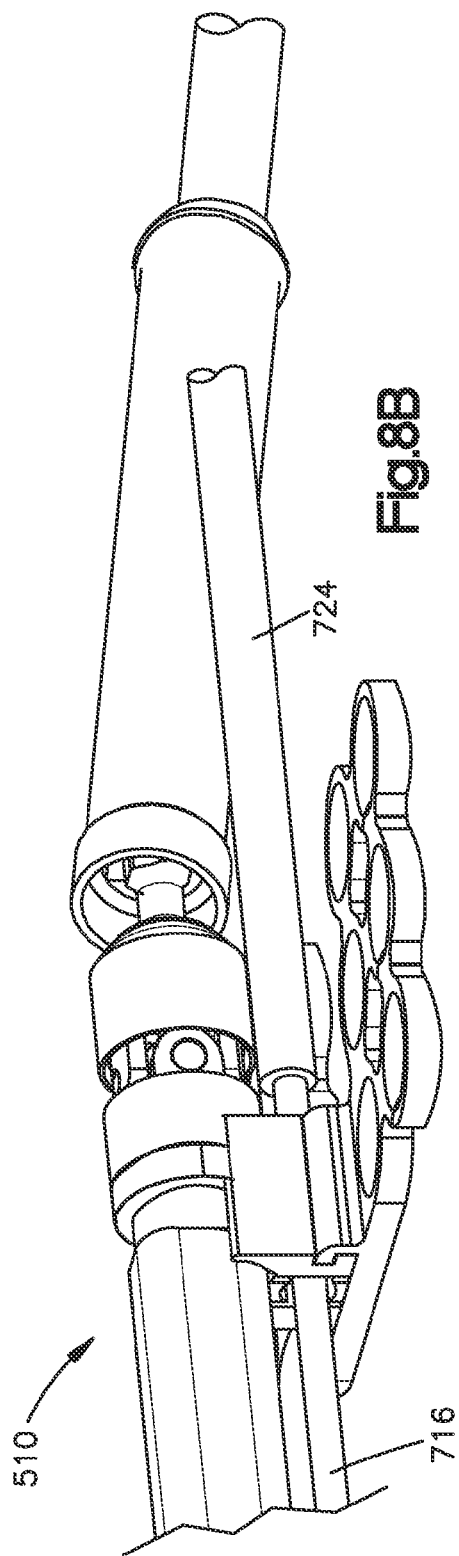
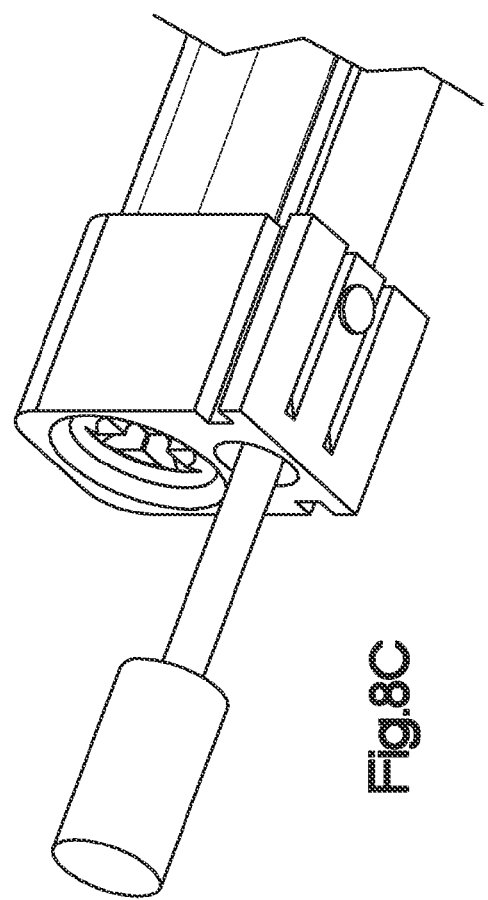

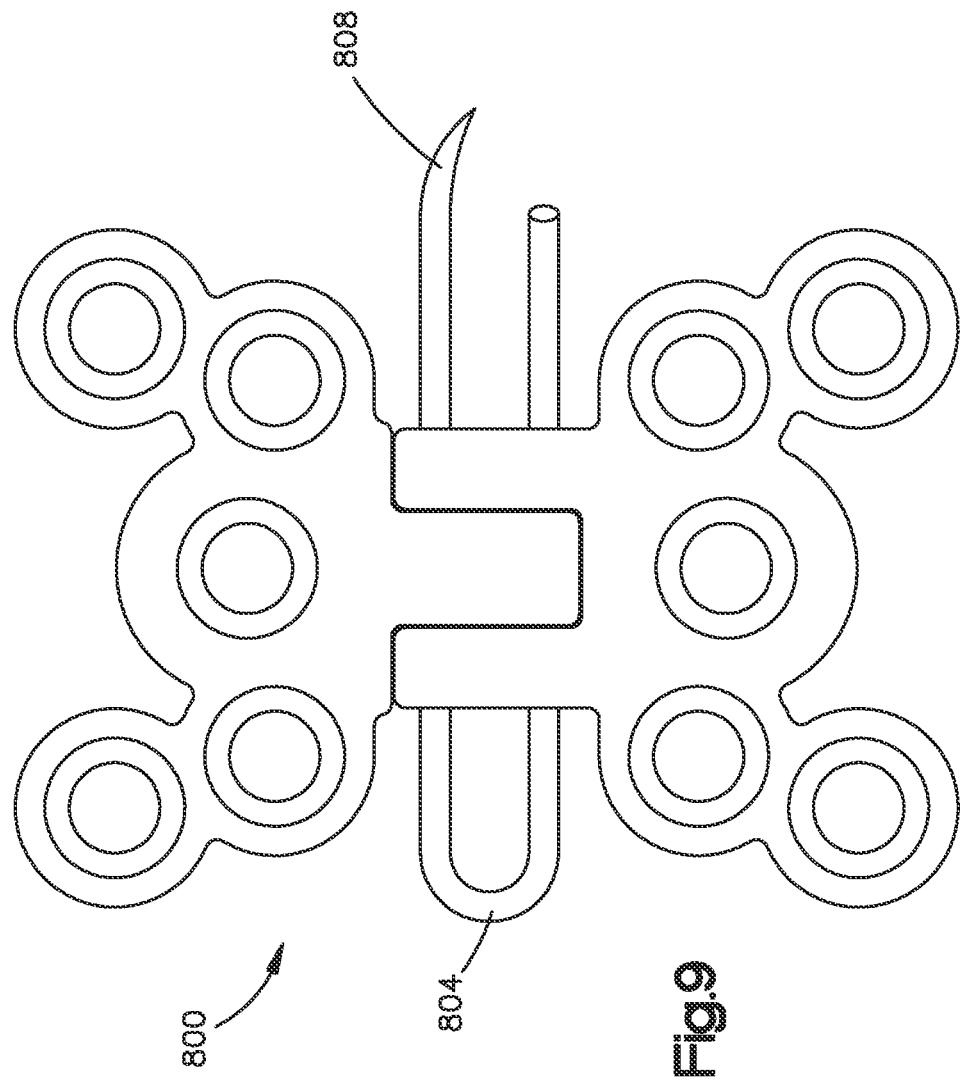

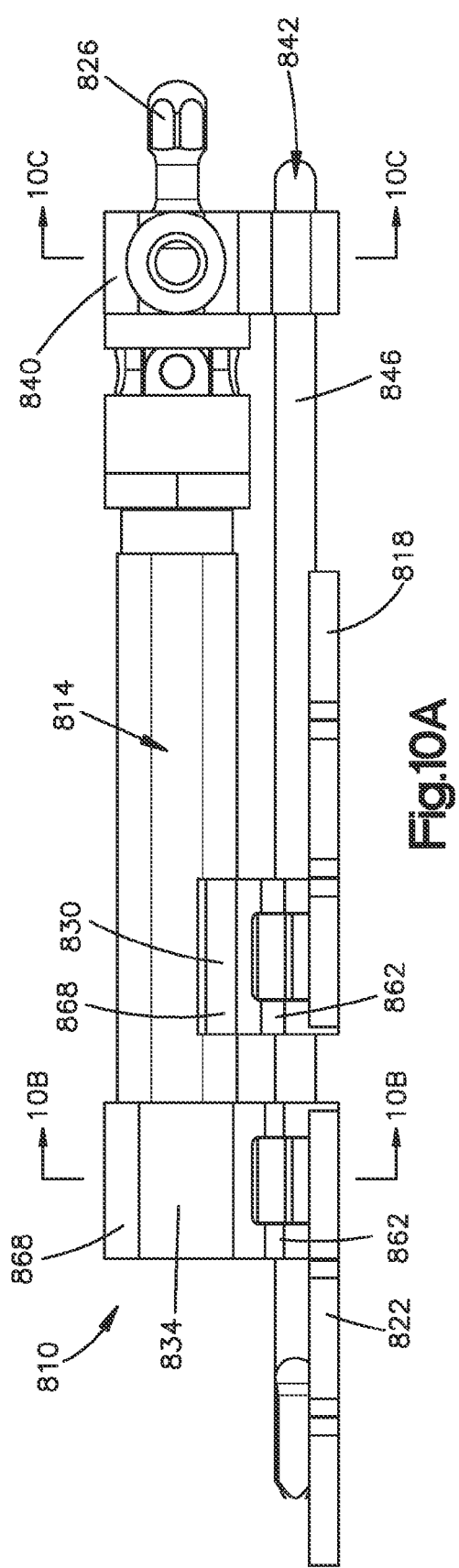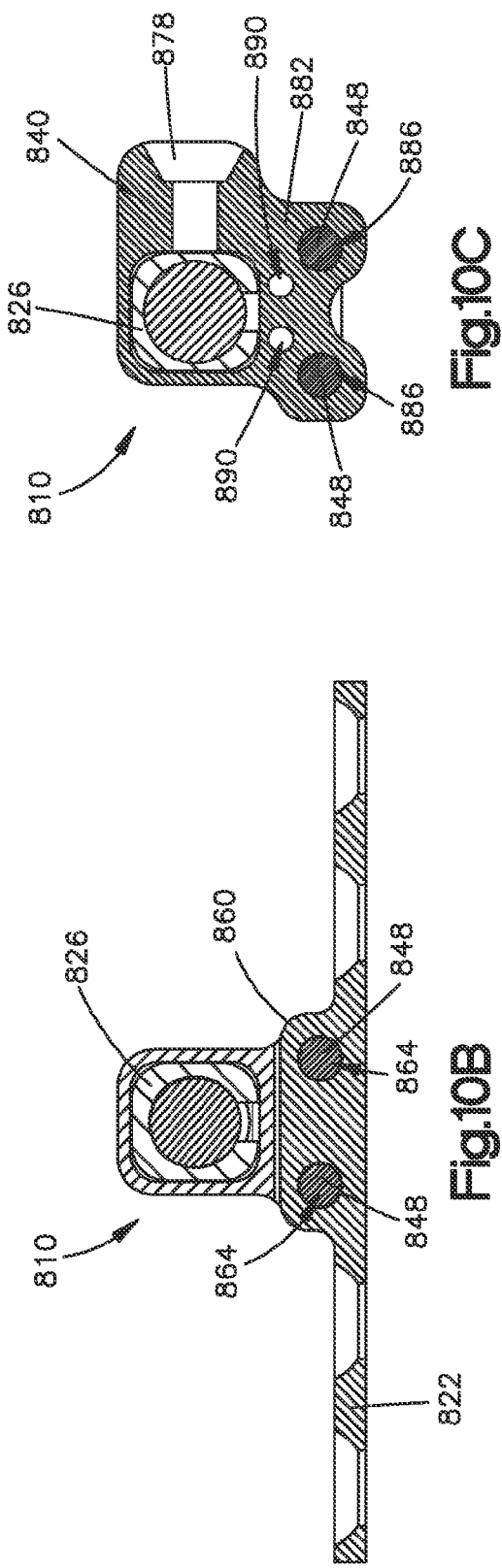
Fig.10A
Fig.10B
Fig.10C

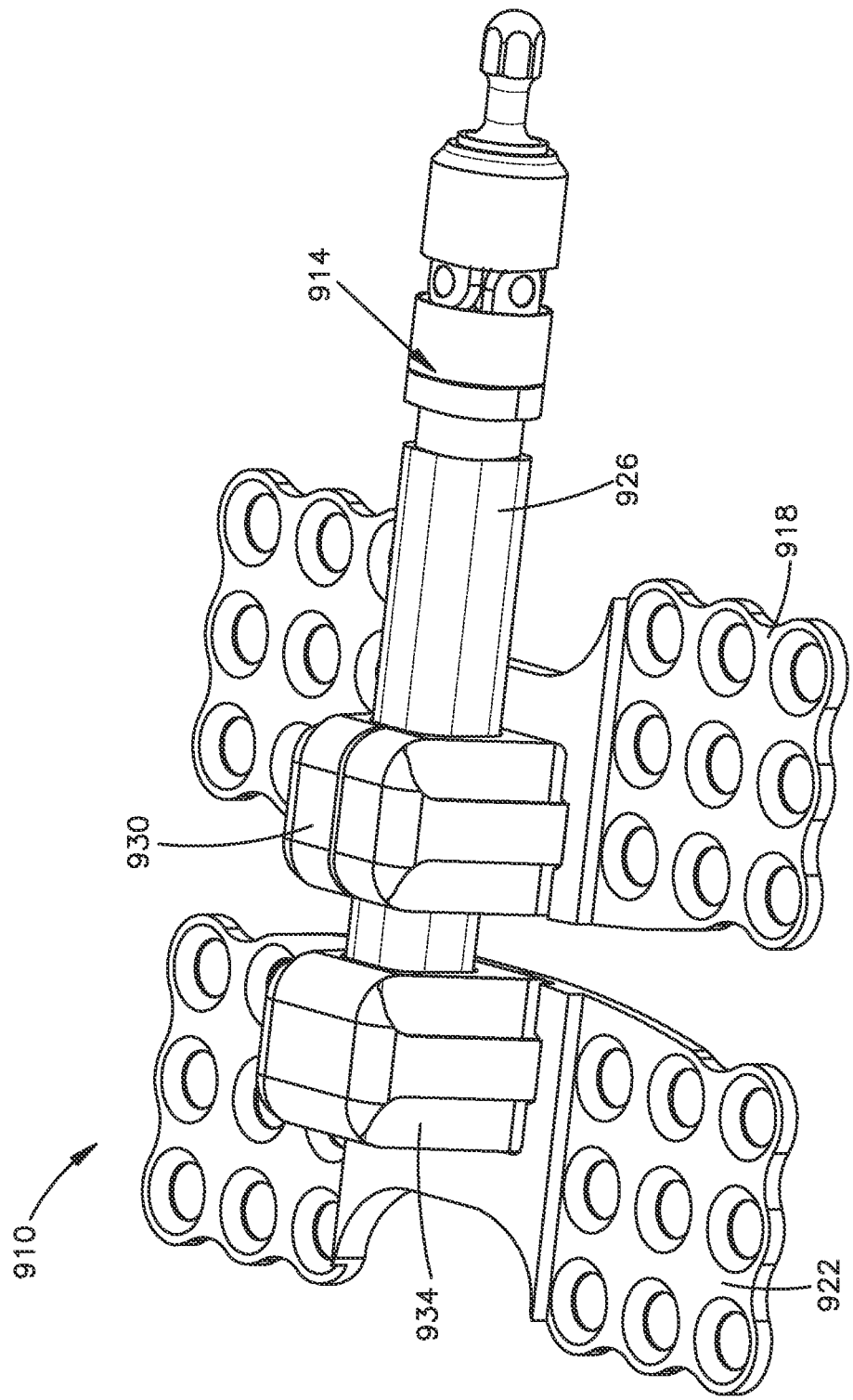

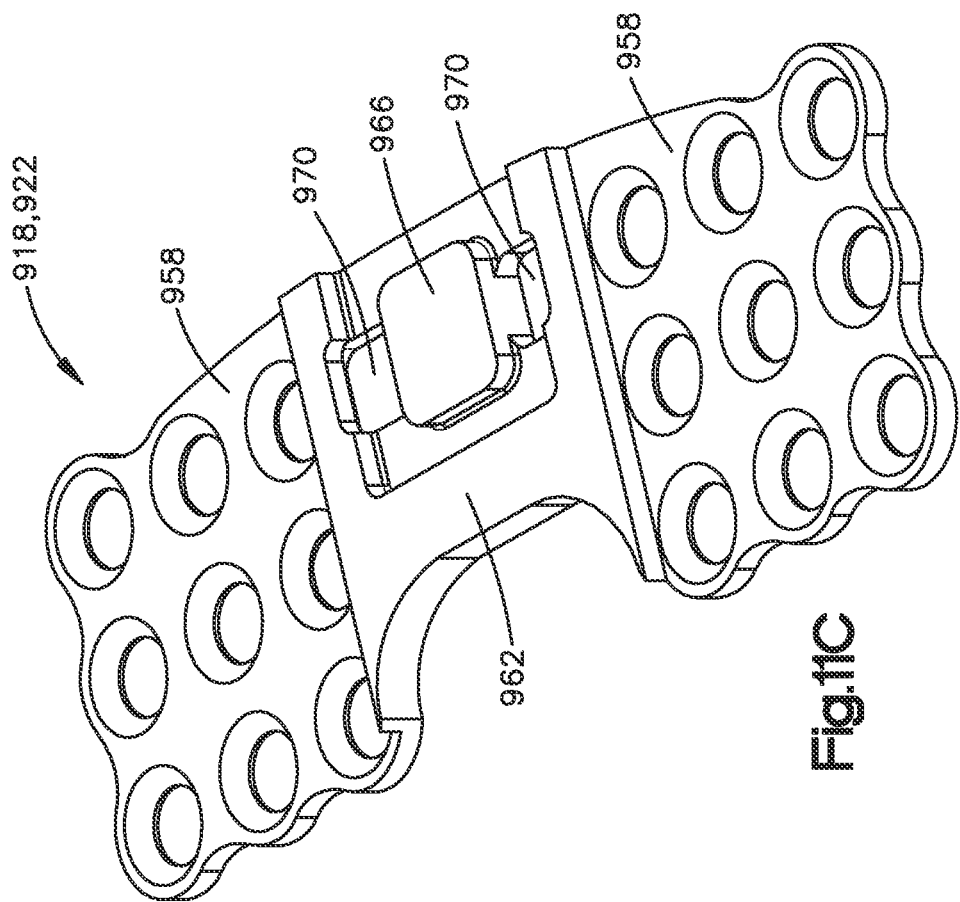
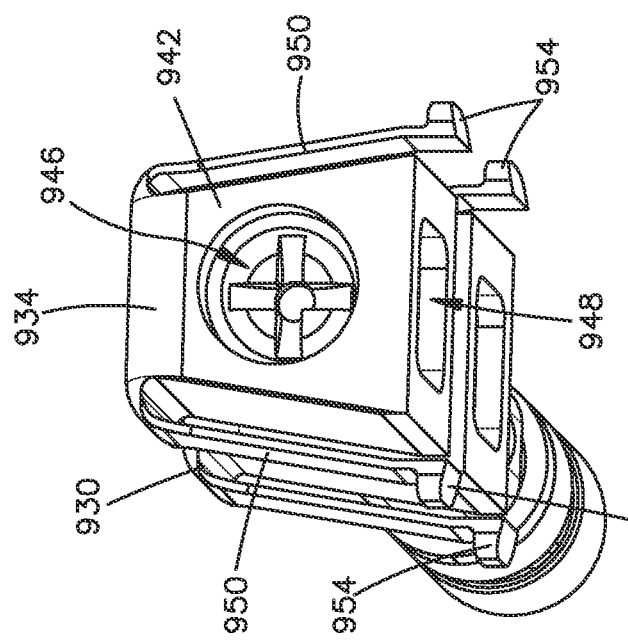

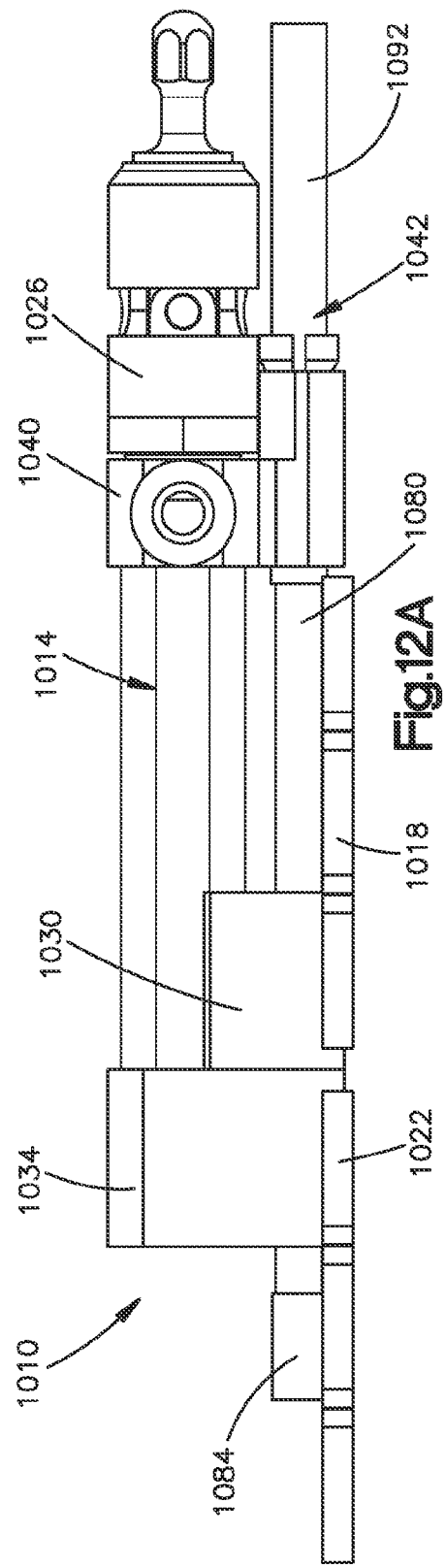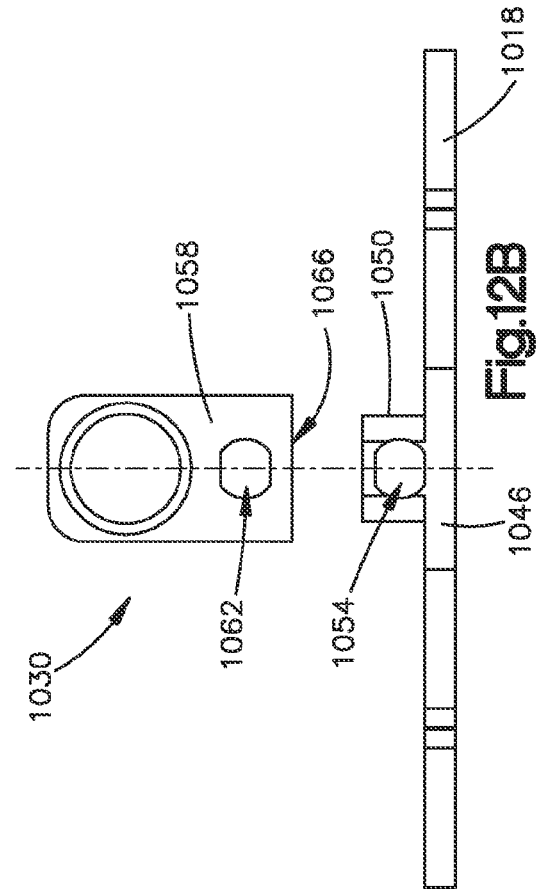

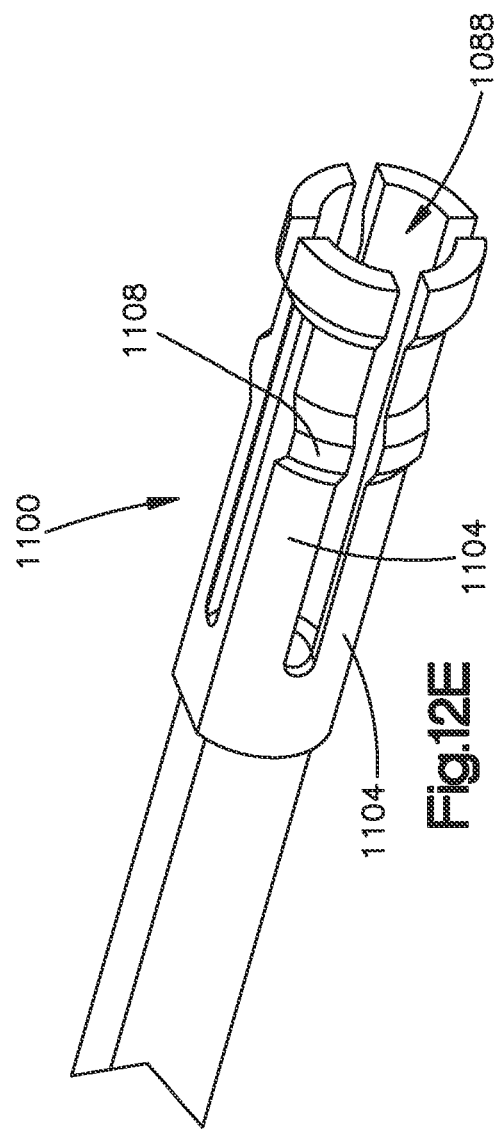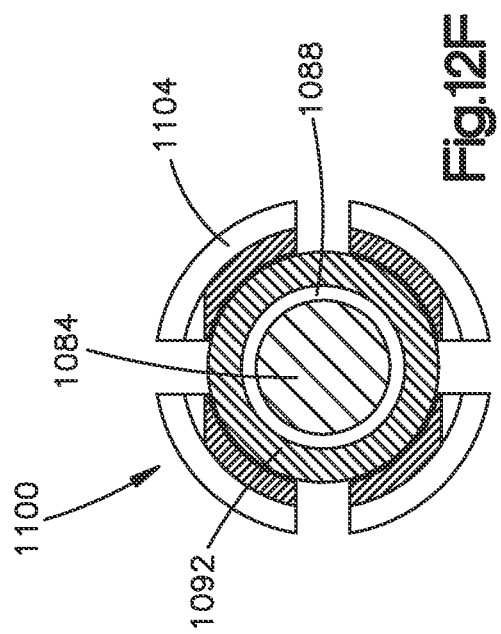

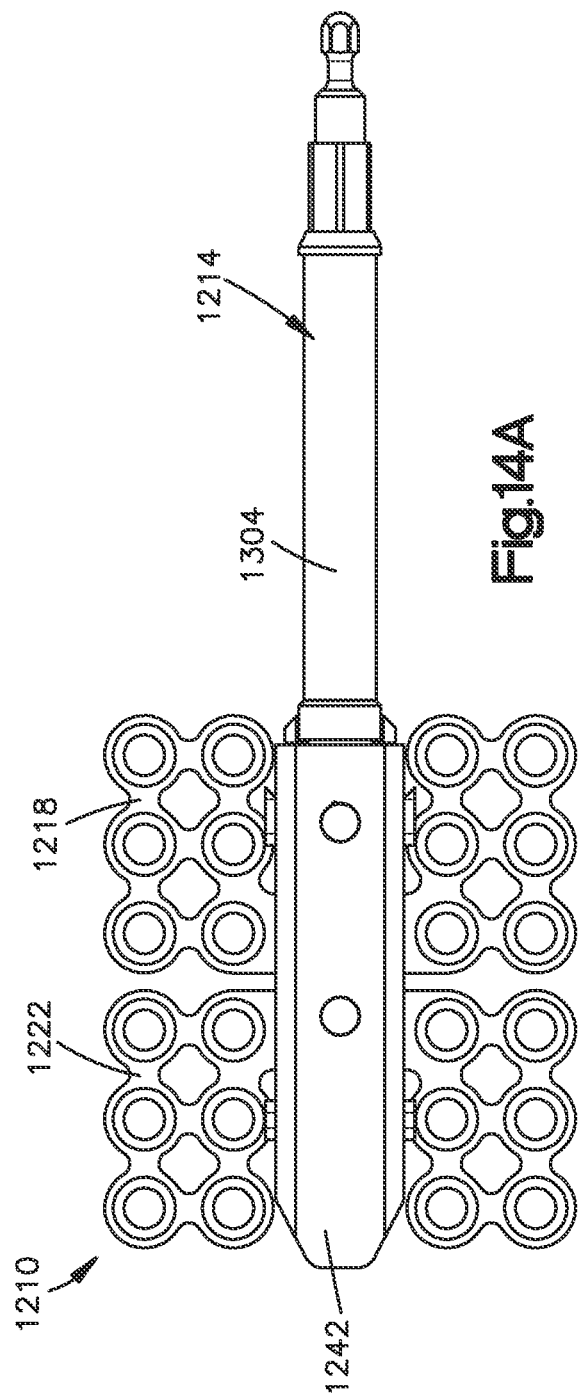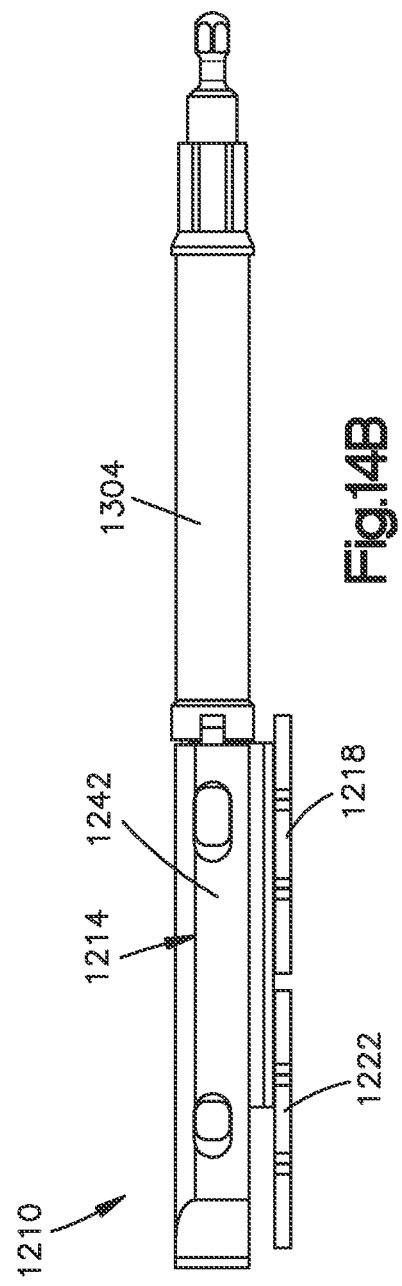

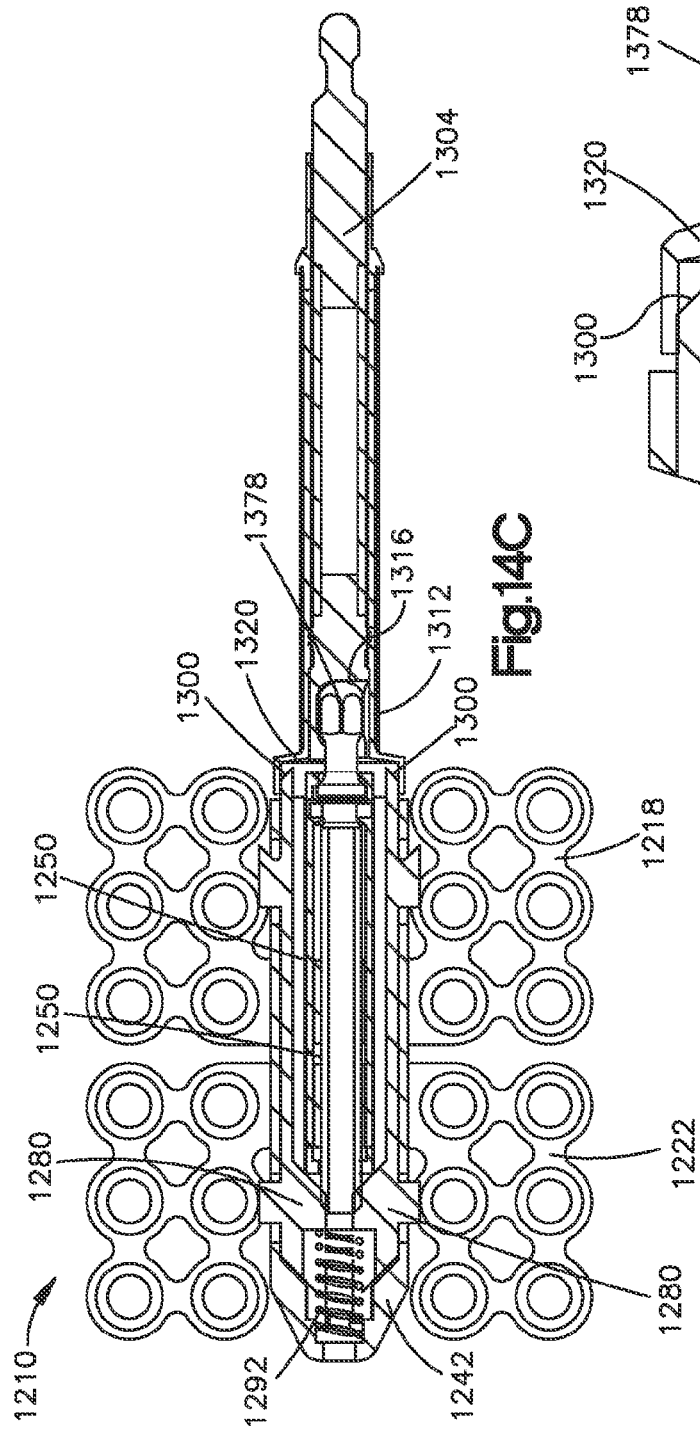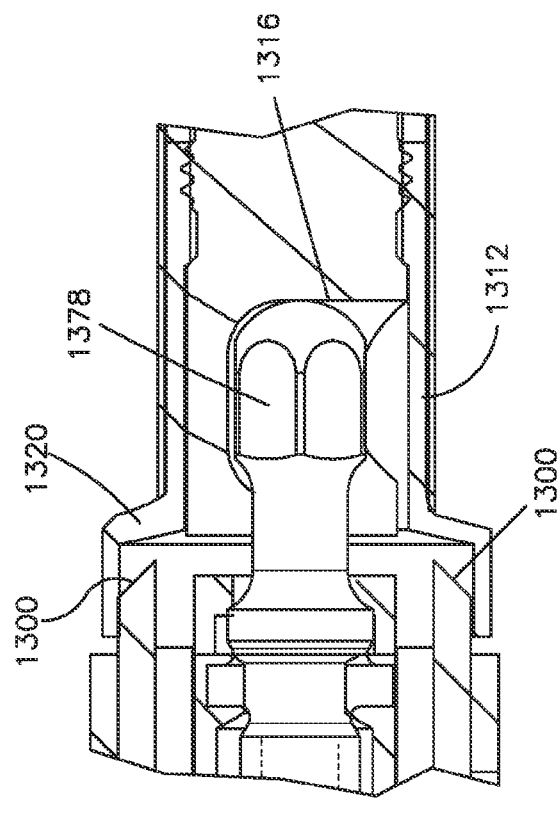

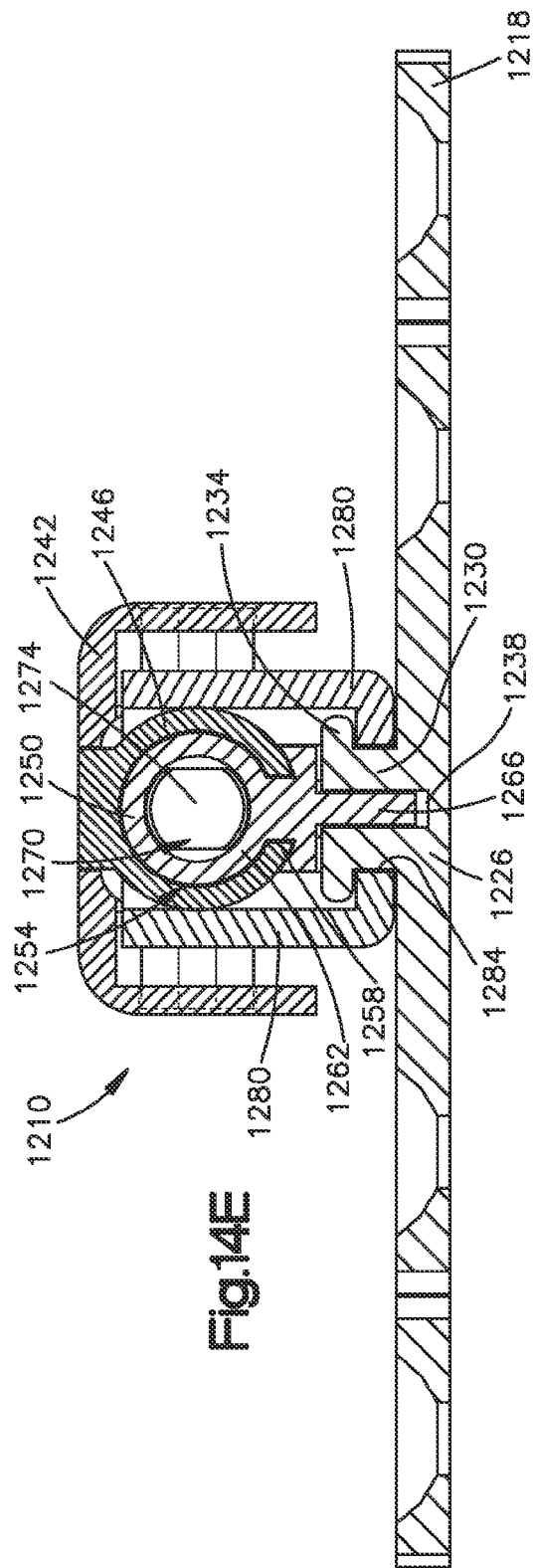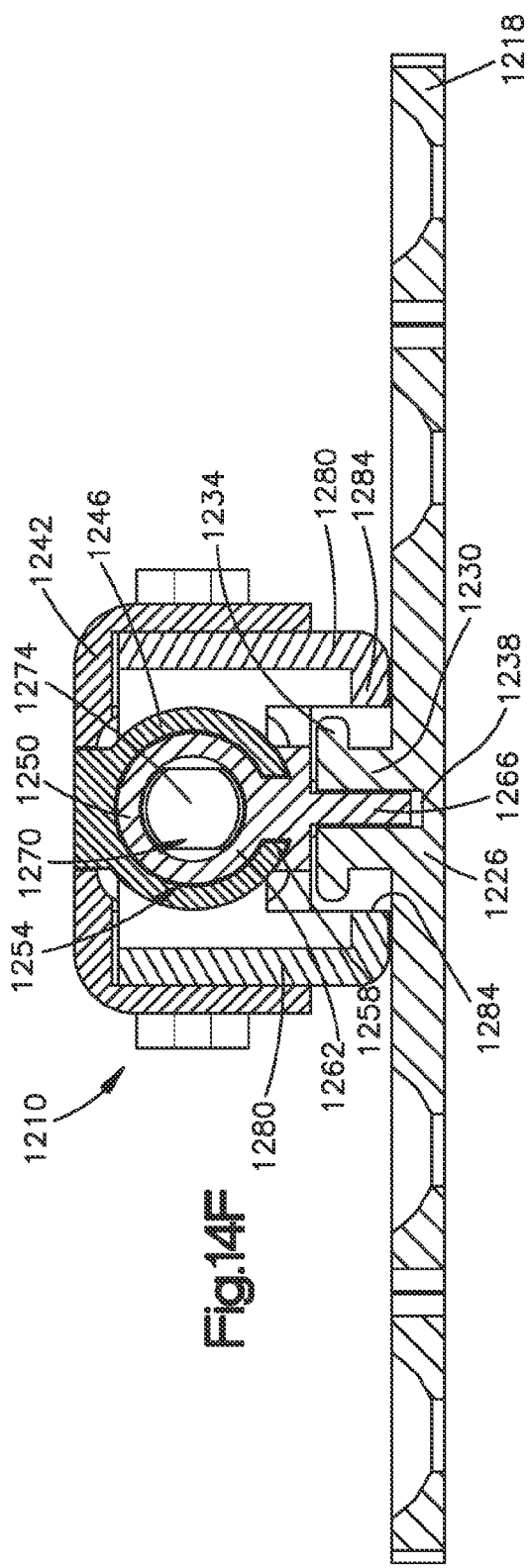

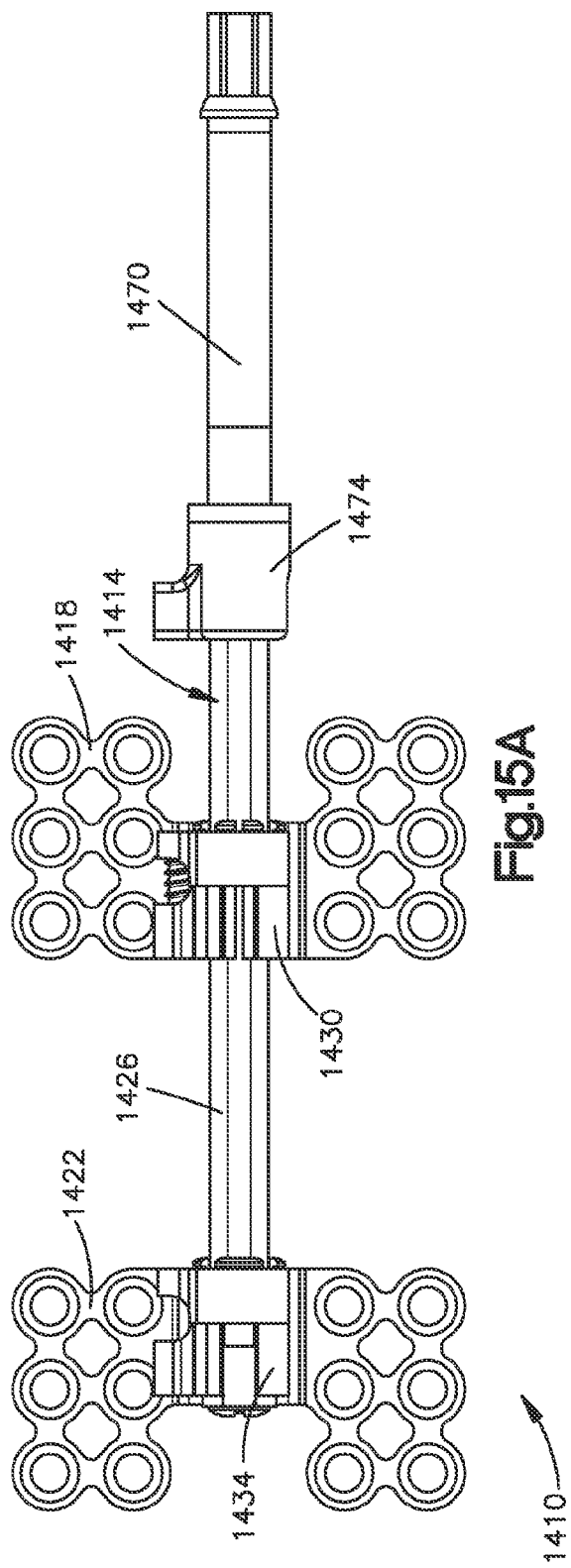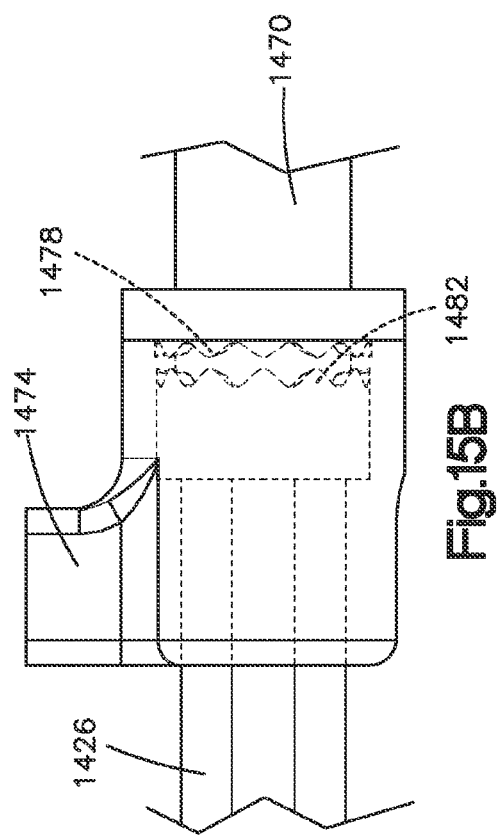

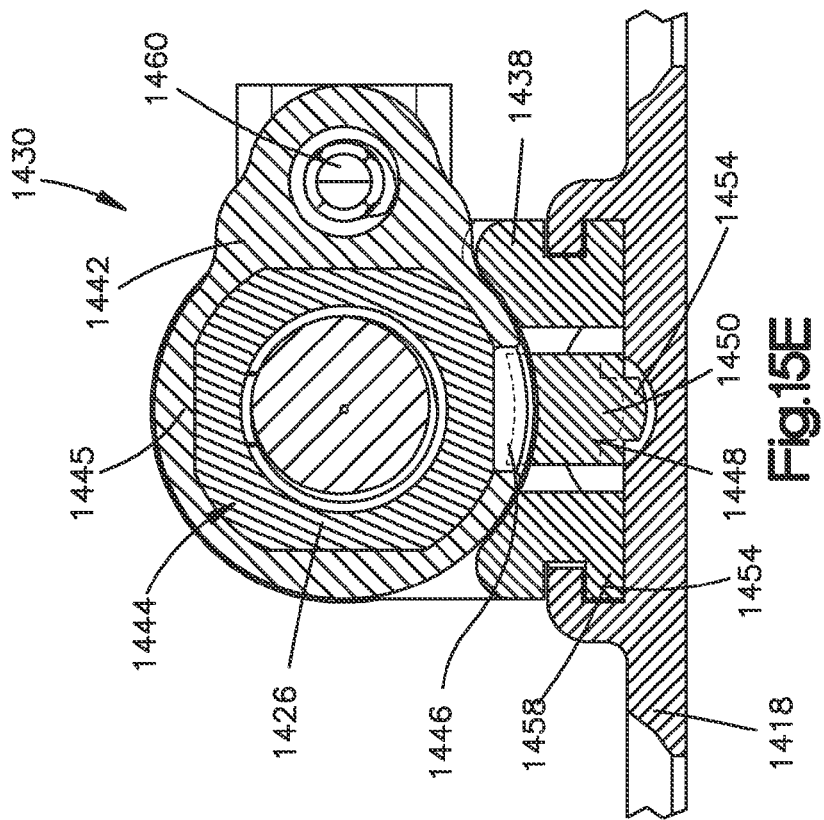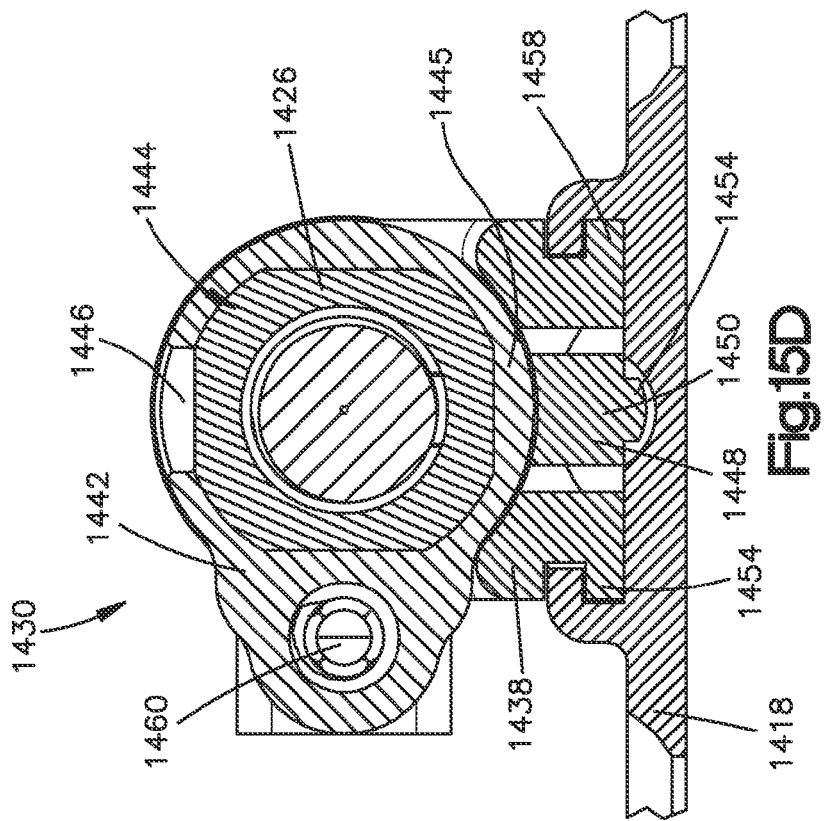

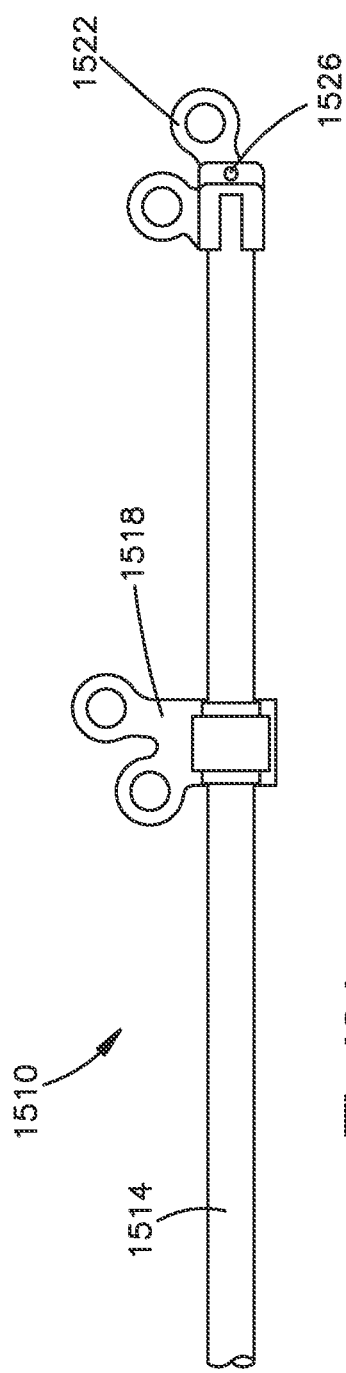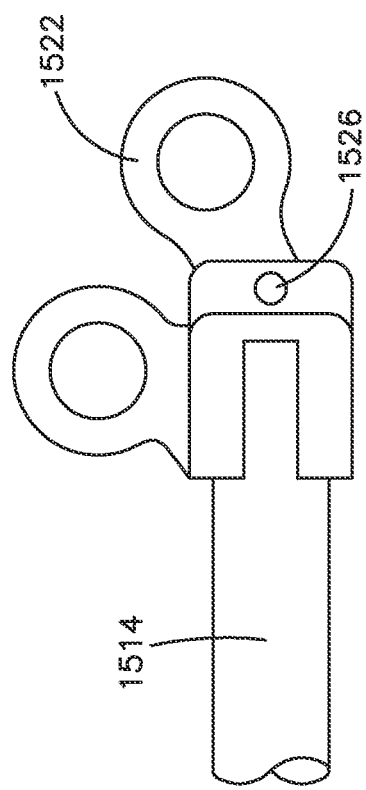

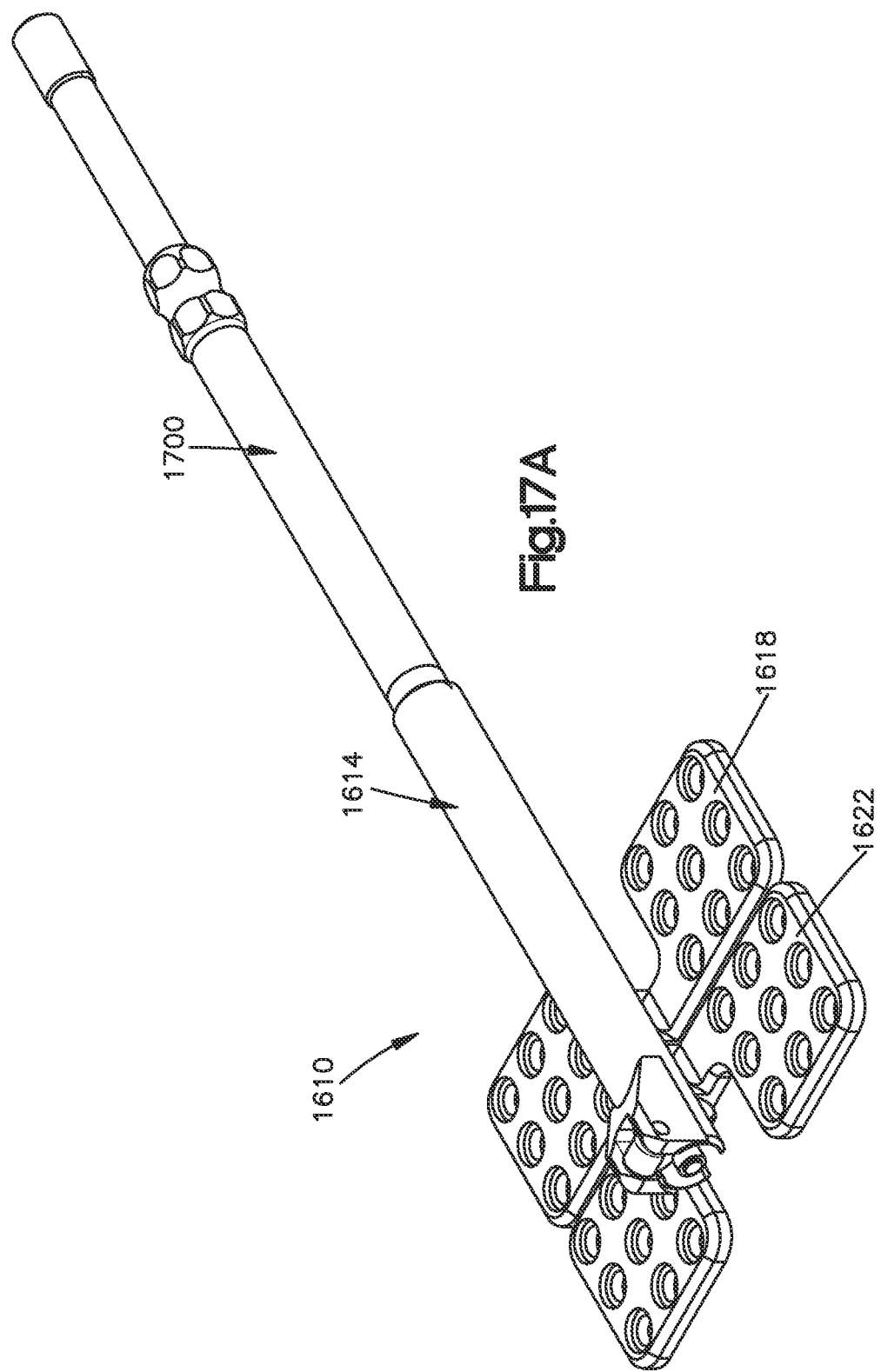

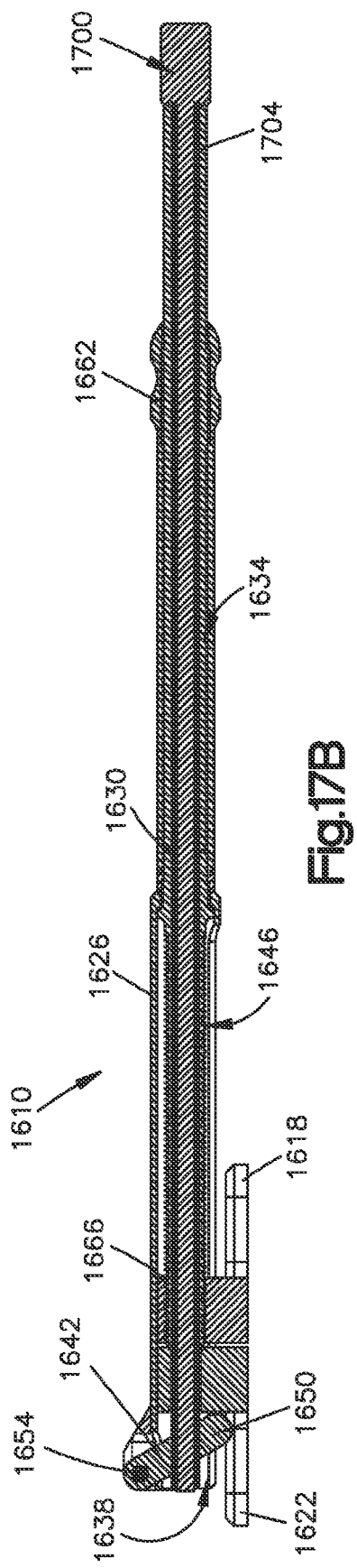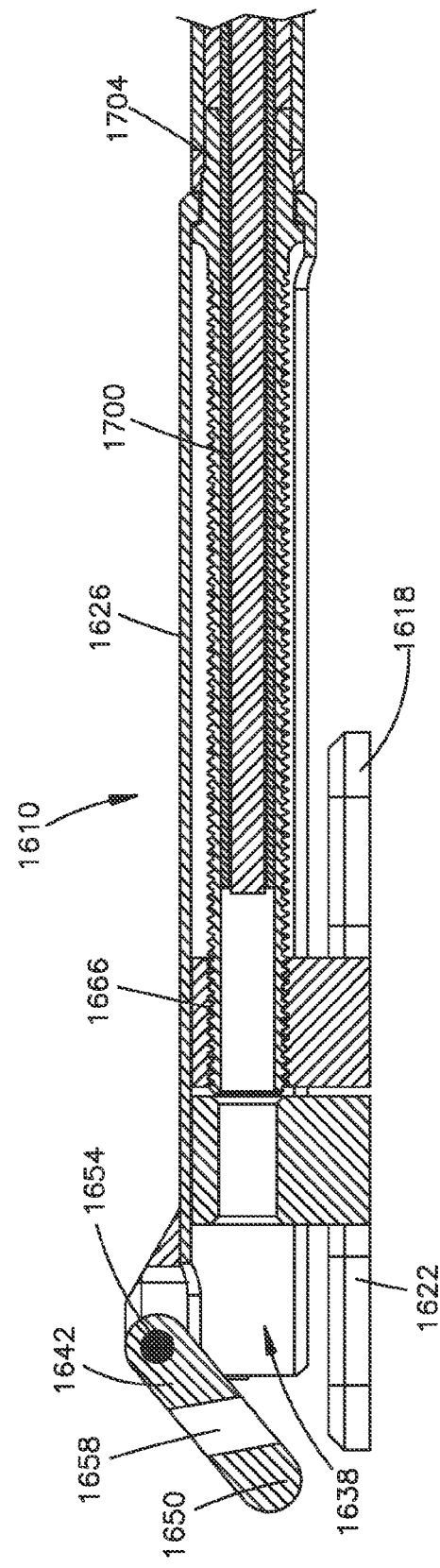

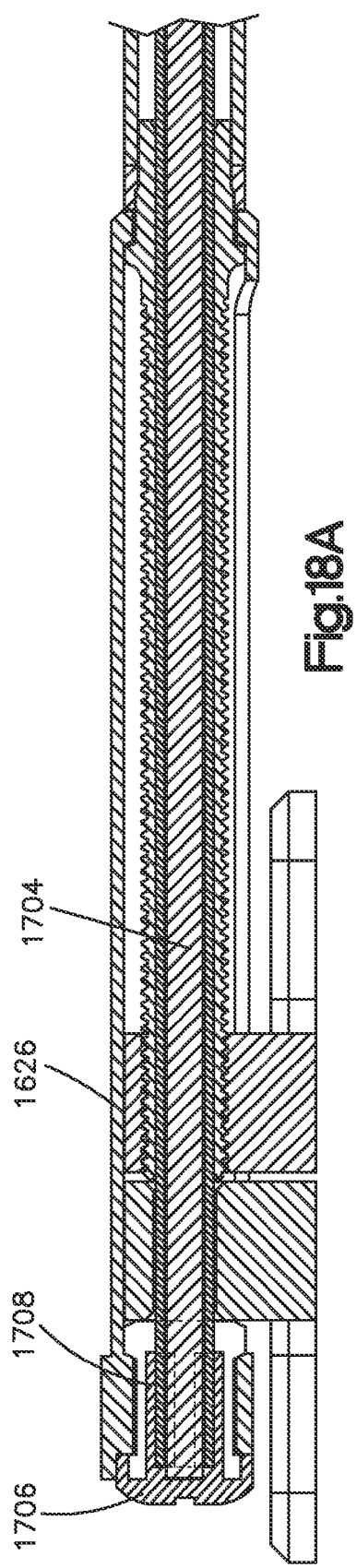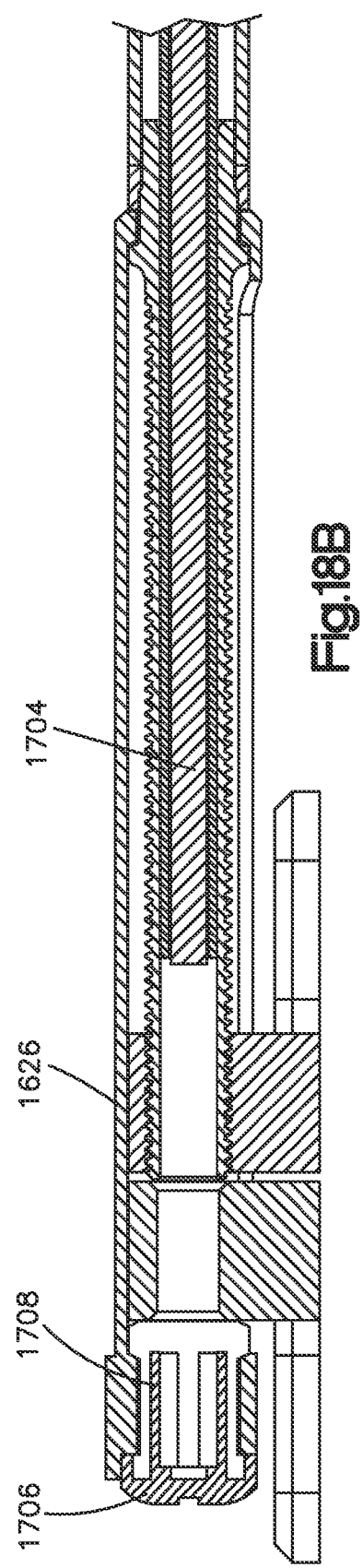

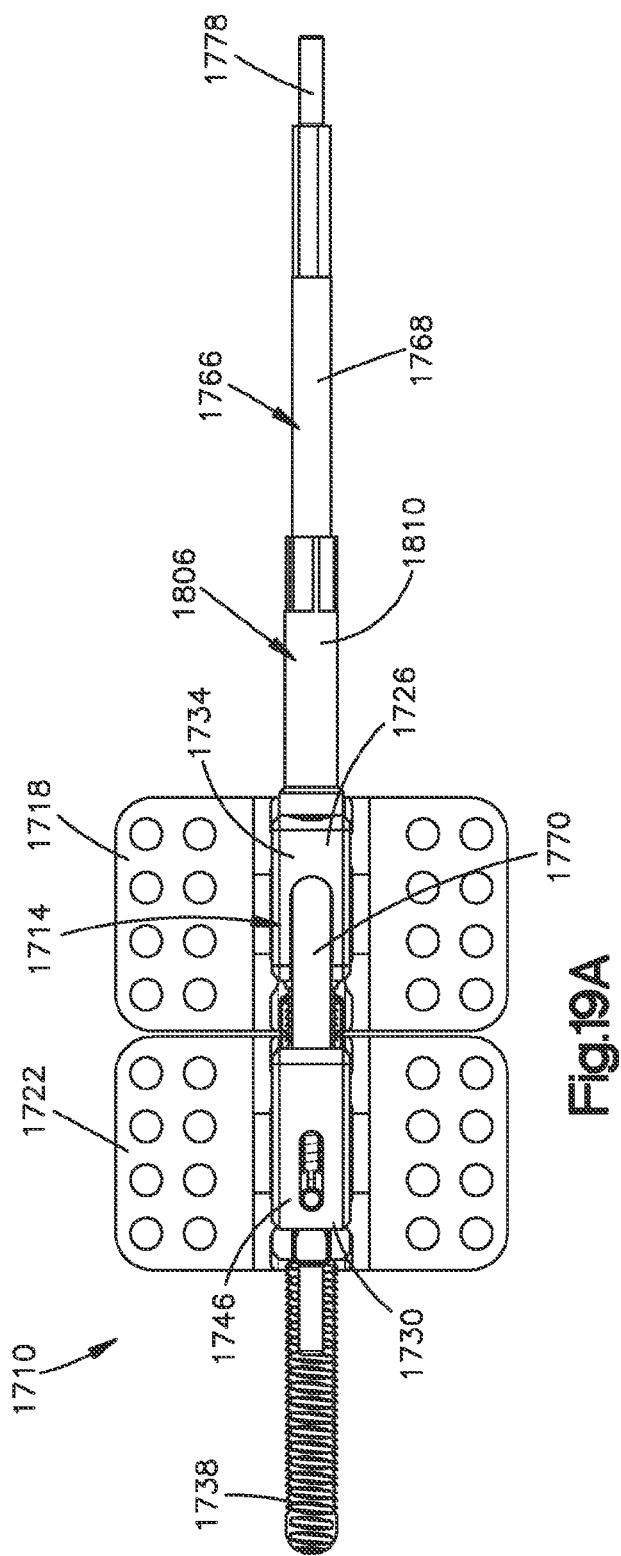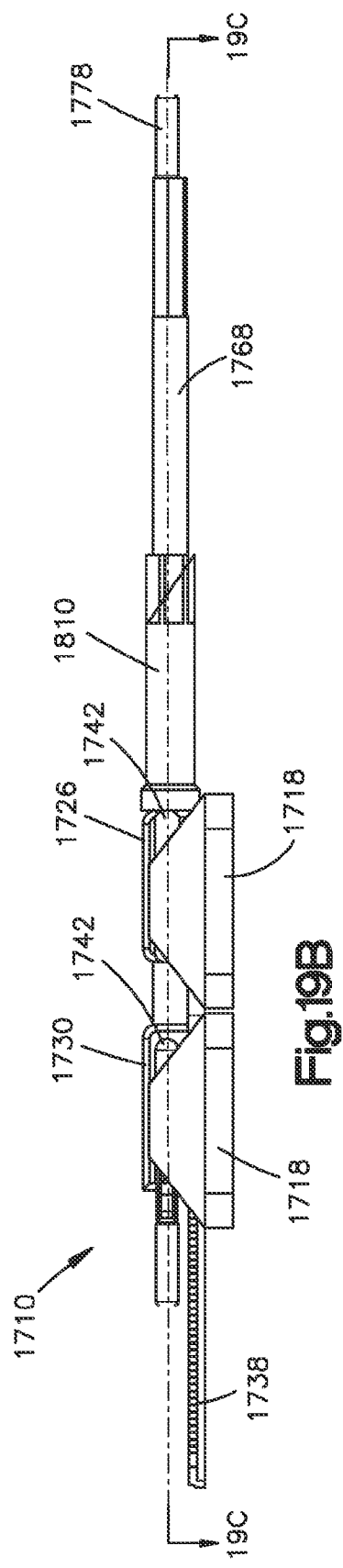
Fig.19A
Fig.19B

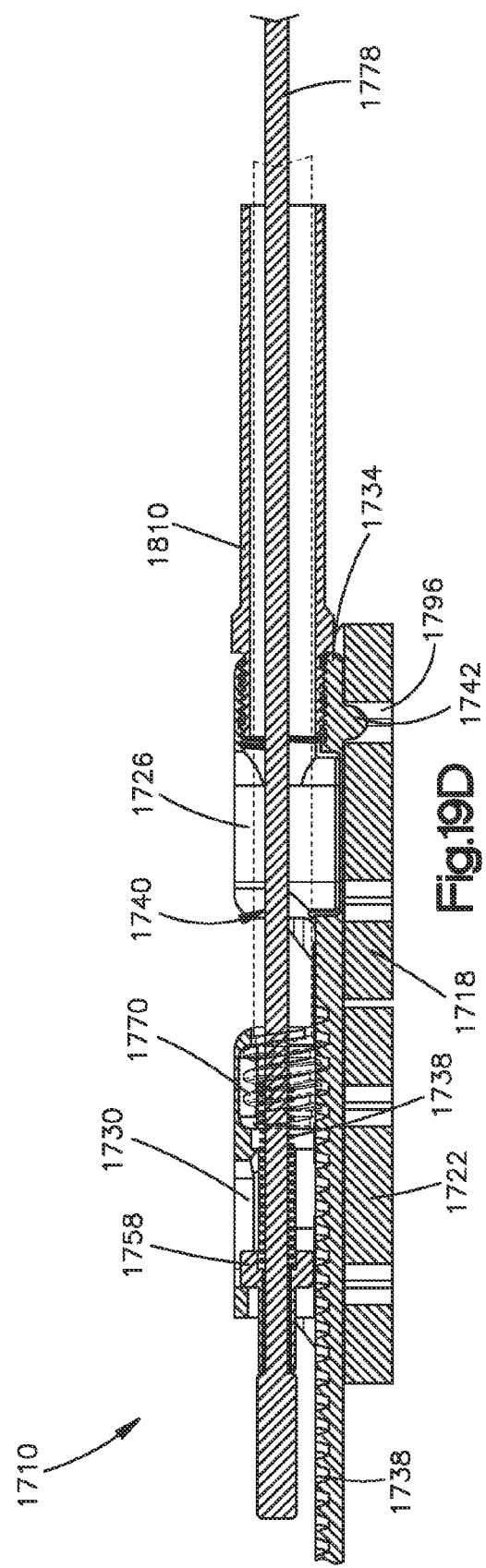

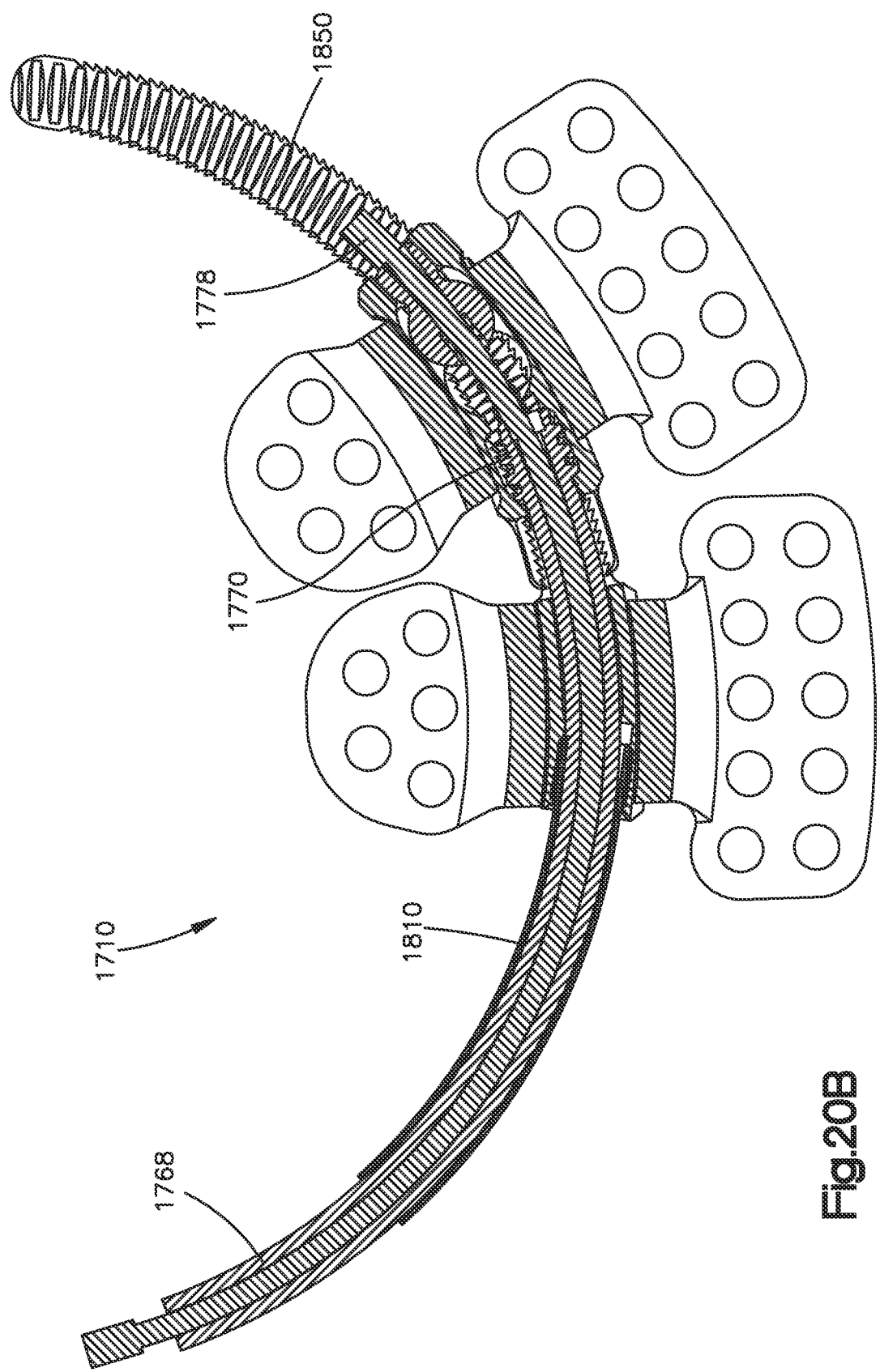

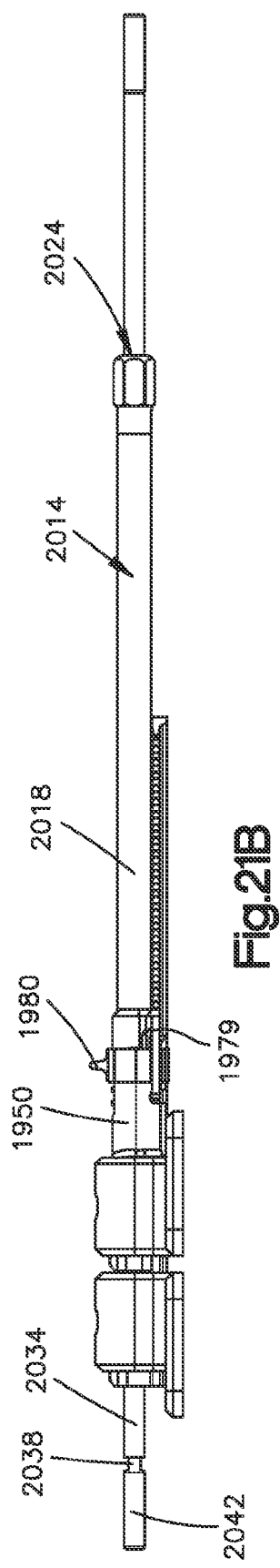
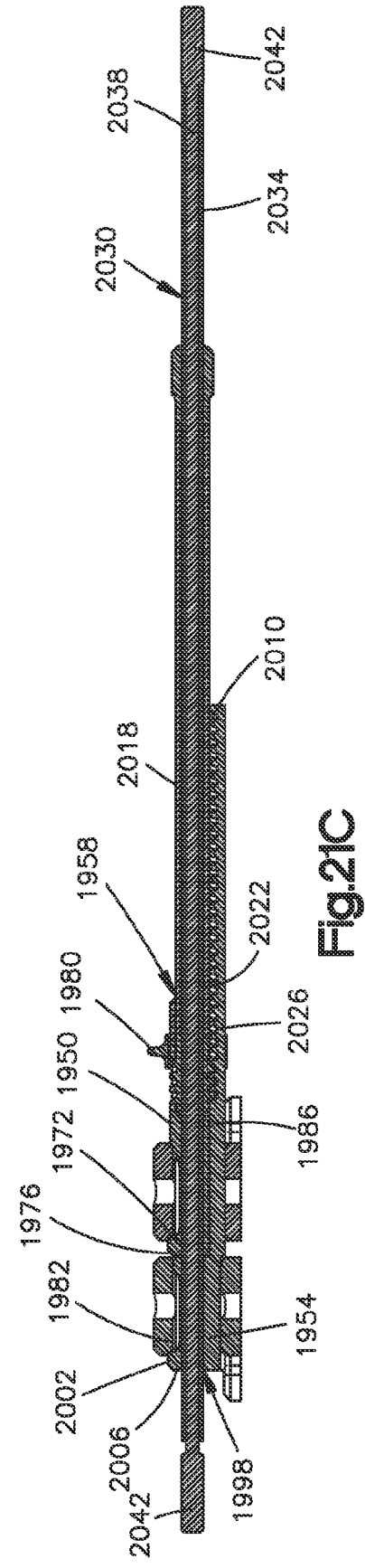

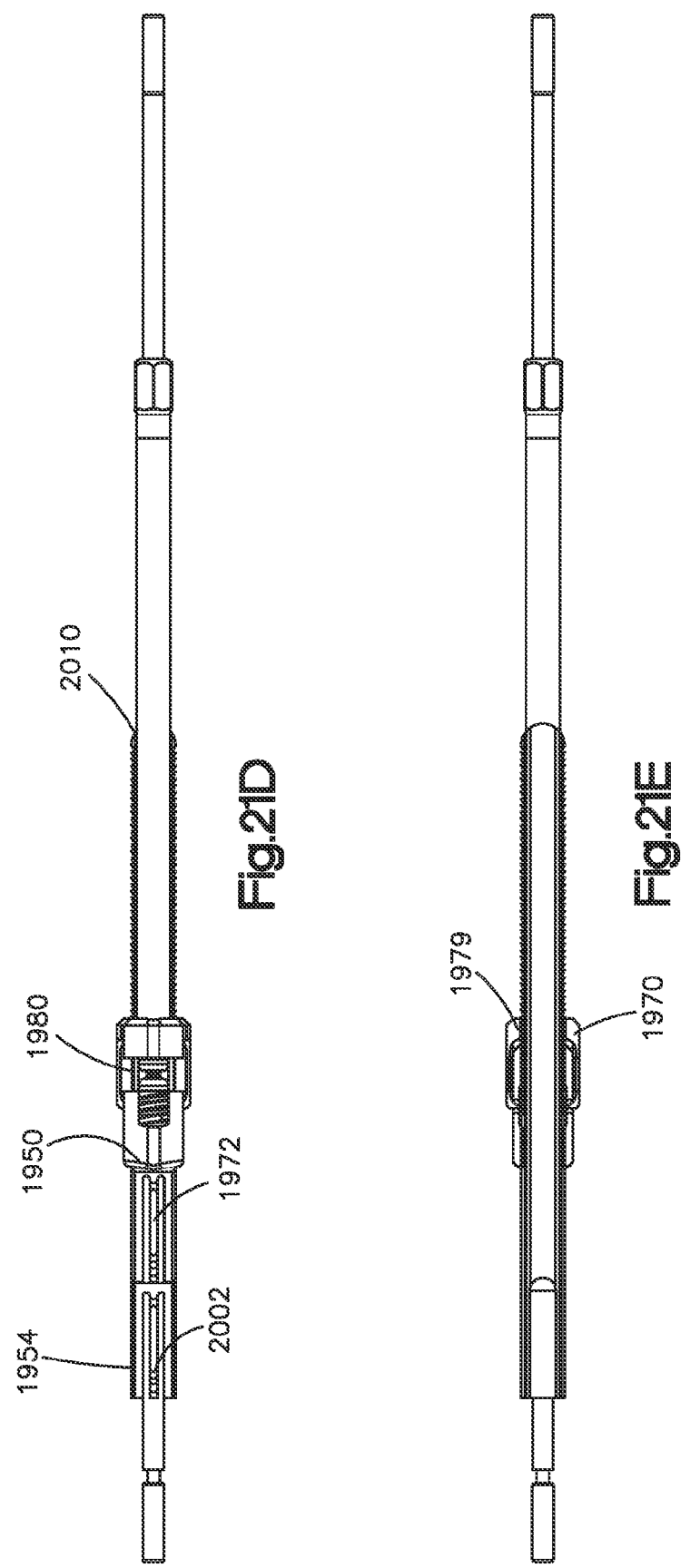

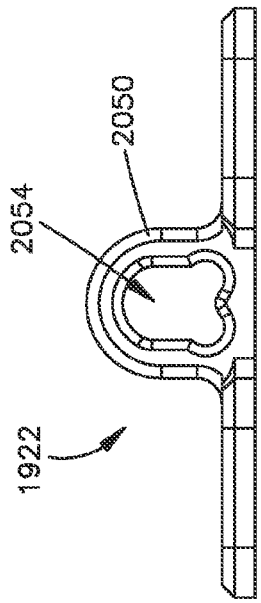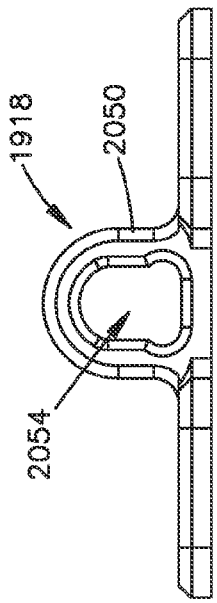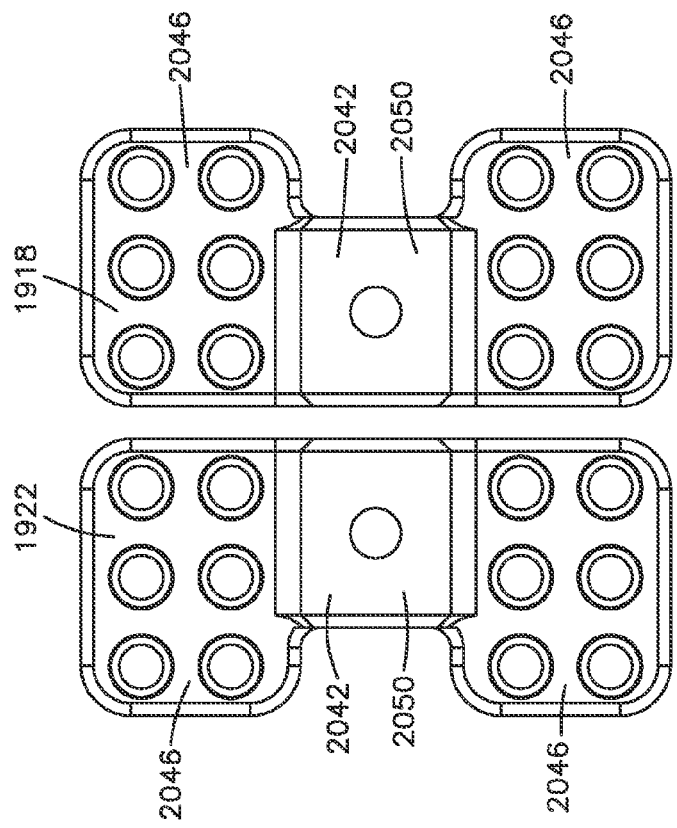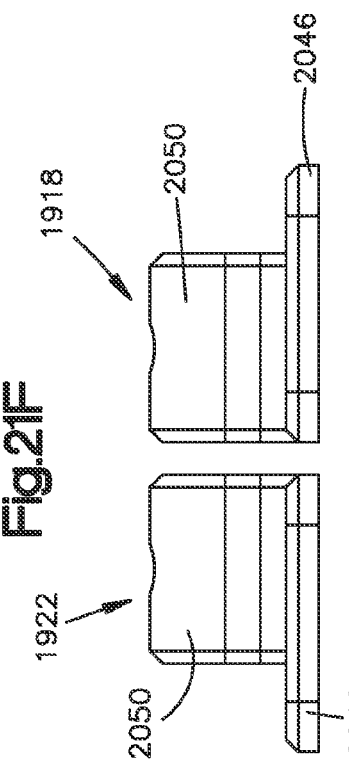

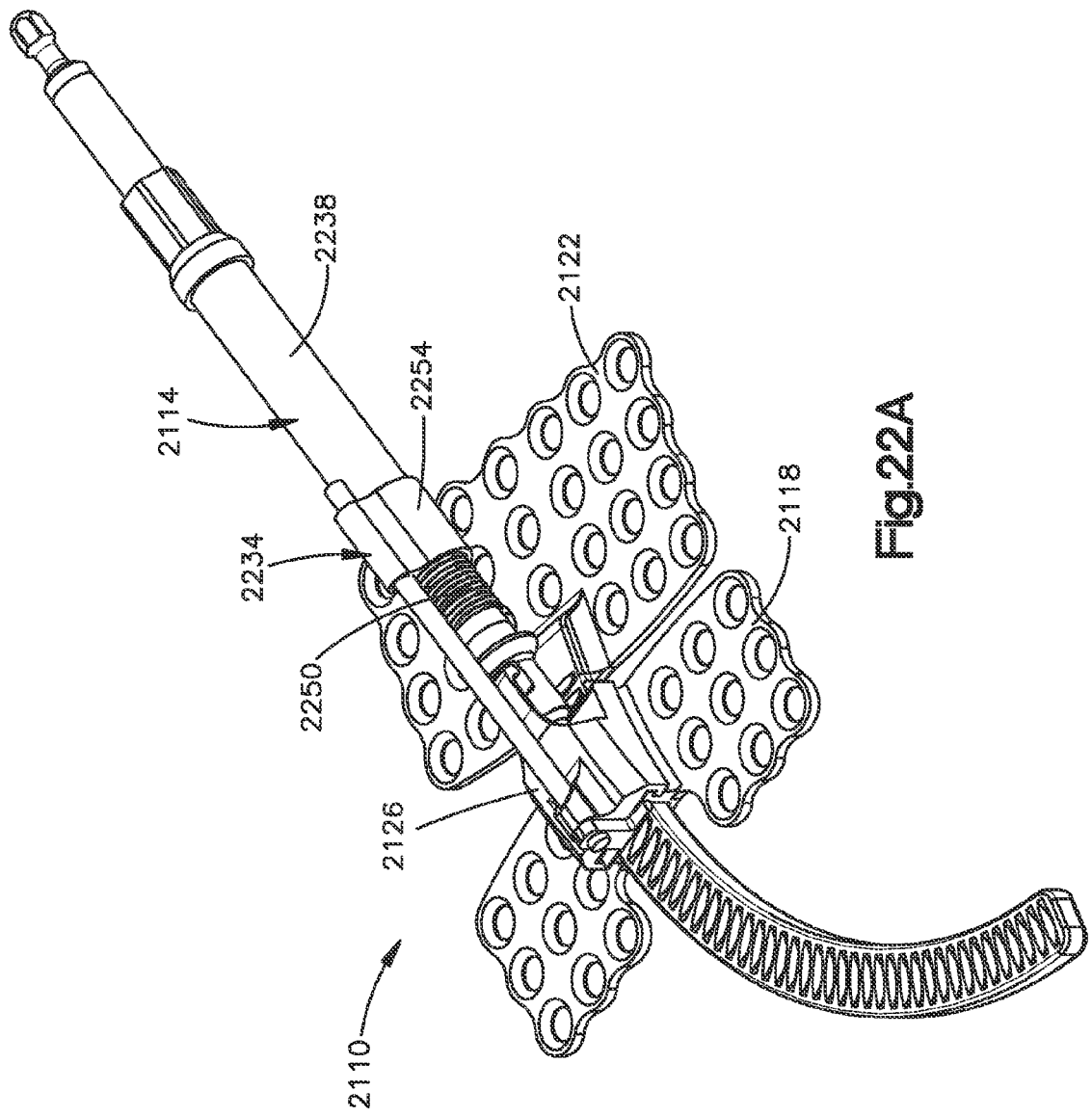

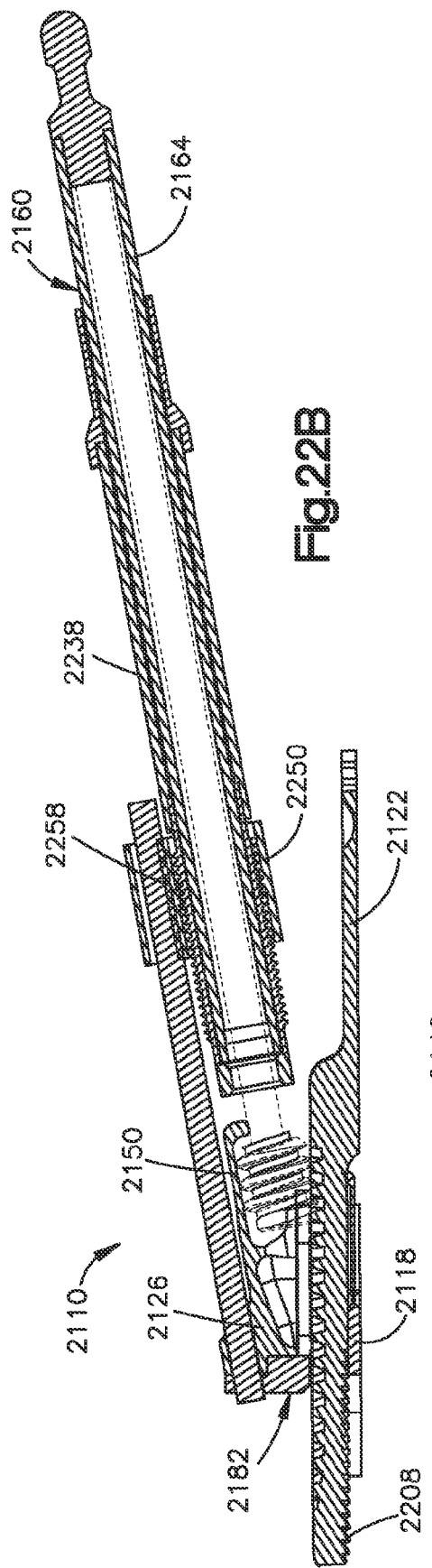
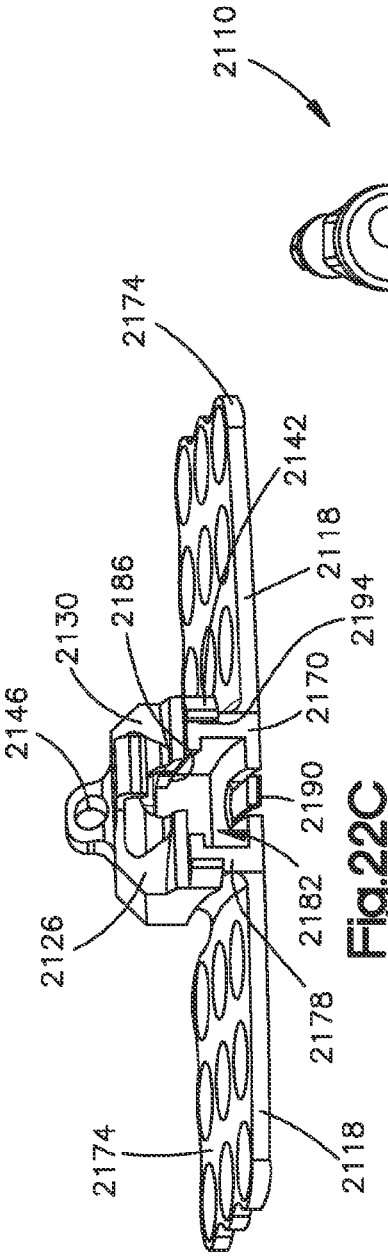
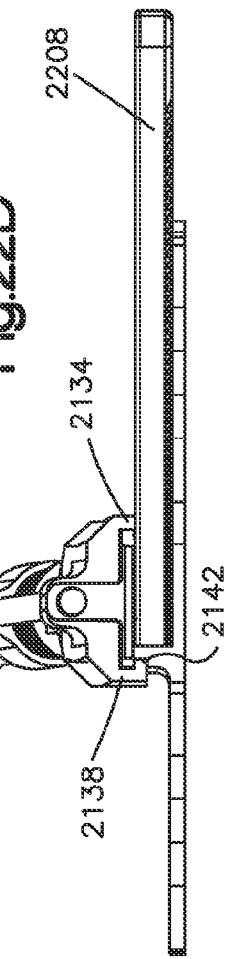

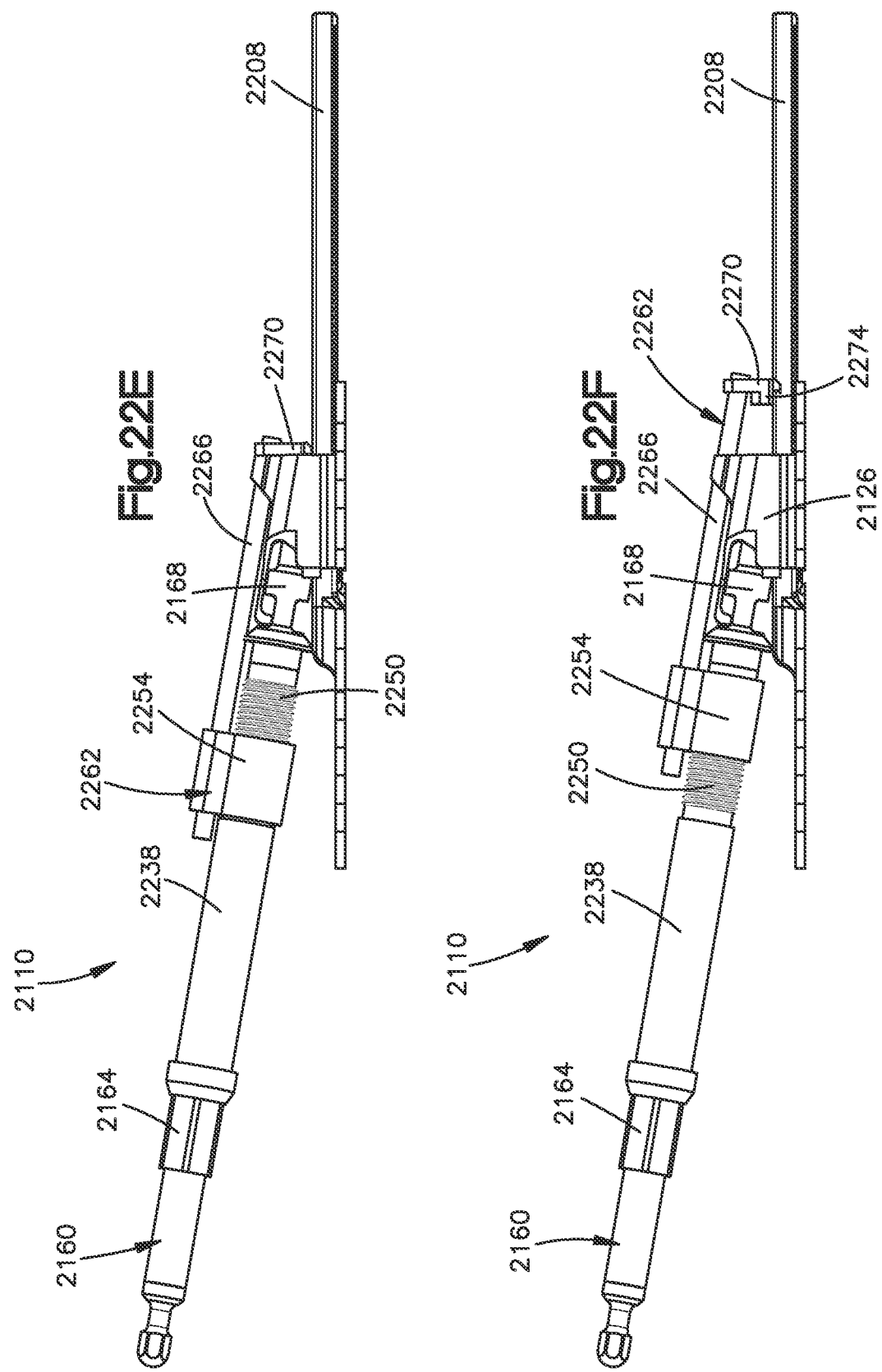

DISTRACTOR WITH REMOVABLE FOOTPLATES

CROSS REFERENCE TO RELATED APPLICATIONS

This application is a divisional of U.S. application Ser. No. 12/890,026 filed Sep. 24, 2010, which claims the benefit of U.S. provisional application 61/245,561 filed Sep. 24, 2009, the contents of which are incorporated by reference in their entirety.

BACKGROUND

Various developmental disorders of the human skull result in craniofacial abnormalities in which certain bones fail to grow in proper proportion to other bones, or in which certain bones fuse prematurely, causing malformation of the midface or mandible. For example, one disorder, Pierre Robin Sequence (PRS) is a complex condition in which infants are born with a micrognathic and/or retrognathic mandible that causes glossoptosis, resulting in respiratory distress. Mandibular distraction is a treatment option, in which the mandible is advanced anteriorly, thereby pulling the tongue forward and opening up the airway.

A chief complaint among surgeons who use internal mandible distractors to treat infants with certain disorders such as PRS is that some distractors require a second surgical procedure for removal. The removal procedure is difficult for several reasons: (1) the locations of the footplates change during the course of treatment making them difficult to access through the same incision that was used for distractor implementation, and (2) soft and hard tissue grows over the bone screws during treatment making it difficult to engage the screwdriver blade into the screw recess for removal.

Distractors that use resorbable footplates have been used to avoid the second surgical procedure, however, there have been complaints with the current distractors that are used. For example, one distractor consists of a metallic drive screw with a metallic activation extension that engages two resorbable footplates, and can be detached by externally reversing the metallic drive screw at the end of the consolidation phase and removing it through the percutaneous activation port. Such a distractor has reportedly had problems with strength and bone segment stability.

SUMMARY

Bone distractor assemblies configured to distract and/or reduce first and second bone segments on opposite sides of a bone gap are provided. In one embodiment the distractor assembly includes a distractor having a first coupler and a second coupler, a first footplate configured to be releasably engaged to the first coupler, and a second footplate configured to be releasably engaged to the second coupler. The first and second footplates are configured to attach to bone. The assembly further includes a locking mechanism including a tube that is movable with respect to the distractor between a locked position and a released position. When the tube is in the locked position, the tube maintains the first and second footplates in engagement with the first and second couplers, respectively. When the tube is in the unlocked position, the first and second footplates are disengaged from the first and second couplers, respectively. The assembly further includes a release actuator that extends through the tube and is operably coupled to the distractor, such that movement of the release actuator to a removal position causes the distractor to be removed from the first and second footplates.

In another embodiment the distractor assembly includes a first footplate, a second footplate translatably coupled to the first footplate, and a distractor releasably coupled to the first footplate. The second footplate includes an extension that carries a track. The distractor is releasably coupled to the first footplate and includes an activation worm and a sleeve. The activation worm is configured to engage the track, such that rotation of the worm causes the second footplate to translate relative to the first footplate. The sleeve includes a distal coupling portion that is configured to releasably lock the activation worm to the first footplate.

In another embodiment the distractor assembly includes a distractor, a first footplate releasably coupled to the distractor, and a second footplate releasably coupled to the distractor. The first and second footplates each have a central bridge portion that includes a pair of protrusions that define a recess therebetween. The distractor includes a body defining a bore, a pair of barrels disposed within the bore of the body, and a pair of rails disposed about the body. Each barrel includes a protrusion that extends through a slot of the body and engages a recess of a respective footplate. Each rail is configured to selectively engage the protrusions of the first and second footplates to thereby releasably attach the footplates to the distractor.

In another embodiment, the distractor assembly includes a first coupler, a second coupler, first footplate releasably coupled to the first coupler, and a second footplate releasably coupled to the second coupler. The first and second couplers each have a footplate coupling portion and a distractor connecting portion rotatably coupled to the footplate coupling portion. Rotation of the distractor connecting portions of the first and second couplers locks the first and second footplates to the first and second couplers.

In another embodiment the distractor assembly includes a distractor having a first coupler and a second coupler, a first footplate releasably coupled to the first coupler, and a second footplate releasably coupled to the second coupler. The assembly further includes an activation mechanism having an activation worm that extends into at least the first coupler. The activation mechanism defines a bore that extends therethrough. The assembly further includes a sleeve disposed about the activation mechanism and engagable with the first coupler, and a wire that extends through the bore of the activation mechanism. Disengagement of the sleeve from the first coupler releases the first footplate from the first coupler, and translation of the wire proximally pulls the distractor away from the first and second footplates.

In another embodiment the distractor assembly includes a first footplate, a second footplate, a coupler and a locking mechanism. The first footplate includes a distally extending track. The second footplate includes a central bridge portion that is configured to receive the track of the first footplate. The coupler is releasably coupled to the central bridge portion of the second footplate. The locking mechanism is configured to releasably lock the coupler to the central bridge portion of the second footplate. The locking mechanism includes a sleeve that defines threads, a nut that is threadably engaged with the threads of the sleeve, and a locking component coupled to the nut. The locking mechanism is configured to have a first position in which the locking component engages the coupler to thereby lock the coupler to the central bridge portion of the second footplate, and a second position in which the locking component is disengaged from the coupler to thereby release the coupler from the second footplate.

In another embodiment the distractor assembly includes a first footplate, a second footplate, a first coupler releasably coupled to the first footplate, and a second coupler releasably coupled to the second footplate. The first and second footplates each include a central bridge portion. The first coupler includes a spring finger that is configured to engage the central bridge portion of the first footplate. The second coupler includes a spring finger that is configured to engage the central bridge portion of the second footplate. The assembly further includes a sleeve that is configured to slide over the first and second coupler's to thereby disengage the spring fingers from the central bridge portions and release the first and second footplates from the first and second couplers.

In another embodiment the distractor assembly includes a distractor, a first footplate, a second footplate, and a double barrel pin releasably coupling the first and second footplates to the distractor. The distractor includes a first coupler, a second coupler, and a third coupler. Each of the first, second and third couplers, defines a pair of coaxial bores. The first footplate has a central bridge portion that defines a pair of coaxial bores that align with the bores of the first coupler. The second footplate has a central bridge portion that defines a pair of coaxial bores that align with the bores of the second coupler. The double barrel pin is configured to extend through the bores of the first coupler, the bores of the second coupler, the bores of the third coupler, and the bores of the first footplate, and the bores of the second footplate to thereby releasably lock the first and second footplates to the first and second couplers. Removal of the pin releases the first and second footplates from the first and second couplers.

BRIEF DESCRIPTION OF THE DRAWINGS

FIG. 1A is a top plan view of a distractor assembly according to one embodiment. The assembly includes a distractor, first and second footplates releasably coupled to the distractor, and a locking mechanism that includes a tube that when removed releases the first and second footplates from the distractor;

FIG. 1B is a side cross sectional view of the distractor assembly shown in FIG. 1A through the line 1B-1B;

FIG. 1C is a top plan view of the distractor of the distractor assembly shown in FIG. 1A;

FIG. 1D is a side elevational view of the distractor shown in FIG. 1C;

FIG. 1E is a top plan view of the first and second footplates of the distractor assembly shown in FIG. 1A;

FIG. 1F is a side elevational view of the first and second footplates shown in FIG. 1E;

FIG. 2A is a top plan view of a distractor assembly according to another embodiment. The assembly includes a first footplate, a second footplate translatably coupled to the first footplate, and an activation mechanism that is releasably coupled to the first footplate;

FIG. 2B is a side cross sectional view of the distractor assembly shown in FIG. 2A through the line 2B-2B;

FIG. 2C is an enlarged perspective view of a distal end of the activation mechanism of the distractor assembly shown in FIG. 2A;

FIG. 2D is an enlarged perspective view of the distractor assembly shown in FIG. 2A, showing the second footplate coupled to the first footplate;

FIG. 3A is a top plan view of a distractor assembly according to another embodiment. The assembly includes a first footplate, a second footplate translatably coupled to the first footplate, and an activation mechanism that is releasably coupled to the first footplate;

FIG. 3B is a side cross sectional view of the distractor assembly shown in FIG. 3A through the line 3B-3B;

FIG. 6A is a perspective view of the first coupler of the distractor assembly shown in FIG. 4;

FIG. 6B is a back elevational view of the first coupler shown in FIG. 6A;

FIG. 6C is a front elevational view of the first coupler shown in FIG. 6A;

FIG. 7A is a perspective view of the second coupler of the distractor assembly shown in FIG. 4;

FIG. 7B is a front elevational view of the second coupler shown in FIG. 7A;

FIG. 7C is a back elevational view of the second coupler shown in FIG. 7A;

FIG. 7D is a bottom plan view of the second coupler shown in FIG. 7A;

FIG. 7E is a cross sectional view of the second coupler shown in FIG. 7A through the line 7E-7E;

FIG. 8B is a perspective view of the distractor assembly shown in FIG. 8A, showing a tube portion of the locking mechanism being removed;

FIG. 8C is a bottom perspective view of the distractor assembly shown in FIG. 8A, showing the tube portion fully removed;

FIG. 9 is a top plan view of a locking mechanism according to another embodiment that may be used with a distractor assembly, the locking mechanism including a double barrel pin having a flared end;

FIG. 10A is a side elevational view of a distractor assembly according to another embodiment. The assembly including first and second footplates releasably coupled to first and second couplers by a locking mechanism that includes a double barrel pin releasably coupled to a third coupler;

FIG. 10B is a cross-sectional view of the distractor assembly shown in FIG. 10A through the line 10B-10B;

FIG. 10C is a cross-sectional view of the distractor assembly shown in FIG. 10A through the line 10C-10C;

FIG. 11A is a perspective view showing a distractor assembly according to another embodiment. The assembly including first and second couplers that are releasably coupled to first and second footplates with spring fingers having feet that engage slots defined by the footplates;

FIG. 11B is a front perspective view of the first coupler of the distractor assembly shown in FIG. 11A;

FIG. 11C is a top perspective view of a footplate used in the distractor assembly shown in FIG. 11A;

FIG. 12A is a side elevational view of a distractor assembly according to another embodiment. The assembly including first and second footplates releasably coupled to first and second couplers with a locking mechanism that includes a locking pin, and a tube that when removed releases the first and second footplates from the distractor;

FIG. 12B is a front elevational view showing the engagement of the first coupler and the first footplate of the distractor assembly shown in FIG. 12A;

FIG. 12E is a partial side perspective view of a locking portion of the locking pin of the distractor assembly shown in FIG. 12A;

FIG. 12F is a front elevational view of the locking portion shown in FIG. 12E;

FIG. 14A is top plan view of a distractor assembly according to another embodiment. The assembly including first and second footplates releasably coupled to a distractor using L-rails that are configured to compress upon the attachment of an activation mechanism;

FIG. 14B is a side elevational view of the distractor assembly shown in FIG. 14A;

FIG. 14C is a top cross-sectional view of the distractor assembly shown in FIG. 14A;

FIG. 14D is a partial side cross-sectional view of the distractor assembly shown in FIG. 14A, showing the activation extension engaging the distractor L-rail;

FIG. 14E is a front cross-sectional view of the assembly shown in FIG. 14A, showing the L-rails engaging the footplate;

FIG. 14F is a front cross-sectional view of the assembly shown in FIG. 14A, showing the L-rails disengaged from the footplate;

FIG. 15A is a top plan view of a distractor assembly according to another embodiment. The assembly including a distractor with two coupling assemblies that releasably attach the distractor to respective footplates;

FIG. 15B is a side elevational view of a third coupling attached to the distractor shown in FIG. 15A, the third coupling being configured to allow an activation mechanism to selectively rotate the first and second couplings;

FIG. 15D is a front cross-sectional view of the first coupling of the distractor assembly shown in FIG. 15A in a locked position thereby keeping the footplates attached to the assembly;

FIG. 15E is a front cross-sectional view of the first coupling of the distractor assembly shown in FIG. 15D in an unlocked position thereby allowing the footplate to be detached from the assembly;

FIG. 16A is a top plan view of a distractor assembly according to another embodiment, the assembly including a distractor attached to a footplate with a resorbable screw;

FIG. 16B is a partial view of the distractor assembly shown in FIG. 16A showing the screw;

FIG. 17A is a perspective view of a distractor assembly according to another embodiment. The assembly including a distractor having a releasable stop that selectively couples first and second footplates to the distractor;

FIG. 17B is a side cross-sectional view of the assembly shown in FIG. 17A, with the releasable stop in a closed position;

FIG. 17C is a partial side cross-sectional view of the assembly shown in FIG. 17A with the releasable stop in an open position;

FIG. 18A is a perspective view of a distractor assembly that is similar to the assembly shown in FIG. 17A except that the releasable stop is a screw that releases from the distractor body when a tube is pulled proximally;

FIG. 18B is a perspective view of the distractor assembly of FIG. 18A with the tube pulled proximally and disengaged from the screw;

FIG. 19A is a top plan view of a distractor assembly according to another embodiment. The assembly including a distractor having a distractor body that releasably holds first and second footplates to the distractor body when an activation mechanism is releasably attached to the distractor body;

FIG. 19B is a side elevational view of the distractor assembly shown in FIG. 19A;

FIG. 19D is a side cross-sectional view of the distractor assembly shown in FIG. 19A;

FIG. 20B is a cross-sectional view of the distractor assembly shown in FIG. 20A;

FIG. 21B is a side elevational view of the distractor assembly shown in FIG. 21A;

FIG. 21C is a side cross-sectional view of the distractor assembly shown in FIG. 21B;

FIG. 21D is a top plan view of the distractor of the distractor assembly shown in FIG. 21A without the footplates attached to it;

FIG. 21E is a bottom plan view of the distractor shown in FIG. 21D without the footplates attached to it;

FIG. 21F is a top plan view of the first and second footplates of the distractor assembly shown in FIG. 21A;

FIG. 21G is a side elevational view of the first and second footplates shown in FIG. 21F;

FIG. 21H is a front elevational view of the second footplate shown in FIG. 21F;

FIG. 21I is a front elevational view of the first footplate shown in FIG. 21F;

FIG. 22A is a perspective view of a distractor assembly according to another embodiment. The assembly including a distractor, first and second footplates, and a locking mechanism that includes a sleeve, a nut threadably engaged with the sleeve and a locking component configured to selectively engage a coupler and the first footplate to thereby lock the footplates to the distractor;

FIG. 22B is a cross-sectional view of the distractor assembly shown in FIG. 22A;

FIG. 22C is a front perspective view of the first footplate and coupler of the distractor assembly shown in FIG. 22A;

FIG. 22D is a front elevational view of the distractor assembly shown in FIG. 22A;

FIG. 22E is a side elevational view of the distractor assembly shown in FIG. 22A with the locking component engaged with the coupler and the first footplate;

FIG. 22F is a side elevational view of the distractor assembly shown in FIG. 22E with the locking component disengaged from the coupler and the first footplate;

DETAILED DESCRIPTION OF ILLUSTRATIVE EMBODIMENTS

Figure 1G:
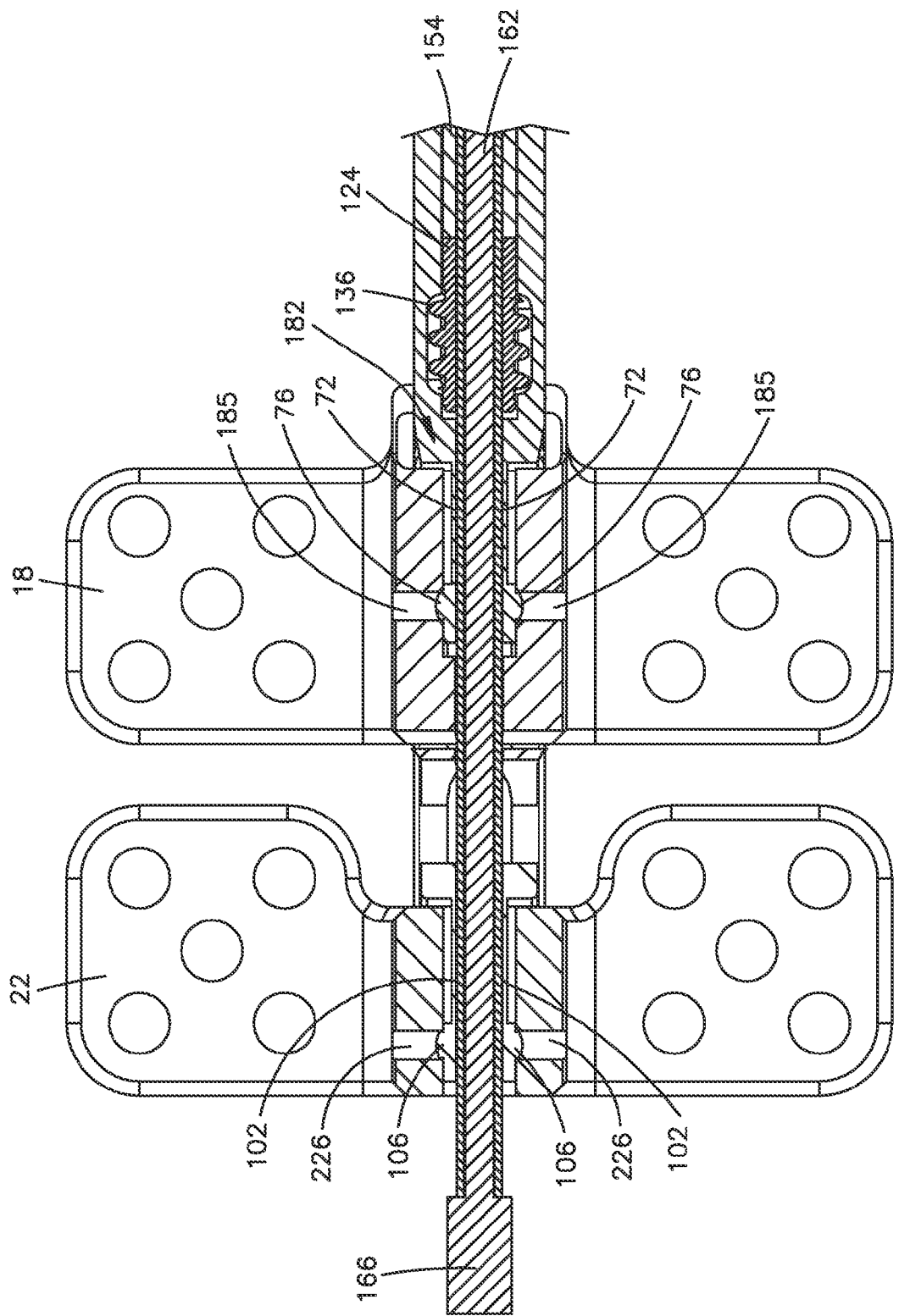
FIG. 1G is cross-sectional view of the distractor assembly of FIG. 1A, showing the locking mechanism engaging the distractor and footplates to thereby lock the footplates to the distractor.

FIGS. 1A-1G show an embodiment of a distractor assembly that is configured to correct certain craniofacial abnormalities. As shown, a distractor assembly 10 is elongate in a longitudinal direction L and includes a distal end D and a proximal end P. As shown, the distractor assembly 10 includes a distractor 14, a first footplate 18 releasably coupled to the distractor 14, and a second footplate 22 releasably coupled to the distractor 14 at a location distal to the first footplate 18. Generally, the distractor assembly 10 operates by affixing the separate footplates 18 and 22 to first and second bone segments on opposite sides of a bone gap. The bone gap can be a fracture created by a traumatic event, an osteotomy, or can be the result of debridement of a joint of two discrete bones to be joined in an arthodesis. After a waiting period, following implantation of the distractor assembly 10, one of or both of the footplates 18, 22 are translated relative to the other to thereby drive the bones on either side of the bone gap away from each other. After the desired amount of distraction is achieved, another waiting period is required to allow the new bone growth to become sufficiently consolidated. Subsequently, the distractor 14 is removed. It may be preferred that the footplates 18 and 22 are made from a resorbable material. If such materials are used, the footplates 18 and 22 can be left behind and will resorb into the bone. The footplates 18 and 22 may also be made from a flexible material.

As shown in FIGS. 1C-1D, the distractor assembly 10 includes a distractor 14 having a distractor body 34 that is releasably coupled to the first and second footplates 18, 22, and an activation mechanism 38 that is configured to translate the second footplate 22 distally relative to the first footplate 18. The distractor assembly 10 further includes a locking mechanism 42 configured to selectively couple the distractor body 34 to the first and second footplates 18, 22. As shown, the distractor 14 is elongate in the longitudinal direction L and defines a central axis A extending between the proximal and distal ends of the distractor 14. The distractor 14 is generally made from bio-compatible materials.

As best shown in FIGS. 1C and 1D, the distractor body 34 includes a first body portion 50 and a second body portion 54 that is configured to translate distally relative to the first body portion 50. As shown, the first body portion 50 is elongate in the longitudinal direction L and includes an elongate channel 58 that extends through the body portion 50 in the longitudinal direction L. The first body portion 50 therefore defines, or the channel 58, is otherwise defined by two vertically extending side walls 62. As shown in FIG. 1C, a recess or groove 66 extends along an upper end of each side wall 62 in the longitudinal direction L along a major portion of the longitudinal length of the first body portion 50. The recesses 66 are configured to receive a portion of the second body portion 54 to allow the second body portion 54 to translate relative to the first body portion 50 while at the same time remaining aligned with the first body portion 50.

Each side wall 62 further defines a spring finger 72 proximate to the distal ends of the side walls 62. As best shown in FIG. 1G, the spring fingers 72 each include an outward extending protrusion 76 at its respective end. That is, each finger 72 includes a protrusion 76 that extends laterally away from the central axis of the distractor 14. The fingers 72 are configured to spring out and engage the first footplate 18 to thereby couple the first footplate 18 to the first body portion 50. In this way, the first body portion 50 may be considered a first coupler for coupling the first footplate 18 to the distractor 14.

The second body portion 54 is also elongate in the longitudinal direction L and includes a holding portion 82 and an activation track 86 that extends proximally from the holding portion 82. The holding portion 82 includes side walls 94 that define an elongate channel 98 that extends through the holding portion 82 in the longitudinal direction L. The channel 98 of the second body portion 54 is aligned with the channel 58 of the first body portion 50. Each side wall 94 defines a spring finger 102 proximate to the distal ends of the side walls 94. As best shown in FIG. 1G, the spring fingers 102 each include an outward extending protrusion 106 at its respective end. That is, each finger 102 includes a protrusion 106 that extends laterally away from the central axis of the distractor 14. The fingers 102 are configured to spring out and engage the second footplate 22 to thereby couple the second footplate 22 to the second body portion 54. In this way, the second body portion 54 may be considered a second coupler for coupling the second footplate 22 to the distractor 14

The activation track 86 of the second body portion 54 extends out from the holding portion 82 and is configured to engage the recesses 66 of the first body portion 50. As shown in FIG. 1C, the activation track 86 defines a plurality of grooves 110 that are exposed to the channel 58 of the first body portion 50. The grooves 110 are disposed along the longitudinal length of the activation track 86 and are configured to be engaged by external threads defined by the activation mechanism 38.

As shown in FIGS. 1C and 1D, the distractor 14 includes an activation mechanism 38 for translating the second body portion 54 of the distractor 14 and thus the second footplate 22 relative to the first body portion 50. The activation mechanism 38 is elongate in the longitudinal direction L and extends into the channel 58 of the first body portion 50. As shown, the activation mechanism 38 includes an inner sleeve 120 and an activation worm 124 coupled to a distal end of the inner sleeve 120. The inner sleeve 120 includes generally a tubular body 128 defining a longitudinally elongate bore 132 that extends through the body 128. The inner sleeve 120 further defines a coupling feature 129 such as a hex at its proximal end. As shown, the proximal end of the inner sleeve 120 and thus the coupling feature 129 protrude from the proximal end of the first body portion 50. The protruding coupling feature 129 is then capable of being engaged by a driver to thereby rotate or otherwise drive the activation mechanism 38.

The activation worm 124 coupled to the distal end of the inner sleeve 120 generally includes a cylindrical body 133 defining a longitudinal bore 134 that extends therethrough, and external threads 136 about the body's external surface. The bore 134 is aligned with the bore 132 of the inner sleeve 120. The external threads 136 are configured to engage the plurality of grooves 110 of the second body portion's activation track 86. As the activation mechanism 38, and thus the activation worm 124, are rotated, the second body portion 54 is translated with respect to the first body portion 50.

As shown in FIG. 1C, the activation mechanism 38 also includes an outer sleeve 142 having a longitudinal bore 146 that extends therethrough. As shown, the outer sleeve 142 is retained within a proximal end of the channel 58 of the first body portion 50 and the inner sleeve 120 extends into and through the bore 146 of the outer sleeve 142. A portion of the outer sleeve 142 protrudes from the proximal end of the channel 58 of the first body portion 50 and defines a large diameter portion 150. The large diameter portion 150 serves to keep the percutaneous port in which the distractor 14 is inserted at a large enough size that the distractor 14 can pass through it during device removal. Both the inner sleeve 120 and the outer sleeve 142 may be made from a flexible material to allow off-axis activation of the distractor 14. Alternatively, the inner sleeve 120 and the outer sleeve 142 may have a curvature and be made of a rigid material. In such cases the inner sleeve 120 and the outer sleeve 142 may be designed by laser cut.

The distractor assembly 10 further includes a locking mechanism 42 configured to releasably couple the first and second footplates 18, 22 to the distractor 14. In particular the locking mechanism 42 is configured to lock or otherwise engage the footplates 18, 22 to the distractor 14 when in a locked position, and is configured to release or otherwise disengage the footplates 18, 22 from the distractor when in an unlocked position. As shown, the locking mechanism 42 extends through each of the bore 132 of the inner sleeve 120, the bore 134 of the activation worm 124, and the channel 98 of the second body portion 54. As shown, the locking mechanism 42 includes a tube 154 defining a longitudinally elongate bore 158 that extends therethrough, and a removal actuator 162 that extends completely through the bore 158. Preferably the tube 154 is made from a shape memory material such as nitinol, and the actuator 162 is a wire made from a flexible material such as titanium. A distal end of the actuator 162 includes an enlarged portion or ferrule 166 that has a diameter larger than the diameter of the second body portion's channel 98. A proximal end of the actuator 162 protrudes from the proximal end of the tube 154 and also includes a ferrule to thereby trap the tube 154 onto the actuator 162.

When in the locked position, the tube 154 of the locking mechanism 42 forces the fingers 72, 102 of the first and second body portions 50, 54 laterally outward such that the protrusions 76, 106 of the fingers 72, 102 engage respective footplates 18, and 22 to thereby maintain the footplates 18, 22 in engagement with the distractor 14. When in the unlocked position, the tube 154 is removed such that the fingers 72, 102 spring inward and the protrusions 76, 106 disengage from the footplates 18, 22 to thereby release or otherwise disengage the footplates 18, 22 from the distractor 14. Once the footplates are disengaged from the distractor 14 the actuator 162 may be moved (i.e. pulled) to thereby remove the distractor 14 from the footplates 18, 22 and leave the footplates 18, 22 behind to resorb into the bone.

The first and second footplates 18, 22 that are to be releasably coupled to the distractor 14 are best shown in FIGS. 1A, 1B, 1E, 1F, and 1G. As shown in FIGS. 1E and 1F, the first footplate 18 includes a pair of wings 170 that extend laterally out from a central bridge portion 174. Each wing 170 is substantially planar and includes a plurality of screw holes 178 for receiving bone screws therethrough to secure the wings 170 to bone, with wings 170 lying flat adjacent to the bone surface. 1.3 mm or 1.5 mm resorbable screws may be used to fasten the wings to bone.

The central bridge portion 174 includes a longitudinal channel 182 that is configured to receive the distractor 14 as shown in FIG. 1A. As shown, the channel 182 has a pair of opposing longitudinal sidewalls 184. Each sidewall 184 includes a lateral aperture 185 that is configured to receive a protrusion 76 of a respective spring finger 72 of the distractor first body portion 50 to thereby couple the first footplate 18 to the distractor 14, as shown in FIG. 1G. The bridge portion 174 further includes a pair of leading ratchet tabs 186 that extend proximally from a proximal surface 190 of the bridge portion 174, and a set of lagging ratchet tabs 194 that extend distally from a distal surface 198 of the bridge portion 174.

The leading ratchet tabs 186 are configured to prevent inadvertent forward movement of the second footplate 22 with respect to the first footplate 18 after the distractor 14 has been removed. As shown in FIG. 1E, each leading ratchet tab 186 extends from a lower portion of the proximal surface 190 on respective sides of the channel 182. Each leading ratchet tab 186 includes a protrusion 202 at its proximal end that protrudes inward toward a longitudinal central axis of the bridge 174. In use, the tabs 186 flex and function as a ratchet with the second footplate 22.

The lagging ratchet tabs 194 are configured to prevent reverse sliding once the second footplate 22 is translated relative to the first footplate 18. As shown, the lagging ratchet tabs 194 include a pair of upper tabs 206 that extend down at an angle from the distal surface 198 of the bridge portion 174, on respective sides of the channel 182. The lagging ratchet tabs 194 further include a pair of lower tabs 208 that extend up at an angle from the distal surface 198 of the bridge portion 174, on respective sides of the channel 182. In use, the tabs 194 flex and function as a ratchet with the second footplate 22.

Also shown in FIGS. 1E and 1F, the second footplate 22 includes a pair of wings 210 that extend laterally out from a central bridge portion 214. Each wing 210 is substantially planar and includes a plurality of screw holes 218 for receiving bone screws therethrough to secure the wings 210 to bone, with wings 210 lying flat adjacent to the bone surface. 1.3 mm or 1.5 mm resorbable screws may be used to fasten the wings 210 to bone.

The central bridge portion 214 includes a longitudinal channel 222 that is configured to receive the distractor 14 as shown in FIG. 1A. As shown, the channel 222 has a pair of opposing longitudinal sidewalls 224. Each sidewall 224 includes a lateral aperture 226 that is configured to receive a protrusion 106 of a respective spring finger 102 of the distractor second body portion 54 to thereby couple the second footplate 22 to the distractor 14, as shown in FIG. 1G.

The second footplate 22 further includes a longitudinally elongate extension 230 that extends proximally from a proximal surface 234 of the central bridge portion 214. As shown in FIG. 1F, the extension 230 extends from the central bridge portion 214 below the channel 222 and extends through the channel 182 of the first footplate's central bridge portion 174. The extension 230 defines opposing lateral sides 240, and opposing upper and bottom surfaces 244, 248 respectively. Each side 240 defines engagement features, such as teeth 252 that are configured to engage the protrusions 202 of the first footplate's leading ratchet tabs 186. The upper surface 244 and the bottom surface 248 also define engagement features, such as teeth 256 that are configured to engage the lagging ratchet tabs 194. In particular, the upper surface 244 includes two rows of teeth that are configured to engage the upper tabs 206, and the bottom surface 248 includes two rows of teeth 252 that are configured to engage the lower tabs 208.

In operation, the distractor assembly 10 is inserted and the first and second footplates 18, 22 are attached to bone on opposite sides of a bone gap. After a waiting period, following implantation of the distractor assembly 10, the second footplate 22 is translated relative to the first footplate 18 to thereby drive the bones on either side of the bone gap away from each other. The second footplate 22 is translated by rotating the activation mechanism 38. When the activation mechanism 38 is rotated, the external threads 136 of the activation worm 124 engage the angled grooves 110 of the distractor second body portion 54 to thereby drive the second body portion 54 distally away from the first body portion 50. This is done until the desired separation of the footplates 18, 22 is achieved.

At the time of distractor removal, the surgeon will cut off the proximal ferrule of the locking mechanism's actuator 162 that extends proximally from the distractor 14 and through the patient's skin with a pair of wire cutters. Once the proximal ferrule is cut, the tube 154 may be removed leaving only the actuator 162 between the body portions 50, 54 and respective footplates 18, 22, which is not of sufficient diameter to prevent deflection of fingers 72, 102. Therefore, the fingers 72, 102 are no longer engaged with the apertures 185, 226 of the first and second footplates 18, 22, and thus the first and second footplates 18, 22 are released or otherwise disengaged from the distractor 14. Then by moving (i.e. pulling) the actuator 162 to a removal position, the surgeon will remove the distractor 14 from the detachable footplates 18, 22, leaving only the detachable footplates 18, 22 still attached to the patient. Removal of the distractor 14 will be accomplished through the percutaneous port that the locking mechanism 42 extended through.

Because the detachable footplates are left behind, they preferably are made from a resorbable material, which will resorb over a 1-2 year resorption period. It is intended, however, that the detachable footplates 18, 22 can be titanium.

In another embodiment, and in reference to FIGS. 2A-2D the distractor assembly may include an activation mechanism that directly engages the second footplate to thereby translate the second footplate relative to the first footplate. As shown, a distractor assembly 310, includes a distractor 314, a first footplate 318 releasably coupled to the distractor 314, and a second footplate 322 translatably coupled to the first footplate 318. When the distractor 314 is rotated, the second footplate 322 is translated distally relative to the first footplate 318.

As shown in FIG. 2B, the distractor 314 includes an activation mechanism that is defined by a longitudinally elongate body 326. In this regard the body 326 includes a coupling member 330 at its proximal end and an activation worm 334 at its distal end. The coupling member 330 may be a hex coupling that is configured to connect to a driver so that the distractor 314 may be rotated. The activation worm 334 extending from the distal end of the body 326 includes a distally extending conical head 338 having external threads 342. The external threads 342 are configured to engage the second footplate 322 to thereby translate the second footplate distally relative to the first footplate 318. The distractor 314 further includes a sleeve 346 that is disposed about the body 326. A distal portion of the sleeve 346 defines a coupling portion that includes external threads 350 configured to engage internal threads defined by the first footplate 318 to thereby couple the distractor 314 to the first footplate 318. Proximate to the proximal end of the sleeve's threaded portion is an outwardly extending shoulder 354 that is configured to abut an outer surface of the first footplate 318 when the distractor 314 is coupled to the first footplate 318.

As shown in FIGS. 2A-2B, and 2D, the distractor assembly 310 further includes first and second footplates 318, 322 releasably coupled to the distractor 314. The first footplate 318 is stationary with respect to the distractor 314, while the second footplate 322 is translatable with respect to both the distractor 314 and the first footplate 318.

As shown, the first footplate 318 includes a pair of wings 370 that extend laterally out from a central bridge portion 374. Each wing 370 is substantially planar and includes a plurality of screw holes 378 for receiving bone screws therethrough to secure the wings 370 to bone, with wings 370 lying flat adjacent to the bone surface. 1.3 mm or 1.5 mm resorbable screws may be used to fasten the wings to bone.

The central bridge portion 374 of the first footplate 318 includes a longitudinal channel 382 that is configured to receive the distractor 314 as shown in FIG. 2B. As shown, the channel 382 extends at an angle with respect to the second footplate 322. Thus, the distractor 314 extends out from the first footplate 318 at an angle. The central bridge portion 374 further includes a second longitudinal channel 386 that extends completely through the bridge portion 374 below the first channel 382. The second channel 386 is configured to receive a portion of the second footplate 322 and is at least partially exposed to the first channel 382 so as to allow the distractor 314 to engage the second footplate 322. The bridge portion 374 further includes a lagging ratchet tab 394 that extends distally from a distal surface 398 of the bridge portion 374.

The lagging ratchet tab 394 acts as a ratchet and is configured to prevent reverse sliding once the second footplate 322 is translated relative to the first footplate 318. As shown, the lagging ratchet tab 394 extends down at an angle from the distal surface 398 of the bridge portion 374. In use, the tab 394 flexes and functions as a ratchet with the second footplate 322 as the second footplate 322 is translated relative to the first footplate 318.

As shown in FIGS. 2A-2B, the second footplate 322 includes a pair of wings 410 that extend laterally out from a central bridge portion 414. Each wing 410 is substantially planar and includes a plurality of screw holes 418 for receiving bone screws therethrough to secure the wings 410 to bone, with wings 410 lying flat adjacent to the bone surface. 1.3 mm or 1.5 mm resorbable screws may be used to fasten the wings 410 to bone.

The central bridge portion 414 of the second footplate 422 includes a longitudinally elongate extension 422 that extends proximally toward the first footplate 318. In particular, the extension 422 extends through the second channel 386 of the first footplate 318. As shown in FIG. 2D, an upper surface of the extension 422 includes a plurality of grooves 426 that are configured to engage the external threads 342 of the distractor 314. In this way the extension 422 carries a track. Additionally, the grooves 426 are configured to be engaged by the tab 394 of the first footplate 318 to prevent reverse sliding of the second footplate 322 relative to the first footplate 318.

In operation, the distractor assembly 310 is inserted and the first and second footplates 318, 322 are attached to bone on opposite sides of a bone gap. After a waiting period, following implantation of the distractor assembly 310, the second footplate 322 is translated relative to the first footplate 318 to thereby drive the bones on either side of the bone gap away from each other. The second footplate 322 is translated by rotating the body 326. When the body 326 is rotated, the external threads 342 of the activation worm 334 engage the grooves 426 of the second footplate 322 to thereby drive the second footplate 322 distally away from the first footplate 318. This is done until the desired separation of the footplates 318, 322 is achieved. At the time of distractor 314 removal the surgeon will rotate the sleeve 346 of the distractor 314 until the distractor 314 can be removed. The first and second footplates 318, 322 will remain behind and be resorbed into the bone.

In another embodiment and in reference to FIGS. 3A and 3B, the distractor assembly may be similar to the embodiment shown in FIGS. 2A-2D, but includes different structure for coupling the distractor to the footplates, and ratchet tabs that engage teeth on opposing sides of the second footplates extension. As shown, a distractor assembly 430 includes a distractor 434, a first footplate 438 releasably coupled to the distractor 434, and a second footplate 442 translatably coupled to the first footplate 438. The distractor 434 is similar to the distractor described in reference to FIGS. 2A-2D except that the distractor 434 is coupled to the first footplate 438 using deflectable tabs. Likewise, the first and second footplates 438, 442, are similar but include different structure to prevent reverse sliding of the second footplate 442 relative to the first footplate 438 after distraction has taken place.

In that regard, the distractor 434 includes an activation mechanism that is defined by a longitudinally elongate body 443 and an activation worm 444 extending distally from the body 443. A proximal end of the of worm 444 includes a deflectable finger 445 that is configured to engage the first footplate 438. The distractor 434 further includes a sleeve 446 that defines a distal coupling portion that defines internal threads 447 that engage external threads defined by a distal portion of the body 443. When the sleeve 446 is advanced distally, the finger 445 is deflected to thereby couple or otherwise lock the distractor 434 to the first footplate 438. When the sleeve is retracted proximally, the finger 445 is free to deflect and the distractor 434 may be pulled from the first footplate 438.

As shown in FIG. 3A, the first footplate 438 includes a pair of wings 450 that extend laterally out from a central bridge portion 454. The central bridge portion 454 includes a longitudinal channel 458 that is configured to receive the distractor 434 as shown in FIG. 3B. As shown, the channel 458 extends at an angle with respect to the second footplate 442. Thus, the distractor 434 extends out from the first footplate 438 at an angle. The central bridge portion 454 further includes a second longitudinal channel 462 that extends completely through the bridge portion 454 below first channel 458. The second channel 462 is configured to receive a portion of the second footplate 442 and is at least partially exposed to the first channel 458 so as to allow the distractor 434 to engage the second footplate 442. The bridge portion 454 further includes a pair of lagging ratchet tabs 468 that extend distally from a distal surface 472 of the bridge portion 454.

The lagging ratchet tabs 468 act as a ratchet and are configured to prevent reverse sliding once the second footplate 442 is translated relative to the first footplate 438. As shown, the lagging ratchet tabs extend distally from the distal surface 472 of the bridge portion 454 on either side of the second channel 462. Each tab 468 includes a protrusion 476 that extends inward toward such that the protrusions 476 of each tab 468 extends toward the other. In use, the tabs 468 flex and function as ratchets with the second footplate 442 as the second footplate 442 is translated relative to the first footplate 338.

As best shown in FIGS. 3A and 3B, the second footplate 442 includes a pair of wings 480 that extend laterally out from a central bridge portion 484. The central bridge portion 484 includes a longitudinally elongate extension 488 that extends proximally toward the first footplate 438. In particular, the extension 488 extends through the second channel 462 of the first footplate 438. An upper surface of the extension 488 includes a plurality of grooves 492 that are configured to engage the external threads of the distractor 434. In this way the extension 488 defines a track. Furthermore, lateral side surfaces of the extension 488 define teeth 494 that are configured to be engaged by the tabs 468 of the first footplate 438 to prevent reverse sliding of the second footplate 442 relative to the first footplate 438.

Figure 4:
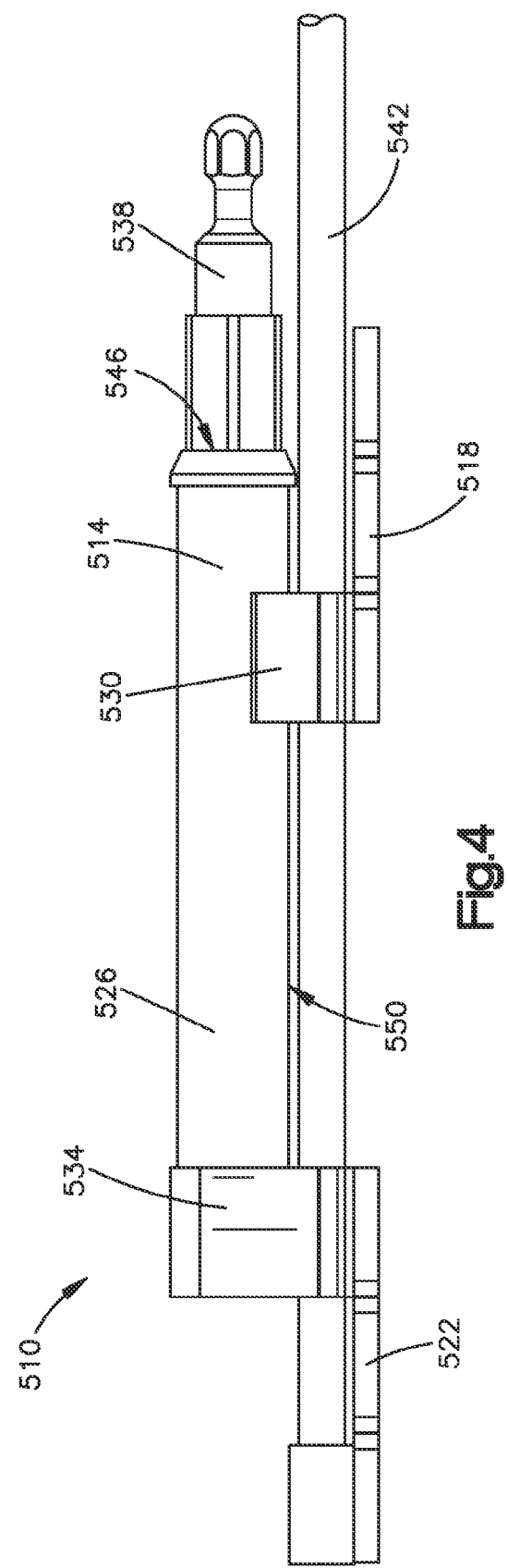
FIG. 4 is a side elevational view of a distractor assembly according to another embodiment. The assembly includes first and second footplates releasably coupled to first and second couplers by a locking mechanism including a tube that when removed releases the footplates from the couplers.

In another embodiment and in reference to FIG. 4, the distractor assembly may include couplers that engage respective footplates to releasably couple the footplates to the distractor. As shown, a distractor assembly 510 includes a distractor 514, a first footplate 518 releasably coupled to the distractor 514, and a second footplate 522 releasably coupled to the distractor 514 at a location that is distal to the first footplate 518. In the embodiment shown, the first footplate 518 is configured to translate proximally relative to the second footplate 522.

As shown in FIG. 4, the distractor 514 includes a longitudinally elongate body 526, a first coupler 530 for releasably coupling the first footplate 518 to the distractor body 526, and a second coupler 534 for releasably coupling the second footplate 522 to the distractor body 526. The distractor 514 further includes an activation mechanism 538 for translating the first footplate 518 relative to the second footplate 522.

The distractor body 526 includes a longitudinally elongate channel 546 that extends through the body 526. The channel 546 is configured to receive the activation mechanism 538 as shown in FIG. 4. The body 526 further defines a longitudinally elongate slot 550 that extends along at least a portion of the body 526. In particular, the slot 550 extends along a bottom of the body 526 and provides access to the channel 546 along its entire length. In that regard, the first coupler 530 extends through the slot 550 and into the channel 546 and is coupled to the activation mechanism 538 within the channel 546. The slot 550 therefore allows the first coupler 530 to translate along the body 526 without any interference.

Figure 5A:
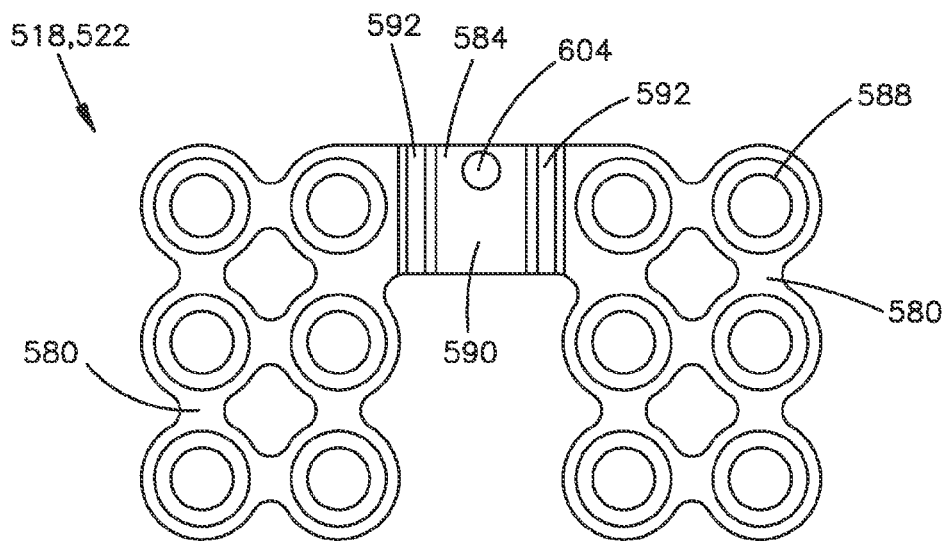
FIG. 5A is a top plan view of a footplate that can be used with the distractor assembly shown in FIG. 4.
Figure 5B:
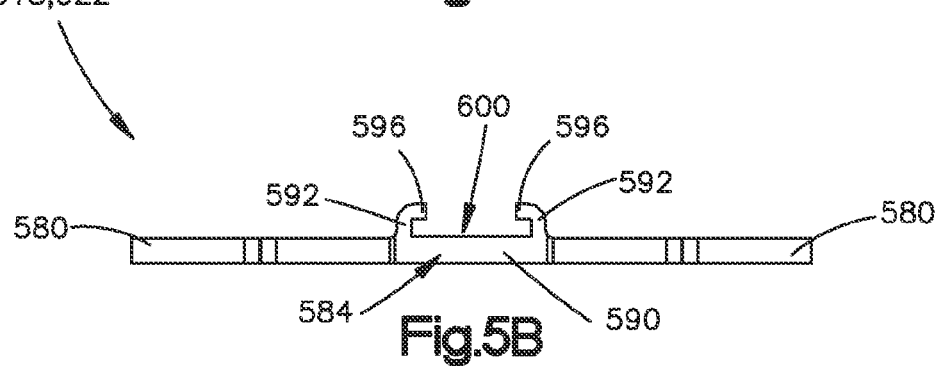
FIG. 5B. is a front elevational view of the footplate shown in FIG. 5A.
Figure 5C:
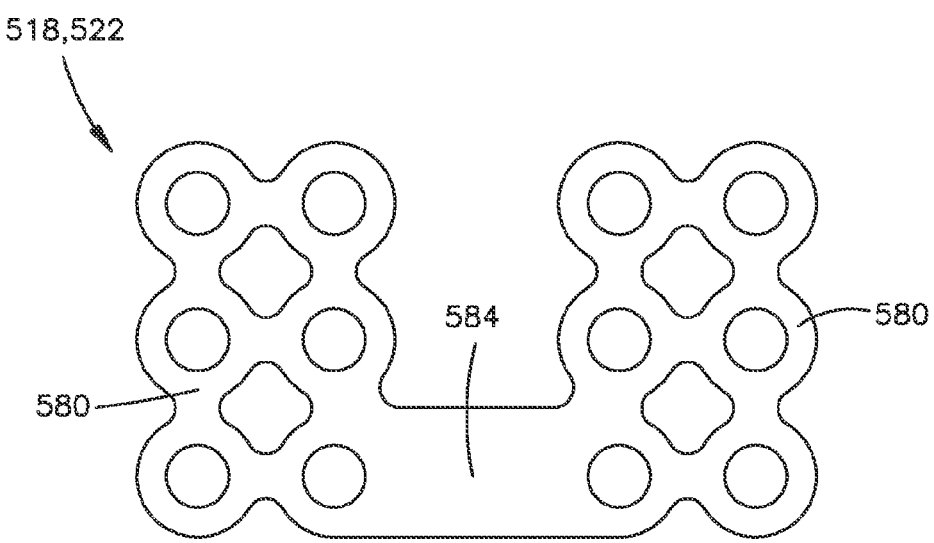
FIG. 5C is a bottom plan view of the footplate shown in FIG. 5A.

The first footplate 518 is best shown in FIGS. 5A-5C. As shown, the first footplate 518 includes a pair of wings 580 that extend out from a central bridge portion 584. Each wing 580 is substantially planar and includes a plurality of screw holes 588 for receiving bone screws therethrough to secure the wings 580 to bone, with wings 580 lying flat adjacent to the bone surface. 1.3 mm or 1.5 mm resorbable screws may be used for example to fasten the wings 580 to the bone. Central bridge portion 584 includes a body portion 590 and a pair of upwardly extending projections 592 that extend up from an upper surface of the body portion 590 and terminate at an inward extending flange 596. As shown, the projections 592 including the flanges 596 define a T-slot 600. The upper surface of the body portion 590 defines a detent 604 proximate to its distal end.

Figure 5D:
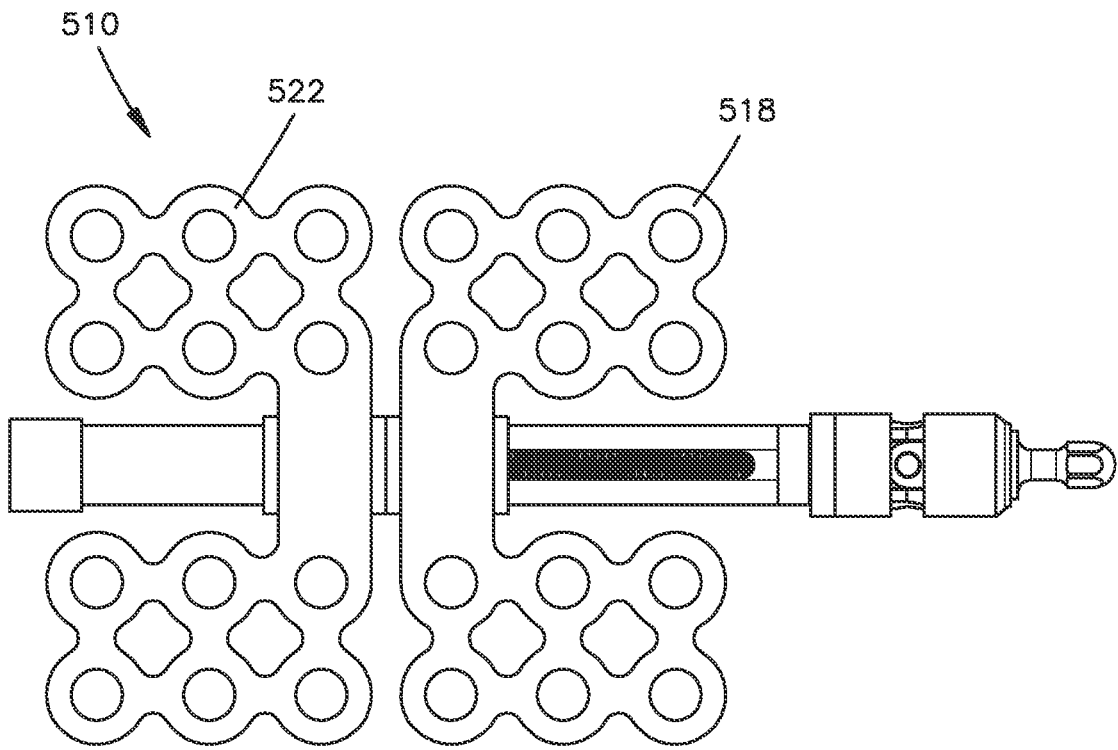
FIG. 5D is a bottom plan view of two of the footplates shown in FIG. 5A releasably coupled to respective couplers.
Figure 5E:
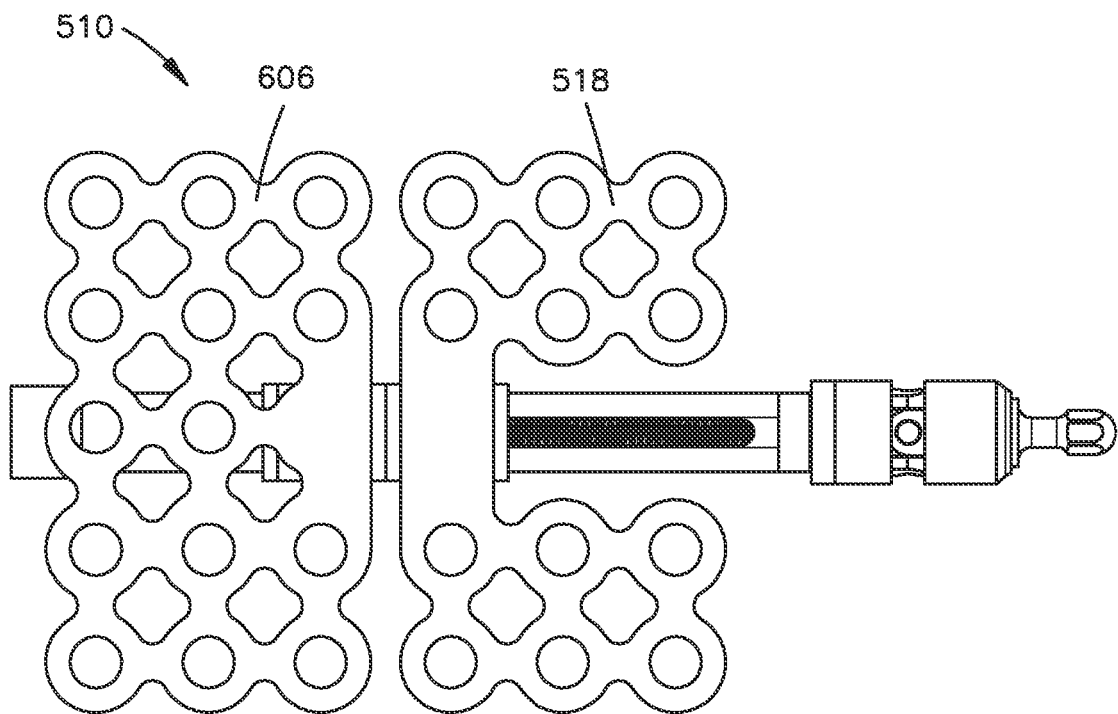
FIG. 5E is a bottom plan view of a footplate according to another embodiment, the footplate along with a footplate similar to the footplate shown in FIG. 5A releasably coupled to respective couplers.

The second footplate 522 may be identical to the first footplate shown in FIGS. 5A-5C, except that the second footplate may be oriented in an opposite direction than the first footplate 518, as shown in FIG. 5D. Alternatively, the second footplate 522 may be disposed at an end of the distractor 514 and may include a single large wing 606, as shown in FIG. 5E, as opposed to including a pair of wings.

As shown in FIGS. 4, and 6A-6E the first coupler 530 is configured to releasably couple the first footplate 518 to the distractor body 526. As shown in FIGS. 6A-6E, the first coupler 530 includes a distractor connecting portion 608 and a footplate coupling portion 612 that is connected to the distractor connecting portion 608 by a vertically oriented pedestal 616. The connecting portion 608 includes a longitudinally elongate body 620 that defines a longitudinally elongate bore 624 that extends completely through the body 620. The bore 624 includes internal threads that are configured to engage external threads defined by the activation mechanism 538. The direction of the threads defined by the bore 624 will depend on the direction the first footplate 518 is to translate.

Figure 6D:
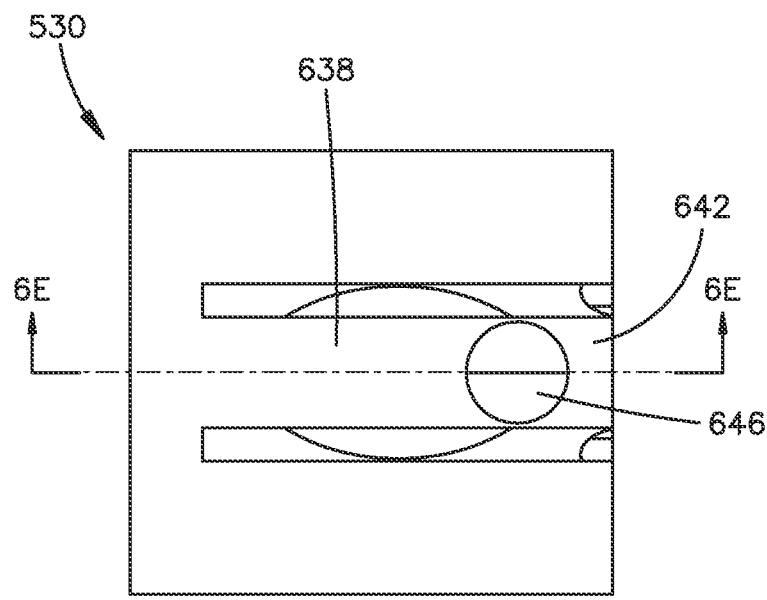
FIG. 6D is a bottom plan view of the first coupler shown in FIG. 6A.
Figure 6E:
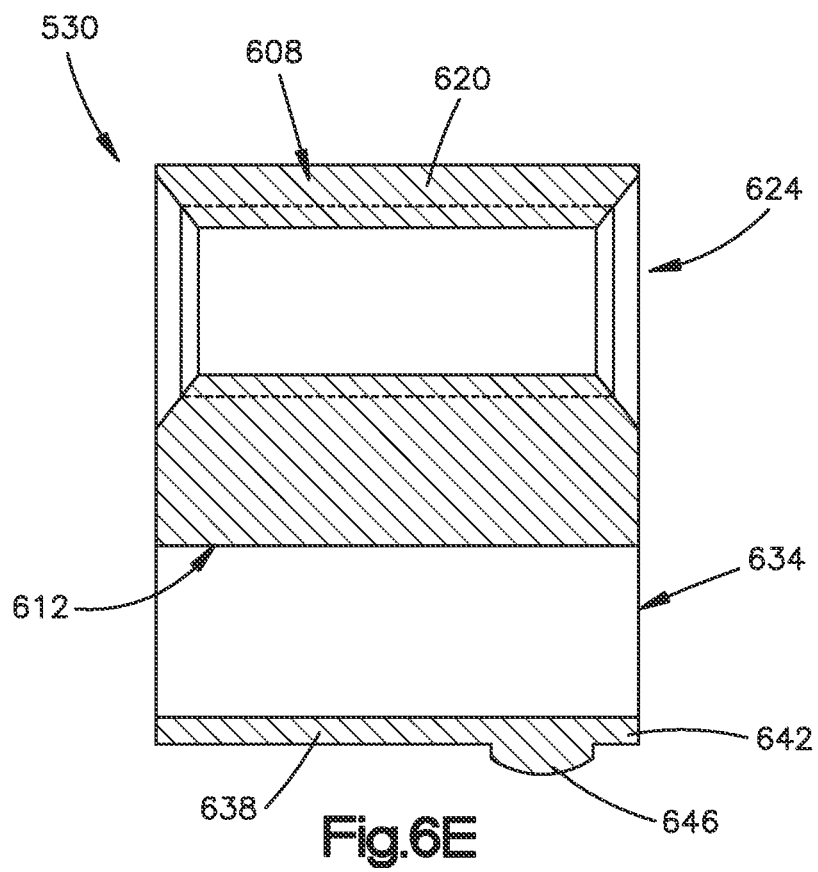
FIG. 6E is a cross sectional view of the first coupler shown in FIG. 6A through the line 6E-6E.
Figure 8A:
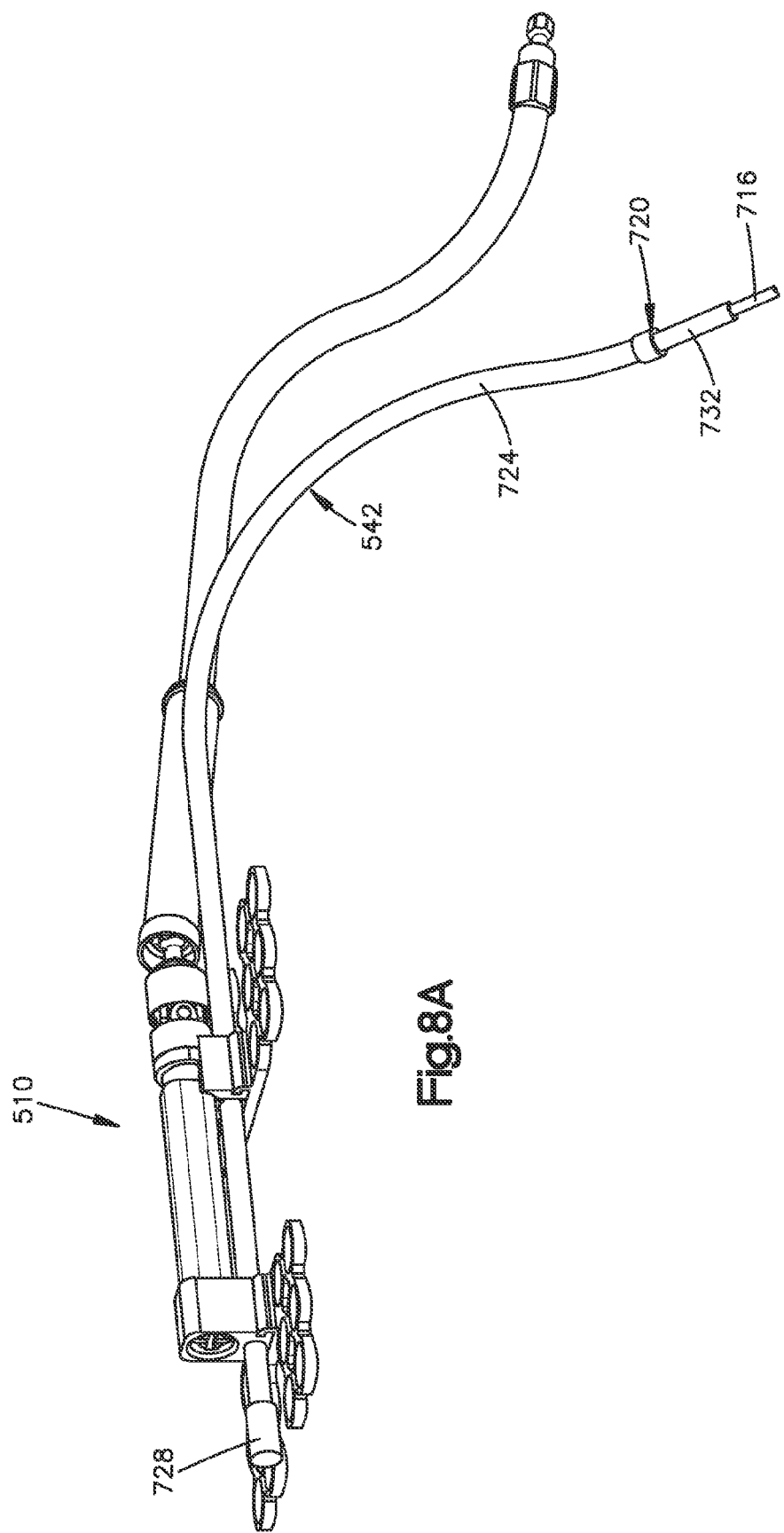
FIG. 8A is a perspective view of the distractor assembly shown in FIG. 4, showing the locking mechanism locking the footplates to the distractor.

The footplate coupling portion 612 is configured to releasably connect to the first footplate 518 shown in FIGS. 5A-5C. As shown, the footplate coupling portion 612 includes a body 630 that defines a bore 634 that extends longitudinally through the body 630. A portion of the body 630 that defines the bottom of the bore 634 defines a longitudinally extending flexible finger 638 having a free end 642 to allow the finger 638 to flex. As shown in FIG. 6D, a protrusion 646 extends down from a bottom surface of the flexible finger 638 proximate to the free end 642 of the finger 638. The protrusion 646 is configured to engage the detent 604 defined in the bridge portion 584 of the first footplate 518. The body 630 further includes opposing outwardly extending flanges 650 that extend along the longitudinal length of the body 630. As shown, the body 630 and in particular the flanges 650 define a T-shape that is configured to engage the T-slot 600 defined by the first footplate 518.

To connect the first footplate 518 to the first coupler 530, the flanges 650 of the first coupler 530 slidably engage the T-slot 600 of the footplate 518. While the first footplate 518 is being slid into place, the flexible finger 638 will flex up as the protrusion 646 that extends down from the bottom surface of the finger 638 is dragged across the upper surface of the footplates central bridge portion 584. Once the protrusion 646 of the finger 638 is positioned over the detent 604, the finger 638 will return to its normal position, thereby placing protrusion 646 into the detent 604. At this point, the first footplate 518 is loosely held to the first coupler 530. To lock, the footplate 518 to the first coupler 530 a locking mechanism, which will be discussed later, extends through the footplate coupling portion's bore 634 to thereby force the protrusion 646 into the footplate detent 604, and lock the footplate 518 to the first coupler 530.

As shown in FIGS. 4, and 7A-7E the second coupler 534 is configured to releasably couple the second footplate 522 to the distractor body 526. As shown in FIGS. 7A-7E, the second coupler 534 includes a distractor connecting portion 658 and a footplate coupling portion 662 that is connected to the distractor connecting portion 658. The connecting portion 658 includes a body 670 that defines a cavity 674 that extends longitudinally into the body 670. The cavity 674 is shown to be rectangular in shape, and is configured to receive the body 526 of the distractor 514. The back of cavity 674 includes a stop plate 682 having a bore 686 therethrough. The stop plate 682 allows the second coupling 534 to be securely placed onto the end of the distractor body 526. In this configuration, the second coupler 534, and thus the second footplate 522, are configured to remain stationary while the first coupler 530, and thus the first footplate 518 translate.

The footplate coupling portion 662 is configured to releasably connect to the second footplate 522. As shown, the footplate coupling portion 662 includes a body 690 that defines a bore 694 that extends longitudinally through the body 690. A portion of the body 690 that defines the bottom of the bore 694 defines a longitudinally extending flexible finger 698 having a free end 702 to allow the finger 698 to flex. As shown in FIG. 7D, a protrusion 706 extends down from a bottom surface of the flexible finger 698 proximate to the free end 702 of the finger 698. The protrusion 706 is configured to engage a detent defined by the second footplate, similar to the detent 604 defined in the bridge portion 584 of the first footplate 518. The body 690 further includes opposing outwardly extending flanges 710 that extend along the longitudinal length of the body 690. As shown, the body 690 and in particular the flanges 710 define a T-shape that is configured to engage a T-slot of the second footplate 522, similar to the T-slot 600 defined by the first footplate 518.

To connect the second footplate 522 to the second coupler 534, the flanges 710 of the second coupler 534 slidably engage the T-slot of the footplate 522. While the second footplate 522 is being slid into place, the flexible finger 698 will flex up as the protrusion 706 that extends down from the bottom surface of the finger 698 is dragged across the upper surface of the footplates central bridge portion. Once the protrusion 706 of the finger 698 is positioned over the detent, the finger 698 will return to its normal position, thereby placing protrusion 706 into the detent of the second footplate 522. At this point, the second footplate 522 is loosely held to the second coupler 534. To lock, the footplate 522 to the second coupler 534 the locking mechanism, which will be discussed later, extends through the footplate coupling portion's bore 694 to thereby force the protrusion 706 into the second footplate's detent, and lock the footplate 522 to the second coupler 534.

As best shown in FIGS. 4, and 8A-8C the distractor assembly 510 further includes a locking mechanism 542 that is movable between a locked position in which the first and second footplates 518, 522 are maintained in engagement with the first and second couplers 530, 534, and an unlocked position in which the footplates 518, 522 are disengaged from the first and second couplers 530, 534. As shown, the locking mechanism 542 extends through the bores 634, 694 of the first and second couplers 530, 534, and includes a tube 724 that defines a longitudinally elongate bore 720, and a removal actuator 716 that extends through the bore 720. Preferably, the tube 724 is made from a shape memory material, such as nitinol, and the actuator 716 is a wire made from a flexible material such as titanium. A distal end of the actuator 716 protrudes from the tube 724 and includes an enlarged portion or ferrule 728 that has a diameter larger than the diameter of the second coupler's bore 694. A proximal end of the actuator 716 also protrudes from the tube 724 and includes a an enlarged portion or ferrule 732 to thereby trap the tube 724 between the two ferrules 728, 732.

When in the locked position, the tube 724 of the locking mechanism 542 forces the fingers 638, 698 of the first and second couplers 530, 534 outward such that the protrusions 646, 706 of the fingers 638, 698 engage respective detents of the footplates 518, 522, to thereby maintain the footplates 518, 522 in engagement with the distractor 514. In other words, because the diameter of the tube 724 is large enough to prevent deflection of the fingers 638, 698, the protrusions 646, 706 of the fingers 638, 698 respectively, will remain in the detents of their respective footplates 518, 522, thereby preventing the distractor 514 from separating from the footplates 518, 522. In use the locking mechanism 542 lies passively in the soft tissue similar to the activation mechanism 538.

At the time of distractor removal, the surgeon will cut off the proximal ferrule 732 that extends through the patient's skin with a pair of wire cutters, allowing the tube 724 to be separated from the actuator 716 as shown in FIG. 8B. This will then leave only the actuator 716 between the first and second couplers 530, 534 and detachable footplates 518, 522, which is not of sufficient diameter to prevent deflection of the fingers 638, 698. Then by moving (i.e. pulling) the actuator 716 to the unlocked position, the surgeon will disengage the first and second couplers 530, 534 from the detachable footplates 518, 522, leaving only the detachable footplates 518, 522 still attached to the patient. Removal of the distractor 514 will be accomplished through the percutaneous port that the locking mechanism 542 extends through.

Although it is preferred that the locking mechanism 542 extends from the patient, it can also be attached so that locking mechanism 542 does not extend outside the patient. This prevents the patient from being able to access the locking mechanism 542 to cut it off prematurely, (which may cause the distractor to separate) but the surgeon would have to make an incision to gain access to it, at the time of removal. This may be preferred for some surgeons who are willing to sacrifice another incision for greater security against premature separation.

FIG. 9 shows another locking mechanism that may be used to couple the first and second footplates to the first and second couplers. As shown, a locking mechanism 800 may be a solid pin 804 that extends beyond the overall length of the distractor and remains buried under the soft tissue. The end of this solid pin 804 may include a flare 808 so as to prevent separation under normal loads. At the time of distractor removal, the surgeon would have to create an incision to re-expose the distractor but would only have to access the pin 804 and pull it out, thereby allowing the distractor to separate from the footplates. This may allow for easier access to the bone screws in the area of the temporomandibular joint during mandible distraction.

In another embodiment and in reference to FIGS. 10A-10D the distractor assembly may include a double barrel pin that releasably couples the footplates to the distractor. As shown, the distractor assembly 810 includes a distractor 814, a first footplate 818 releasably coupled to the distractor 814, and a second footplate 822 releasably coupled to the distractor 814 at a location distal to the first footplate 818. In the embodiment shown, the first footplate 818 is configured to translate relative to the second footplate 822.

As shown in FIG. 10A, the distractor 814 includes a longitudinally elongate body 826, a first coupler 830 for releasably coupling the first footplate 818 to the distractor body 826, a second coupler 834 for releasably coupling the second footplate 822 to the distractor body 826, and a third coupler 840 for securing a locking mechanism 842 that is configured to lock the first and second footplates 818, 822 to the first and second couplers 830, 834. As shown, the locking mechanism 842 is a double barreled pin 846 having two longitudinally elongate barrels 848. The distractor 814 further includes an activation mechanism disposed within a channel of the body 826 for translating the first footplate 818 relative to the second footplate 822.

Figure 10D:
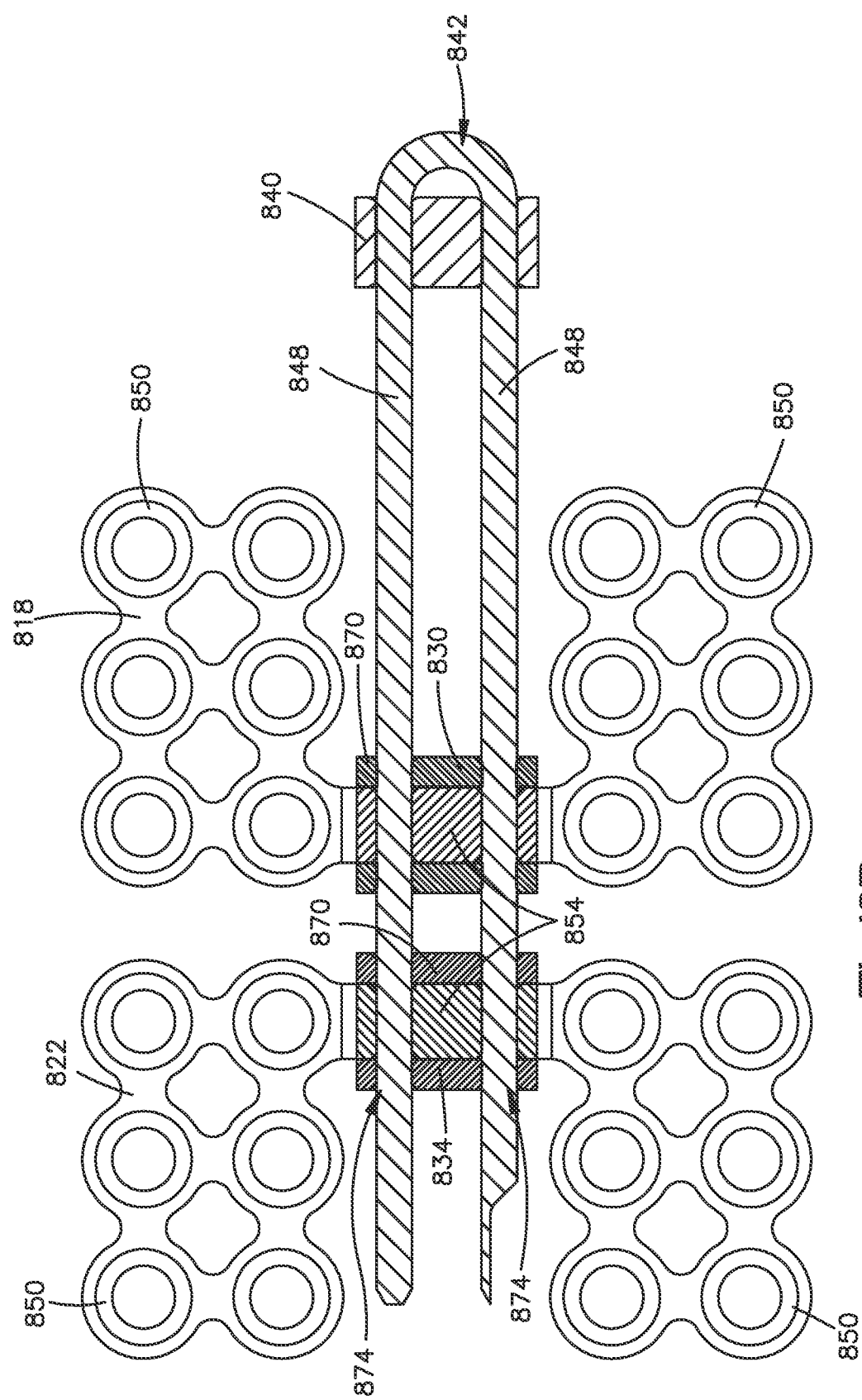
FIG. 10D is a cross-sectional view of the assembly shown in FIG. 10A showing the double barrel pin engaging the footplates and the couplers.

As shown in FIGS. 10B and 10D, the first and second footplates 818, 822 each includes a pair of wings 850 that extend out from a central bridge portion 854. Central bridge portion 854 includes a body portion 860 that defines a pair of longitudinally extending bores 864 that extend completely through the body portion 860. The bores 864 of each of the first and second footplates 818, 822 are configured to receive the locking mechanism 842.

As shown in FIGS. 10A, 10B, and 10D, the first and second couplers 830, 834 are configured to releasably couple the first and second footplates 818, 822 to the distractor body 826. As shown, the first and second couplers 830, 834 each includes a respective distractor connecting portion 868 (that are similar to the distractor connecting portions 608, and 658, respectively, of the embodiment shown in FIGS. 4-8C) and a footplate coupling portion 862 connected to the distractor connecting portion 868. Because the distractor connecting portions 868 are similar to those described in relation to FIGS. 4-8C, the first coupler 830, and thus the first footplate 818 is configured to translate relative to the second coupler 834.

The footplate coupling portions 862 are configured to releasably connect to the first and second footplates 818, 822. As shown, the footplate coupling portions 862 each includes a body 870 that defines a pair of bores 874 that extend longitudinally through the body 870. The bores 874 of both the first and second couplers 830, 834 are configured to receive the locking mechanism 842. To couple the footplates to the distractor, the bores 864 of the first and second footplates 818, 822 are aligned with the bores 874 of the first and second couplers 830, 834, and the pin 846 is inserted, such that a barrel 848 of the pin 846 passes through respective bores of the footplates 818, 822 and couplers 830, 834.

As shown in FIGS. 10A and 10C, the third coupler 840 is attached to the distractor body 826 at a location proximal from both the first and second couplers 830, 834. As shown, in FIG. 10C, the third coupler 840 includes a distractor connecting portion 878 for connecting the third coupler 840 to the distractor body 826, and a coupling portion 882 for connecting the third coupler to the locking mechanism 842 (i.e. the pin 846). In that regard, the coupling portion 882 also defines a pair of bores 886 that are configured to receive respective barrels 848 of the pin 846. Preferably the bores 886 are slightly smaller in diameter than the bores 864, 874 to create a greater frictional fit between the third coupling 840 and the pin 846 than the fit between the bores 864, 874 and the pin 846. The tight fit ensures that the pin 846 will not be removed unintentionally.

To decouple or otherwise release the footplates 818, 822 from the distractor 814, the pin 846 is removed by pulling the end of the pin 846 and disengaging the pin 846 from out of couplers 830, 834, and 840. A wire (not shown) may be attached to the pin 846 and brought through the percutaneous incision to allow the locking mechanism 846 to be disengaged from outside the patient. This may require, however a wire-wrapping procedure that prevents the distractor from being able to be disengaged prematurely. Accordingly, the third coupler 840 may also include bores 890 that extend through the coupling portion 882 above the bores 886. The wire may extend through the bores 890.

In another embodiment and in reference to FIGS. 11A-11C the distractor assembly may include couplers that have a locking mechanism incorporated into them. As shown in FIG. 11A, a distractor assembly 910 includes a distractor 914, a first footplate 918 releasably coupled to the distractor 914, and a second footplate 922 releasably coupled to the distractor 914 at a location distal to the first footplate 918. In the embodiment shown, the first footplate 918 is configured to translate with respect to the second footplate 922.

As shown in FIG. 11A, the distractor 914 includes a body 926, a first coupling 930 translatably attached to the body 926, and a second coupler 934 attached to a distal portion of the body 926. The distractor 914 further includes an activation mechanism that extends into a channel of the body 926. The activation mechanism is configured to drive or otherwise translate the first coupler 930, and thus, the first footplate 918.

As best shown in FIG. 11B the first and second couplers 930, 934 each include a body 942 that defines a longitudinally extending bore or channel 946 that extends through the body 942. The channel 946 is configured to receive the distractor 914. The body 942 further defines a recess 948 that extends up into a bottom surface of the body 942. The recess 948 is configured to receive a raised geometry defined by the footplates. Each coupler 930, 934 also includes a pair of spring fingers 950 that extend down from a top portion of the body 942. As shown, a spring finger 950 extends from each lateral side of the body 942. The bottom end of each spring finger 950 includes a laterally outward extending foot 954. The spring fingers 950 and in particular the feet 954 are configured to engage the first and second footplates 918, 922.

As best shown in FIG. 11C, each footplate 918, 922 includes a pair of wings 958 extending outward from a central bridge portion 962. As shown, the central bridge portion 962 defines a raised geometry or protrusion 966 and a pair of slots 970. As shown, a slot 970 is defined on each lateral side of the raised protrusion 966. The raised protrusion 966 is configured to engage the recess 948 of one of the couplers 930, 934 to thereby prevent rotation of the footplates. The slots 970 are configured to receive a foot 954 of a respective spring finger 950 to thereby lock the footplate to the coupler. In this way, the spring fingers 950 may be considered a locking mechanism. Assembly is accomplished by the surgeon snapping the couplers 930, 934 onto the detachable footplates 918, 922 and then attaching the couplers 930, 934 to the distractor body 926.

Removal of the distractor 914 may be accomplished by making a second incision to access the spring fingers 950. It is expected that the spring fingers 950 will be able to be squeezed with standard forceps available in the operating room, to thereby release the couplers 930, 934 from the footplates 918, 922. While a second incision is made, it may be possible to remove couplers 930, 934 without making a second incision. For example, a slidable tube may be used that is slid over the couplers 930, 934 to force the fingers 950 laterally in and release the couplers 930, 934 from the footplates 918, 922.

Figure 12C:
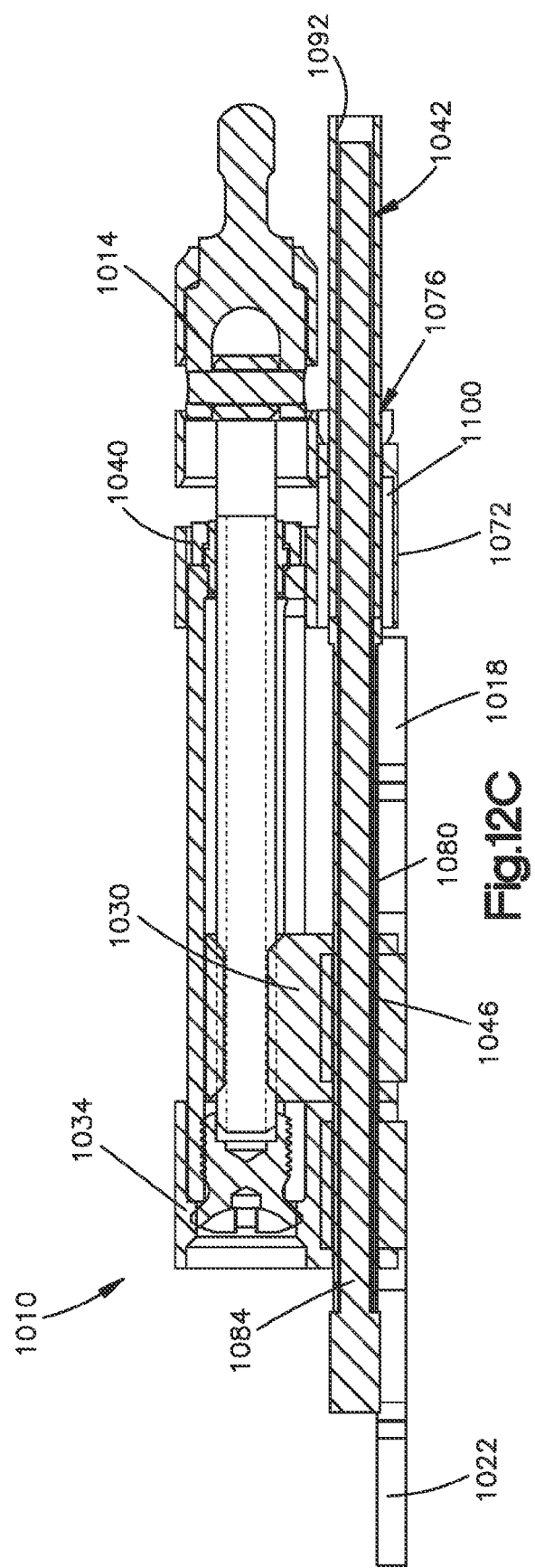
FIG. 12C is a side cross-sectional view of the distractor assembly shown in FIG. 12A.

In another embodiment and in reference to FIGS. 12A-12E the distractor assembly may include a hollow locking pin to lock the footplates to the distractor. As shown in FIG. 12A, a distractor assembly 1010 includes a distractor 1014, a first footplate 1018 releasably coupled to the distractor 1014, and a second footplate 1022 releasably coupled to the distractor 1014. In the embodiment shown, the first footplate 1018 is configured to translate relative to the second footplate 1022.

As shown in FIG. 12A, the distractor 1014 includes a longitudinally elongate distractor body 1026, a first coupler 1030 translatably attached to the body 1026, a second coupler 1034 attached to the body 1026 at a location distal to the first coupler 1030, and a third coupler 1040 attached to the body 1026 at a location proximal to the first coupler 1030. The first coupler is configured to releasably couple the first footplate 1018 to the distractor body 1026, while the second coupler is configured to releasably couple the second footplate 1022 to the distractor body 1026. The distractor 1014 further includes an activation mechanism for driving the first coupler 1030, and thus, the first footplate 1018 in a proximal direction. A locking mechanism 1042 is configured to lock the first and second footplates 1018, 1022 to the first and second couplers 1030, 1034.

As shown in FIG. 12B, each footplate 1018, 1022 includes a central bridge portion 1046 having a raised body 1050. As shown, the raised body 1050 defines a bore 1054 that extends longitudinally through the body 1050. Also shown in FIG. 12B, the first and second couplers 1030, 1034 each include a footplate coupling portion 1058 that defines a bore 1062 that extends longitudinally through the coupling portion 1058. The coupling portion 1058 further defines a recess 1066 that extends into a bottom surface of the coupling portion 1058. The recess 1066 is configured to receive the raised body 1050 of one of the footplates such that the bore 1054 of the raised body 1050 aligns with the bore 1062 of the coupling portion 1058. The aligned bores 1054, 1062 are configured to receive the locking mechanism 1042.

Figure 12D:
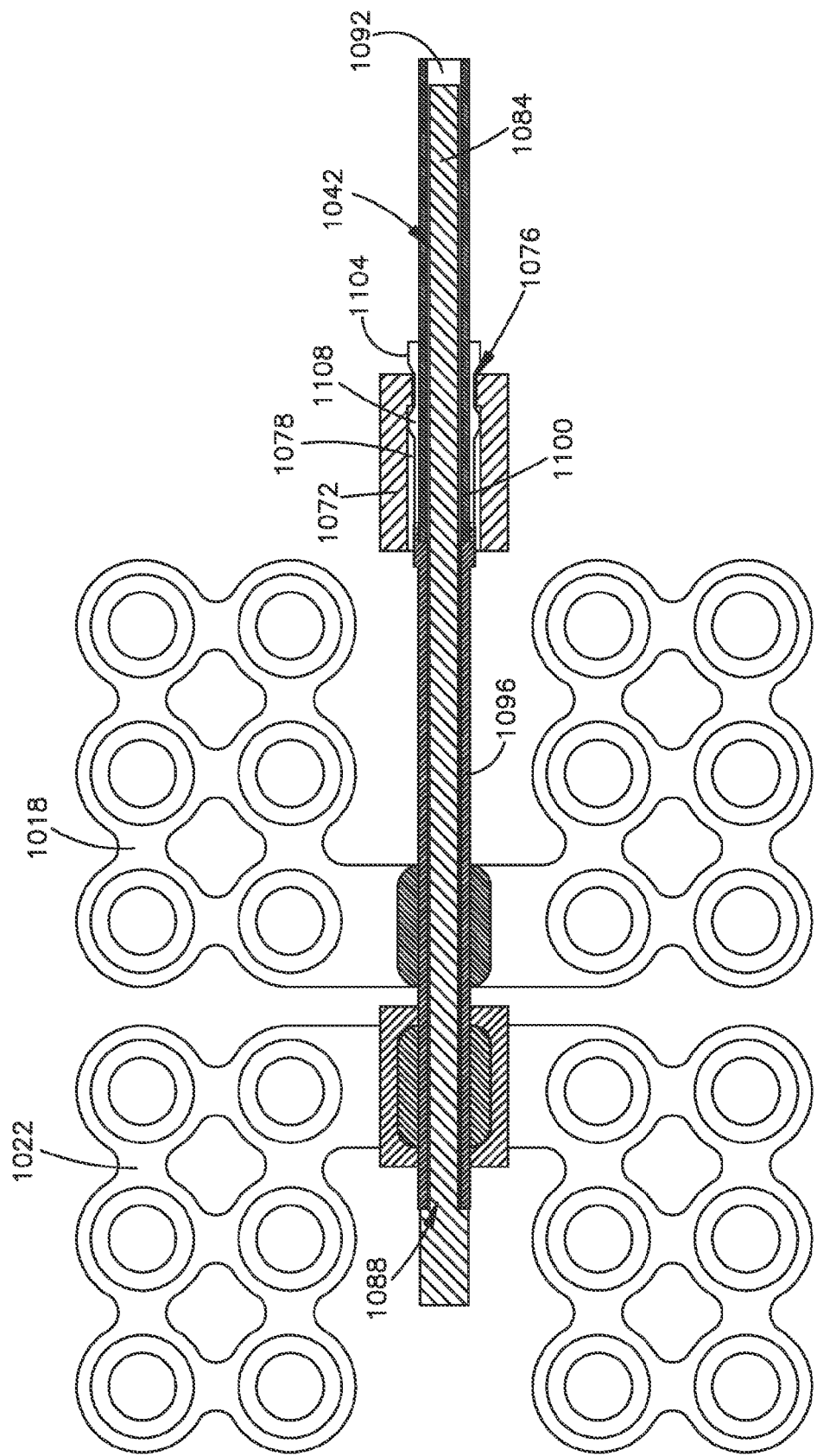
FIG. 12D is a top cross-sectional view of the distractor assembly shown in FIG. 12A.

Referring to FIGS. 12A, 12C, and 12D, the third coupler 1040 includes a coupling portion 1072 that defines a bore 1076 that extends longitudinally through the coupling portion 1072. As shown in FIG. 12D, the bore 1076 is slightly larger than the bores 1054, 1062 and defines a recess 1078 extending into the surface of the bore 1076. As shown in FIG. 12C, the bore 1076 is configured to receive the locking mechanism 1042.

As shown in FIGS. 12C-12E, the locking mechanism 1042 includes a longitudinally elongate locking pin 1080, a removal actuator 1084 that extends through a longitudinally extending bore 1088 of the locking pin 1080, and a tube 1092 configured to lock the locking pin 1080 to the third coupler 1040. As shown, the locking pin 1080 includes a coupling portion 1096 that extends through the bores 1062 of the first and second couplers 1030, 1034, and a locking portion 1100 that is disposed within the bore 1076 of the third coupler 1040. As shown in FIGS. 12E-12F, the locking portion 1100 includes four deflectable fingers 1104 that deflect to pass into the bore 1076 of the third coupler 1040. Each finger 1104 includes a protrusion 1108 that is configured to engage the recess 1078 defined in the bore 1076 of the third coupler 1040.

The locking mechanism 1042 is assembled by passing the locking pin 1080 through the bores 1054, 1062 of the footplates 1018, 1022, and the first and second couplers 1030, 1034, and also through the bore 1076 of the third coupler 1040. Once placed, the coupling portion 1096 of the locking pin 1080 should be disposed within the bores 1054, 1062 of the footplates and first and second couplers, while the locking portion 1100 of the locking pin 1080 is disposed within the bore 1076 of the third coupler 1040. At this point, the actuator 1084 is disposed within the bore 1088 of the locking pin 1080. The tube 1092 may then be slid over the actuator 1084 and into the bore 1088 of the locking pin 1080 to thereby prevent the fingers 1104 from deflecting. At this point the tube 1092 is in a locked position. When the tube 1092 is inserted the protrusions 1108 of the fingers 1104 should engage the recess 1078 of the third coupler's bore 1076. This captures the locking pin 1080 within the third coupler 1040 and secures the footplates 1018, 1022 to the distractor 1014. The tube 1092, which is preferably made from nitinol, is then axially retained on the actuator 1084 by crimping on a ferrule.

Removal of the distractor 1014 is accomplished by cutting off the ferrule outside the patient's body, removing the tube 1092 to an unlocked position, and then moving (i.e. pulling) the actuator 1084 which in turn pulls the locking pin 1080 out of the third coupler 1040. This then allows the couplers 1030, 1034 to separate from their respective footplates 1018, 1022. The distractor 1014 may then be removed leaving the footplates behind.

Figure 13A:
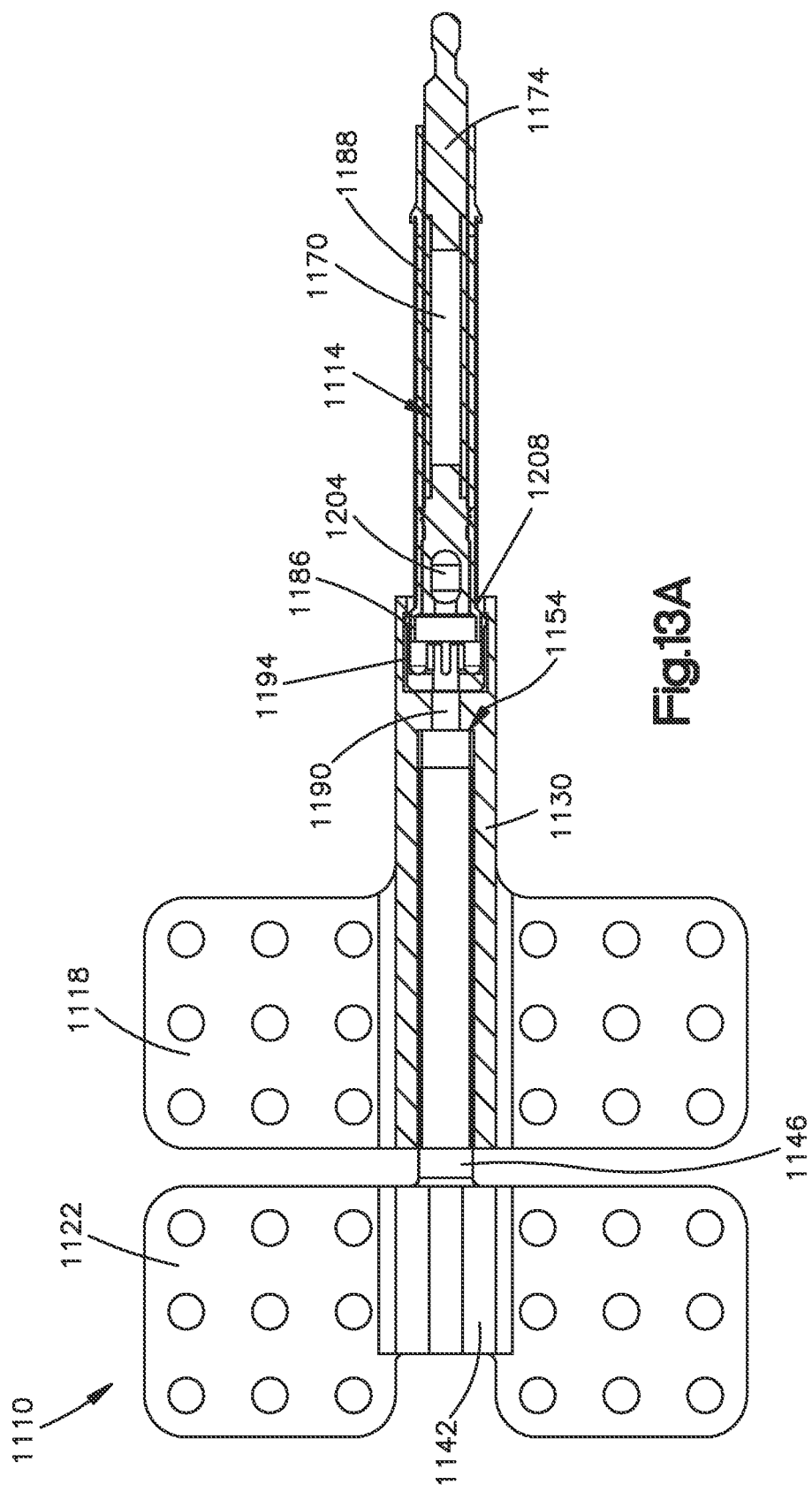
FIG. 13A is a top cross-sectional view of a distractor assembly according to another embodiment. The assembly including a first footplate, a second footplate translatably coupled to the first footplate, and an activation mechanism that is releasably coupled to the first footplate.
Figure 13B:
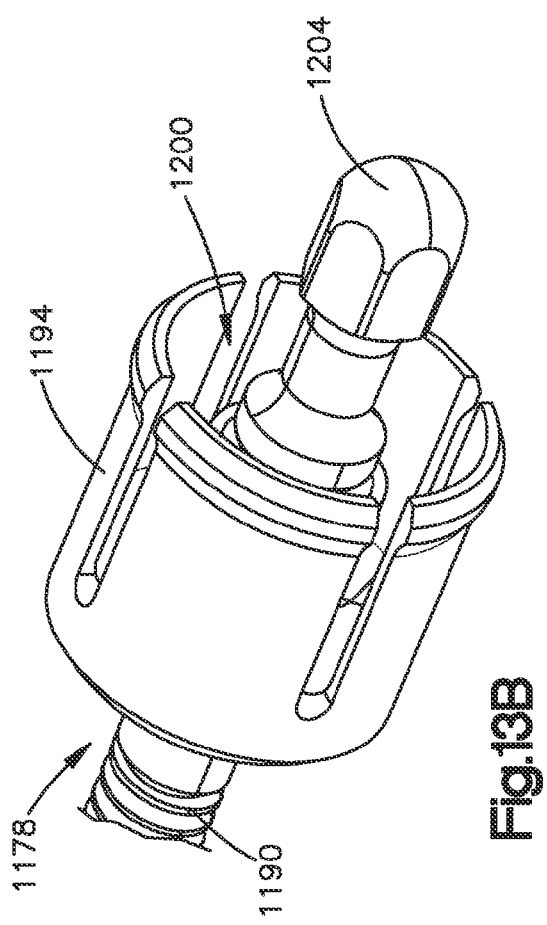
FIG. 13B is a front perspective view of a retaining clip of a worm gear of the activation mechanism shown in FIG. 13A.
Figure 13C:
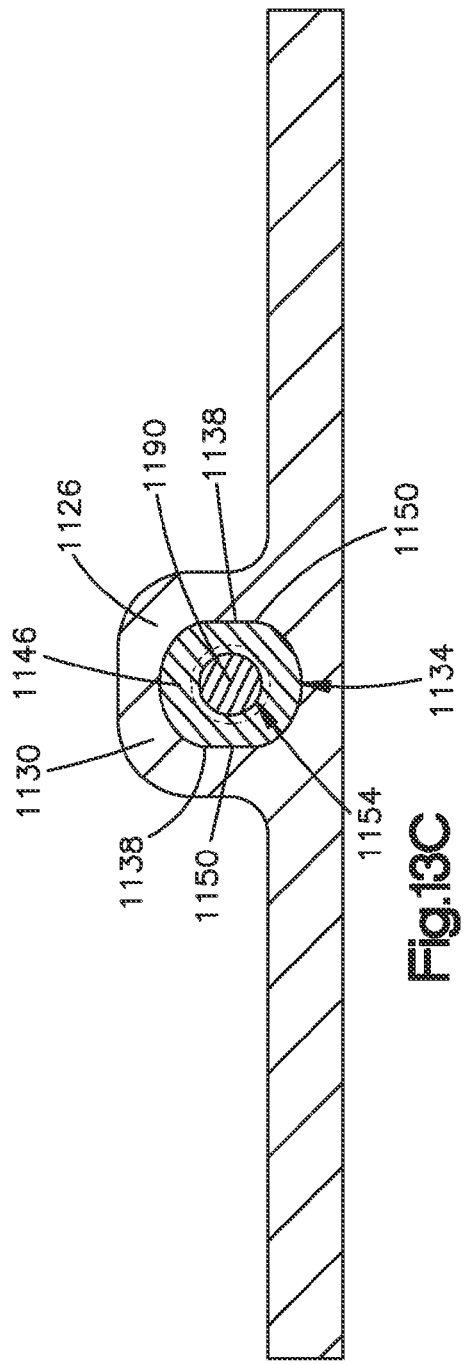
FIG. 13C is a front cross-sectional view of the distractor assembly shown in FIG. 12A through the line 13C-13C.

In another embodiment and in reference to FIGS. 13A-13C, the distractor assembly may include first and second footplates that are integrated, and an activation mechanism that is releasably attached to the first footplate. As shown in FIG. 13A, a distractor assembly 1110 includes a distractor 1114, a first footplate 1118 coupled to the distractor 1114, and a second footplate 1122 translatably coupled to the first footplate 1118. In the embodiment shown, the second footplate 1122 translates relative to the first footplate 1118.

As shown in FIGS. 13A and 13C, the first footplate 1118 includes a central bridge portion 1126 having a longitudinally elongate body 1130. As shown, the body 1130 defines a bore 1134 that extends longitudinally through the body 1130. The bore 1134 is shaped to have at least one flat surface 1138. In the embodiment shown, the bore 1134 has two opposing flat surfaces 1138. In this regard, the bore 1134 is said to have a keyed geometry.

The second footplate 1122 includes a central bridge portion 1142 having an extension 1146 that extends proximally toward the first footplate 1118. As shown in FIG. 13C, the extension 1146 is shaped to fit the keyed geometry of the first footplate's bore 1134. In that regard, the extension 1146 has two flat sides 1150 and is configured to be received by the bore 1134 of the first footplate 1118. The extension 1146 further defines a bore 1154 that extends longitudinally through the extension 1146. The internal surface of bore 1154 defines threads. In this way the extension 1146 is considered to carry a threaded track.

As shown in FIG. 13A, the distractor 1114 includes an activation mechanism 1170 having a longitudinally elongate body 1174 connected to an activation worm 1178 by a coupling mechanism 1186 at the body's 1174 distal end. The activation mechanism 1170 further includes a sleeve 1188 that is translatable along the body 1174. The sleeve 1188 is configured to lock the activation mechanism 1170 to the first footplate 1118 when the sleeve 1188 is in a distal first position, and release the activation mechanism 1170 when the sleeve 1188 is in a proximal second position.

As shown in FIGS. 13A and 13B, the activation worm 1178 includes a longitudinally elongate distraction screw 1190 that extends into the bore 1154 of the second footplate 1122. The distraction screw 1190 includes external threads that engage the internal threads of the bore 1154. The activation worm 1178 further includes spring fingers 1194 at its proximal end that define a cavity 1200. Extending from the cavity 1200 is a coupling mechanism 1204 that is configured to engage the coupling mechanism 1186 of the body 1174.

In use the activation worm 1178 is inserted into the bore 1154 of the second footplate 1122. When the body 1174 is inserted into the cavity 1200 and coupled to the activation worm 1178, and the sleeve 1188 is in its distal position, the spring fingers 1194 of the activation worm 1178 engage a flange 1208 of the bore 1134 of the first footplate 1118 and are prevented from deflecting inwardly. Because the spring fingers 1194 are prevented from deflecting inwardly the activation worm 1178 is locked to the first footplate 1118.

Activation of the distractor 1114 to thereby translate the second footplate 1122 relative to the first footplate 1118 is accomplished by application of torque to the body 1174 and in turn to the activation worm 1178. The second footplate 1122 translates because of the keyed relationship between the second footplate's extension 1146 and the first footplate's bore 1134. Because the extension 1146 cannot rotate due to the keyed configuration, it translates along the distraction screw 1190. While it is preferred that the keyed geometry be inherent to the shape of the extension 1146 and the bore 1134, it is perceived that a pin/slot combination could work as well.

Removal of the distractor 1114 is accomplished by sliding the sleeve 1188 proximally and removing the body 1174 from the activation worm 1178 so that the fingers 1194 of the activation worm 1178 are no longer prevented from deflecting. At this point, the activation worm 1178 may be pulled out through the percutaneous incision leaving the remainder of the assembly behind.

In another embodiment and in reference to FIG. 14A-14F the distractor assembly may include an activation mechanism that is used as a locking component between the detachable footplates and the distractor body. As shown, a distractor assembly 1210 includes a distractor 1214, a first footplate 1218 releasably coupled to the distractor 1214 and a second footplate 1222 releasably coupled to the distractor 1214 at a location distal to the first footplate 1218. In the embodiment shown, both the first and second footplates 1218, 1222 translate relative to each other.

As shown in FIGS. 14E and 14F each footplate 1218, 1222 includes a central bridge portion 1226 having two spaced apart upwardly extending protrusions 1230. The upper ends of each protrusion 1230 define an outward extending flange 1234. The protrusions 1230 are spaced such that a recess 1238 is defined between the two protrusions 1230.

As shown in FIGS. 14A-14F, the distractor 1214 includes a longitudinally extending outer housing 1242, a longitudinally extending body 1246 rigidly coupled to an interior of the housing 1242, and a barrel 1250 for each footplate 1218, 1222 translatably disposed within a bore 1254 of the body 1246. As shown, the bore 1254 is elongate in the longitudinal direction and defines a slot 1258 through a bottom portion of body 1246 and extending longitudinally along the bore 1254. Each barrel 1250 includes an engagement portion 1262 disposed within the bore 1254 and a protrusion 1266 that extends down from the engagement portion 1262 and through the slot 1258. Each protrusion 1266 is configured to engage the recess 1238 of a respective footplate 1218, 1222. Each engagement portion 1262 defines a longitudinally elongate bore 1270 that extends through the engagement portion 1262 in the longitudinal direction. The bores 1270 each define internal threads. The direction of the threads will determine the direction the barrels 1250 translate.

The distractor further includes an activation mechanism having an activation worm 1274 that extends through the bores 1270 of the barrels 1250. The activation worm 1274 includes external threads for engaging the internal threads of the barrel bores 1270. The activation worm 1274 also includes a coupling member 1278 extending from its proximal end. As the activation worm 1274 is rotated, the barrels 1250 will translate in their respective directions.

The distractor 1214 further includes a pair of L-rails 1280 that are disposed within the housing 1242 and around the body 1246. The L-rails 1280 are elongate in the longitudinal direction and each include an inwardly extending flange 1284. The flange 1284 of the L-rails 1280 are configured to engage flanges 1234 of the footplates 1218, 1222 to thereby lock the footplates 1218, 1222 to the distractor 1214. The L-rails 1280 are biased apart by a spring 1292 contained within the housing 1242. Each L-rail 1280 includes a ramp 1300 at its proximal end. As shown, the ramps 1300 angle laterally outwards as they extend distally in the longitudinal direction.

As shown in FIGS. 14C and 14D, the activation mechanism further includes a body 1304 for rotating the activation worm 1274. The body 1304 longitudinally elongate and includes a coupling member 1312 at its distal end. The coupling member 1312 is defined as a cavity 1316 that is configured to receive the coupling member 1278 of the activation worm 1274. As shown, the cavity 1316 defines an outer rim 1320 configured to ride up the ramps 1300 of the L-rails 1280.

As best shown in FIG. 14D, the activation mechanism body 1304 gets inserted onto the activation worm 1274. As the activation mechanism body 1304 is being placed, the rim 1320 of the activation mechanism body 1304 rides up the ramps 1300 of the L-rails 1280 to thereby compress the L-rails 1280 together. When the L-rails 1280 are compressed the footplates 1218, 1222 are coupled to the distractor 1214, as shown in FIG. 14E. Once coupled, the activation mechanism body 1304 may be rotated to thereby translate the barrels 1250, and thus, the footplates 1218, 1222 with respect to each other.

Once distraction is complete, removal is accomplished by loosening the activation mechanism body 1304 from the activation worm 1274, which causes the L-rails 1280 to release from the footplates 1218, 1222, as shown in FIG. 14F. This in turn allows the distractor 1214 to be removed through the percutaneous incision.

In another embodiment and in reference to FIGS. 15A-15E the distractor assembly may include couplers similar to those described in reference to FIGS. 6A-7E, except that rotation of an activation mechanism locks the footplates to the couplers. As shown, a distractor assembly 1410 includes a distractor 1414, a first footplate 1418 releasably coupled to the distractor 1414, and a second footplate 1422 releasably coupled to the distractor 1414 at a location distal to the first footplate 1418. The footplates 1418, 1422 are similar to the footplates described in reference to FIGS. 5A-5C.

The distractor 1414 includes a longitudinally elongate body 1426, a first coupler 1430 attached to the body 1426, and a second coupler 1434 attached to the body 1426. The first coupler 1430 is configured to releasably couple the first footplate 1418 to the body 1426, and the second coupler 1434 is configured to releasably couple the second footplate 1422 to the body 1426.

Figure 15C:
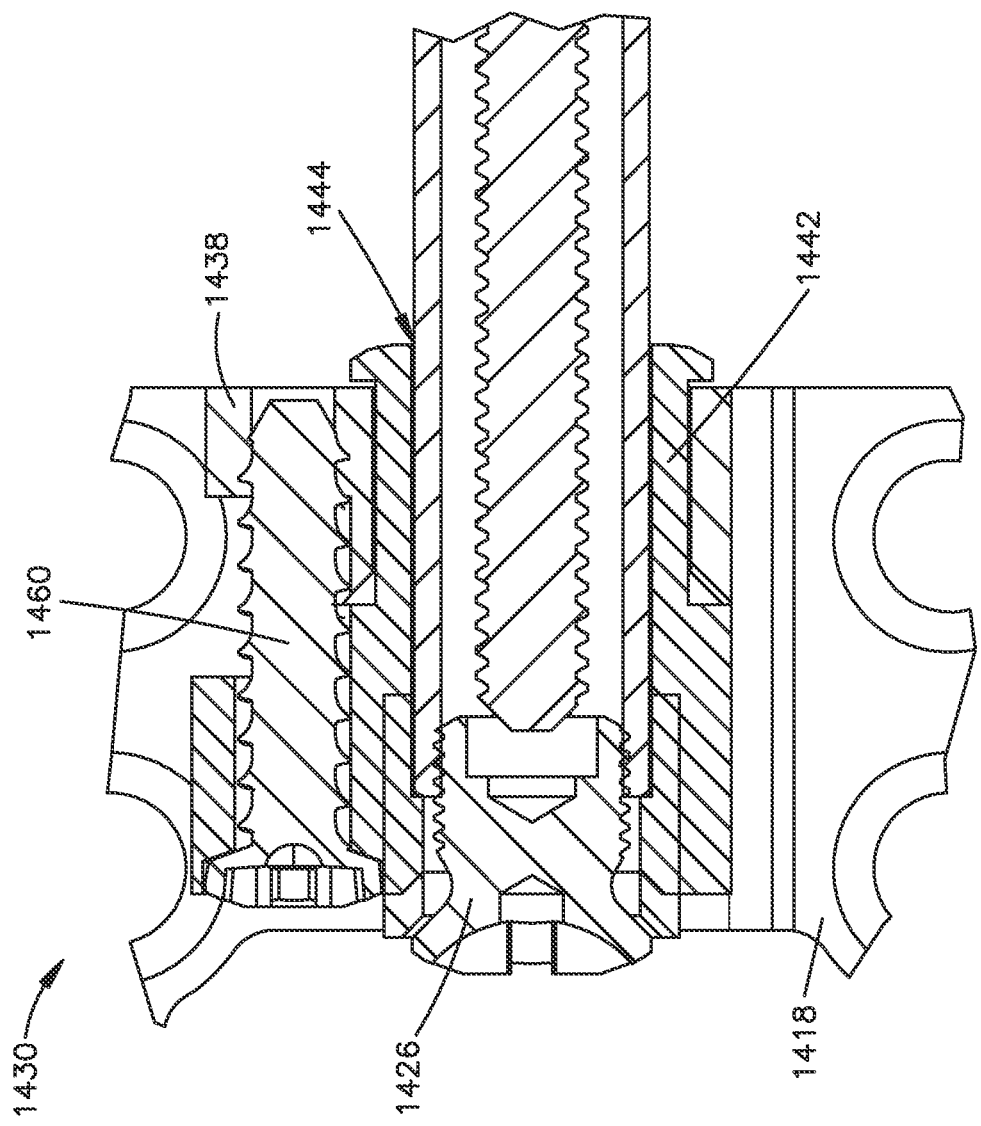
FIG. 15C is a side cross-sectional view of the first coupling shown in FIG. 15A including a screw lock that prevents unwanted rotation of the distractor.

As shown in FIGS. 15C-15E, each coupler 1430, 1434 includes footplate coupling portion 1438 and a distractor connecting portion 1442 rotatably coupled to the footplate coupling portion 1438. The distractor connecting portion 1442 defines a bore 1444 that is configured to receive the body 1426. As shown, the bore 1444 and the body 1426 are keyed such that when the body 1426 is rotated, the distractor connecting portion 1442 rotates. The distractor coupling portion 1442 further defines an outwardly extending bulge 1445 and an inwardly extending recess 1446 that are each configured to interact with the footplate coupling portion 1438.

The footplate coupling portion 1438 defines a longitudinally extending flexible finger 1448 having a free end 1450 to allow the finger 1448 to flex. As shown in FIG. 15D, a protrusion 1454 extends down from a bottom surface of the flexible finger 1448 proximate to the free end 1450 of the finger 1448. The protrusion 1454 is configured to engage a detent defined in a footplate, such as the detent 604 defined in the bridge portion 584 of the footplate 518. The footplate coupling portion 1438 further includes opposing outwardly extending flanges 1458 that define a T-shape configured to engage the T-slot defined by a footplate, such as T-slot 600 defined by the footplate 518. While the footplate coupling portion 1438 is being slid into place, the flexible finger 1448 will flex up as the protrusion 1454 that extends down from the bottom surface of the finger 1448 is dragged across the upper surface of the footplates central bridge. Once the protrusion 1454 is positioned over the detent 604, the finger 1448 will return to its normal position, thereby placing the protrusion 1454 into the detent 604. At this point, the footplates are loosely held to the respective coupler 1430, 1434.

To lock the footplates 1418, 1422 to the first and second couplers 1430, 1434 the body 1426 is rotated 180 degrees to thereby rotate the distractor coupling portions 1442 of the first and second couplers 1430, 1434 to position the respective bulges 1445 over the fingers 1448 of the footplate coupling portions 1438. The bulges 1445 will prevent the fingers 1448 from deflecting thereby locking the footplates 1418, 1422 to the distractor 1414. Conversely, to unlock the footplates 1418, 1422 the body 1426 is rotated 180 degrees so that the recesses 1446 are positioned over their respective fingers 1448 to thereby allow the fingers 1448 to flex. To prevent this rotation from happening until removal, a resorbable screw 1460 is used to lock the distractor coupling portions 1442 and their respective footplate coupling portions 1438 together.

As shown in FIGS. 15A and 15B, the distractor 1414 further includes an activation mechanism 1470 configured to be coupled to the body 1426 with a third coupler 1474. The coupler 1474 allows the activation mechanism 1470 to translate one of the footplates 1418, 1422 with respect to the other. When the distraction is complete, radial teeth 1478 defined at the distal end of the activation mechanism 1470 are configured to engage radial teeth 1482 defined by the proximal end of the body 1426. This allows transmission of the torque to the body 1426 so that the resorbable screws 1460 may be broken to thereby rotate the distractor coupling portions 1442 and allow the fingers 1448 to flex. The distractor 1414 is then pulled out of the detachable footplates 1418, 1422 and through the percutaneous incision, leaving the footplates 1418, 1422 behind in the patient.

In another embodiment and in reference to FIGS. 16A and 16B the distractor assembly may include resorbable screws to lock the footplates to the distractor. As shown, a distractor assembly 1510 includes a distractor 1514, a first footplate 1518 releasably coupled to the distractor 1514, and a second footplate 1522 releasably coupled to the distractor 1514 at a location distal to the first footplate 1518. A resorbable screw 1526 is used to lock at least the second footplate 1522 to the distractor 1514. Over the course of distraction and consolidation, the resorbable screw 1526 will become weak enough to allow the distractor 1514 to be disengaged from the footplate 1522 by the normal technique described.

In another embodiment and in reference to FIGS. 17A-17E, the distractor assembly may include a releasable stop that when released allows the footplates to decouple from the distractor. As shown, a distractor assembly 1610 includes a distractor 1614, a first footplate 1618 releasably coupled to the distractor 1614, and a second footplate 1622 releasably coupled to the distractor 1614 at a location that is distal to the first footplate 1618. In the embodiment shown, the first footplate 1618 is configured to translate proximally relative to the second footplate 1622.

As shown in FIGS. 17A and 17B, the distractor 1614 includes a longitudinally elongate body 1626, and an activation mechanism 1630 that extends into a longitudinally elongate channel 1634 defined by the distractor body 1626. As best shown in FIGS. 17B and 17C, the distractor body 1626 defines an opening 1638 at its distal end and a releasable stop 1642 that selectively opens and closes the distal opening 1638. The distractor body 1626 further defines a longitudinally elongate slot 1646 that extends along a bottom portion of the distractor body 1626. The slot 1646 is configured to receive and contain the first and second footplates 1618, 1622.

In the illustrated embodiment, the releasable stop 1642 is a hinged door 1650 that is pivotable about a pivot 1654. As shown, the door 1650 defines a locking mechanism receiving bore 1658 that is configured to receive a locking mechanism. The bore 1658 is parallel to the longitudinal direction when the door 1650 is at some angle relative to the longitudinal direction. For example, as shown in FIG. 17B, when the door 1650 is angled toward the proximal end of the distractor the bore 1658 is parallel to the longitudinal direction and capable of receiving the locking mechanism.

The activation mechanism 1630 includes a flexible activation extension 1662 and an activation worm 1666 that is configured to engage at least one of the footplates to thereby translate at least one of the footplates relative to the other upon activation of the activation worm 1666.

Figure 17D:
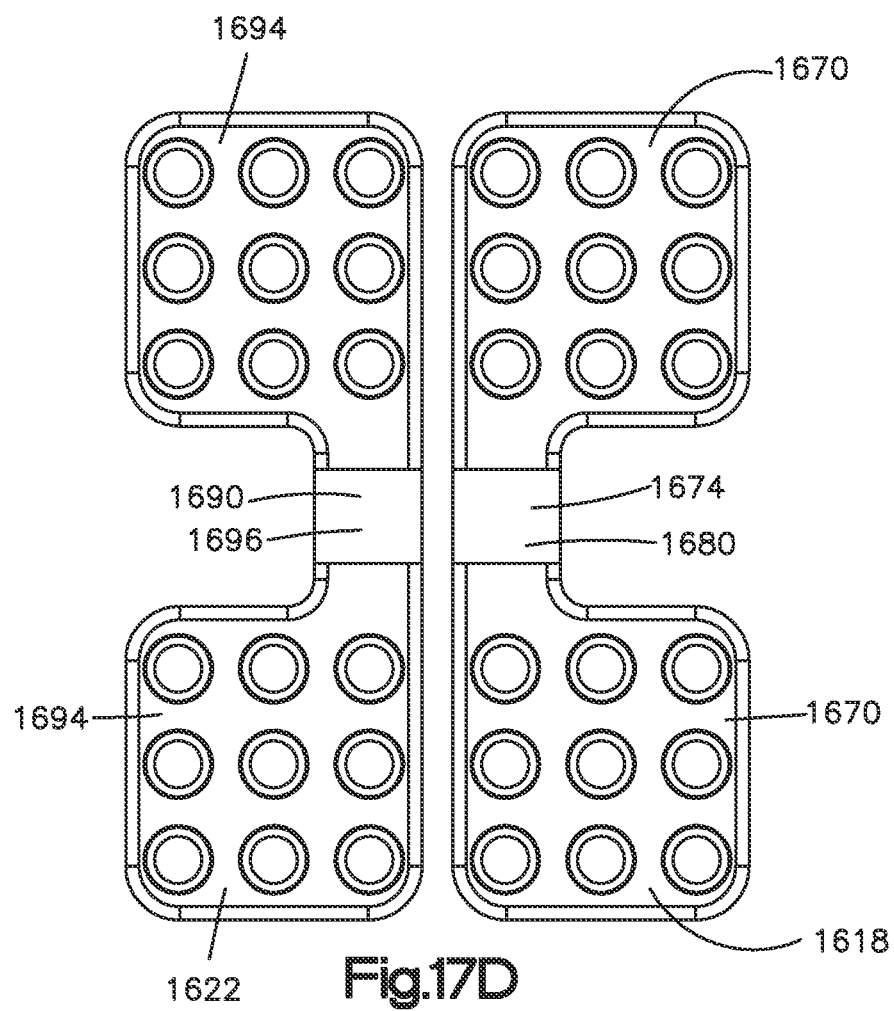
FIG. 17D is a top plan view of the first and second footplates of the assembly shown in FIG. 17A.
Figure 17E:
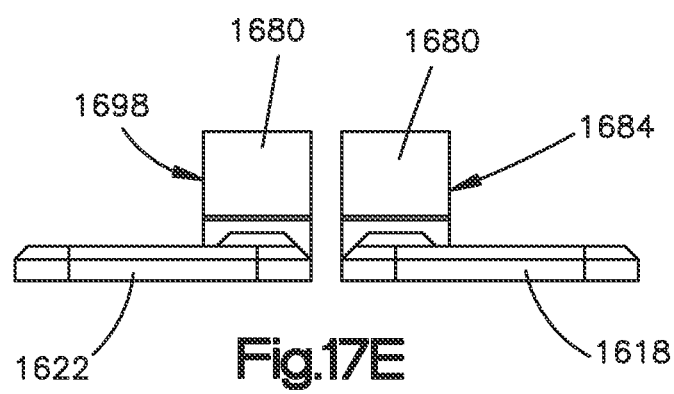
FIG. 17E is a side elevational view of the first and second footplates shown in FIG. 17D.

As shown in FIGS. 17D-17E, the first footplate 1618 includes a pair of wings 1670 that extend out from a central bridge portion 1674. Each wing 1670 is substantially planar and includes a plurality of screw holes for receiving bone screws therethrough to secure the wings 1670 to bone, with wings 1670 positioned adjacent to the bone surface. 1.3 mm or 1.5 mm resorbable screws may be used for example to fasten the wings 1670 to the bone. Central bridge portion 1674 includes a body portion 1680 that defines a longitudinally extending channel 1684. The channel 1684 defines internal threads that are configured to engage threads defined by the activation mechanism 1630 such that when the activation mechanism 1630 is rotated the first footplate will translate proximally. As shown in FIG. 17C, the body portion 1680 extends through the slot 1646 and is contained within the channel 1634 of the body 1626. In this way the distractor 1614 is considered to have a first coupler.

Similarly the second footplate 1622 includes a central bridge portion 1690 and a wing 1694 extending laterally out from opposing sides of the central bridge portion 1690. As shown, the central bridge portion 1690 includes a body portion 1696 that defines a longitudinally extending channel 1698 that is configured to receive the locking mechanism.

As best shown in FIGS. 17B and 17C, the distractor assembly 1610 further includes a locking mechanism 1700 that is configured to extend through a bore of the activation mechanism through the bores of the first and second footplates 1618, 1622 and through the bore 1658 of the hinged door 1650. In the illustrated embodiment, the locking mechanism 1700 is a tube 1704 that is made of a flexible material such as nitinol.

In operation, when the distractor 1614 is ready to be removed, the tube 1704 is pulled proximally so as to disengage the tube 1704 from the bore 1658 of the hinged door 1650. Once disengaged, the door 1650 is free to swing freely and reverse turning of the activation mechanism 1630 will translate the first and second footplates 1618, 1622 out of the distal opening 1638 of the distractor body 1626.

In another embodiment and in reference to FIGS. 18A-18B, the distractor assembly may include a releasable stop that defines a screw. As shown, the releasable stop may be a screw 1706 that is held in place by the tube 1704. The screw 1706 includes fingers 1708 that can deflect and be held securely in openings in the side of the distractor body 1626. When the tube 1704 is removed, the removable screw can disengage from the body 1626 and fall out. To make sure that the screw is not left within the patient, the side of the screw 1706 is secured to the distractor body 1626 by a wire or cable that allows the screw 1706 to follow the distract body 1626 as it is pulled out of the patient.

In another embodiment and in reference to FIGS. 19A-19G the distractor assembly may include a distractor having additional features. As shown, a distractor assembly 1710 includes a distractor 1714, a first footplate 1718 releasably attached to the distractor 1714 and a second footplate 1722 releasably attached to the distractor 1714 distal to the first footplate 1718 and configured to translate relative to the first footplate 1718.

As shown, the distractor 1714 includes a first body portion 1726 configured to releasably hold the first footplate 1718 and a second body portion 1730 configured to releasably hold the second footplate 1722. In the illustrated embodiment the second body portion 1730 and thus the second footplate 1722 is configured to translate relative to the first body portion 1726.

As shown, the first body portion 1726 includes a body 1734, and a track 1738 that extends distally from the body 1734. The body 1734 defines a longitudinal channel 1740 that extends therethrough, a pair of grooves 1742 defined in the exterior surfaces of the sidewalls that define the channel 1740, and a ball detent 1742 that extends down toward the first footplate 1718. The ball detent 1742 is configured to engage the first footplate 1718 to thereby secure the first footplate 1718 to the first body portion 1726. In this way, the first body portion 1726 may be considered a first coupler for coupling the first footplate 1718 to the distractor 1714.

The second body portion 1730 includes a body 1746 that defines a channel 1750 extending therethrough and a pair of grooves 1742 that are defined in the exterior surfaces of the sidewalls that define the channel 1740. The body 1746 further includes a pair of spring fingers 1754 each defined in lateral walls of the channel 1750. The spring fingers 1754 are configured to spring laterally inwards when the footplate is placed onto the second body portion 1730 and then engage the footplate 1722 when the footplate is properly positioned. To prevent the spring fingers 1754 from springing in, the second body portion 1730 includes a lock component 1758 disposed within the channel 1750 that blocks the fingers 1754. A spring 1760 prevents the lock component 1758 from deflecting proximally unless it intentionally pulled. When its time to remove the distractor 1714, the lock component 1758 is pulled proximally thereby allowing the spring fingers 1754 to flex inward again and allowing the second footplate 1722 to disengage from the second body portion 1730. In this way, the second body portion 1730 may be considered a second coupler for coupling the second footplate 1722 to the distractor 1714.

As best shown in FIG. 19D, the track 1738 extends distally through channel 1750 of the second body portion 1730. The track 1750 includes a plurality of grooves that are configured to be engaged by an activation worm such that when the activation worm is rotated, the second body portion 1730 translates distally. The track 1738 further includes a plurality of teeth on disposed on side surfaces of the track that are configured to be engaged by a pair of ratchet tabs extending from the second footplate 1718 to thereby prevent reverse sliding of the movable footplate.

Figure 19C:
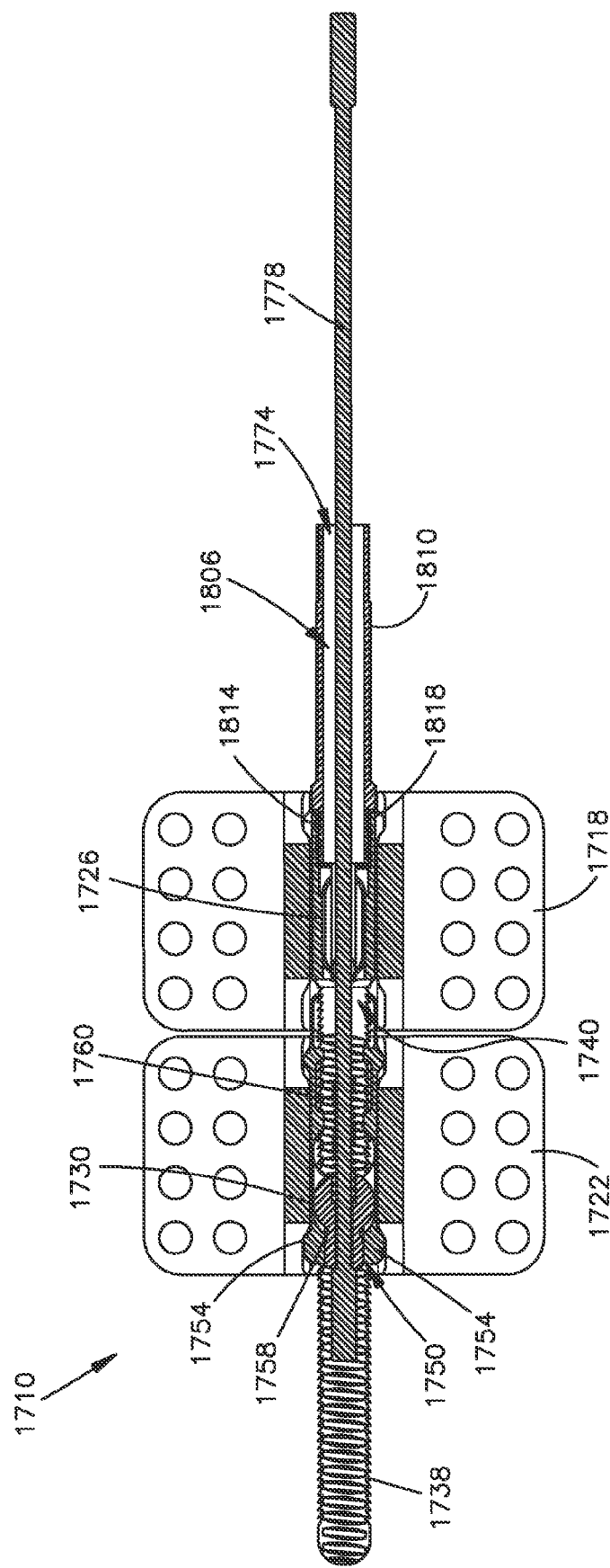
FIG. 19C is a cross-sectional view of the distractor assembly shown in FIG. 19B through the line 19C-19C.
Figure 19E:
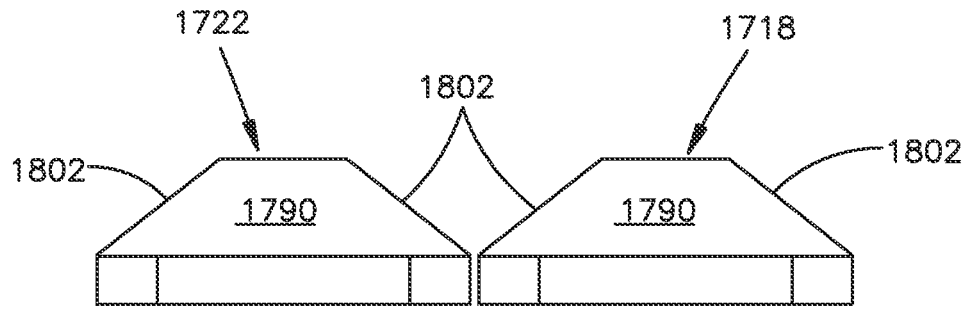
FIG. 19E is a side elevational view of the first and second footplates of the distractor assembly shown in FIG. 19A.

As shown in FIGS. 19A-19D, the distractor 1714 further includes an activation mechanism 1766 having an activation extension 1768 and an activation worm 1770 that extends distally from the activation extension 1768. As shown, the activation mechanism 1766 or at least the activation worm 1770 extends through the channel 1740 of the first body portion 1726 and into the channel 1750 of the second body portion 1730. As shown in FIG. 19D the activation worm 1770 includes external threads that engage the grooves of the track 1738. Both the activation extension 1768 and the activation worm 1770 define a bore 1774 that extends longitudinally therethrough. The bore 1774 is configured to receive a removal actuator 1778 that extends completely through the activation mechanism 1766, through the lock component 1758 and out a distal end of the second body portion 1730. The actuator 1778 is configured to disengage the first and second footplates 1718, 1722 from the first and second body portions 1726, 1730, when the actuator 1778 is pulled.

Figure 19F:
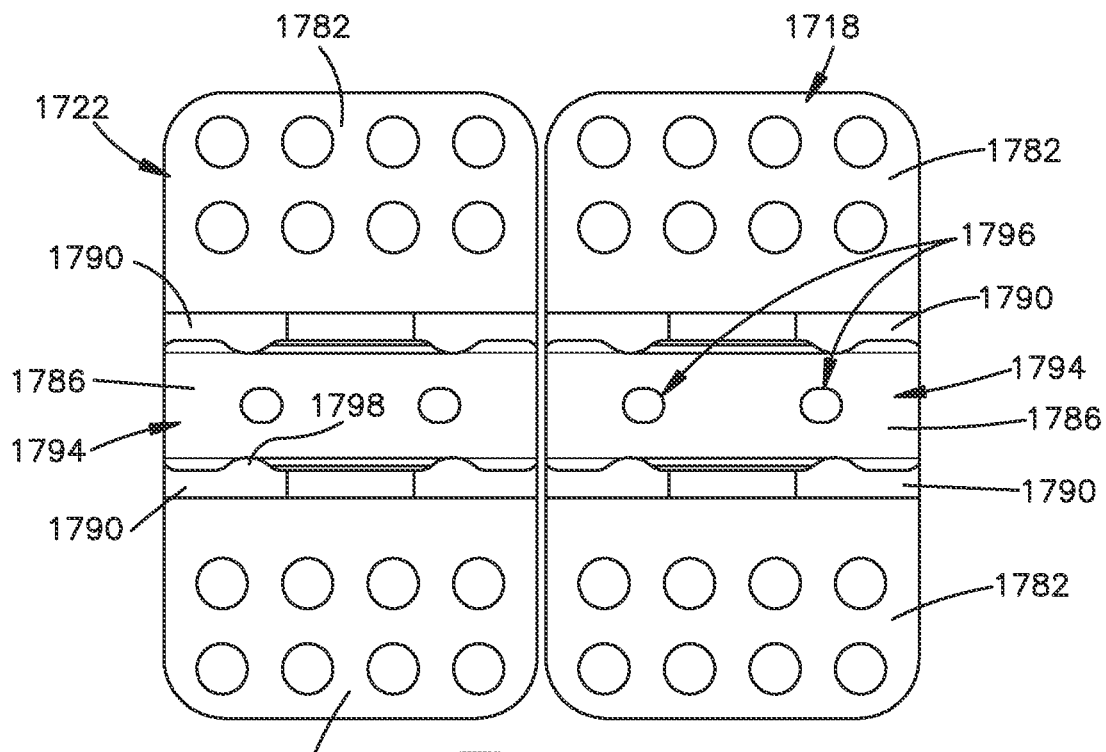
FIG. 19F is a top plan view of the first and second footplates shown in FIG. 19E.
Figure 19G:
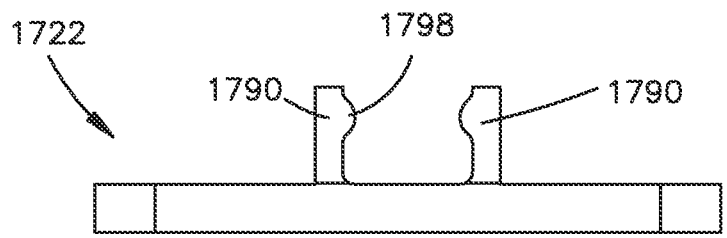
FIG. 19G is a front elevational view of the first and second footplates shown in FIG. 19E.

As shown in FIGS. 19F-19H, the first and second footplates 1718, 1722 each include a pair of wings 1782 separated by a central bridge portion 1786. Each central bridge portion 1786 includes a pair of longitudinally extending walls 1790 that define a channel 1794 configured to receive a respective body portion 1726, 1730. The central bridge portion 1786 of at least the first footplate 1718 defines a recess 1796 within the channel 1794 that is configured to receive the ball detent 1742 of the of first body portion 1726 to thereby hold the first footplate 1718 to the first body portion 1726. The walls 1790 of the first and second footplates 1718, 1722 include engagement features 1798 that are configured to engage the grooves 1742 of the first and second body portions 1726, 1730 to thereby retain the distractor 1714. The spring fingers 1754 of the second body portion 1730 sit outside the second footplate 1722 and prevent the distractor 1714 from being removed.

The walls 1790 of the first and second footplates 1718, 1722 include distal and proximal sides 1802 that are angled. The angled sides 1802 of the first footplate 1718 allow the second body portion 1730 to easily ride over the first footplate 1718 during removal of the distractor 1714.

To lock the first footplate 1718 to the first body portion 1726, the distractor assembly 1710 includes a locking mechanism 1806 that defines a sleeve 1810 that is disposed about the activation extension 1768 and coupled to the first body portion 1726. In particular, the sleeve 1810 includes external threads 1814 that engage internal threads 1818 of the first body portion 1726. When engaged, the ball detent 1742 of the first body portion 1726 is prevented from disengaging from the recess 1796 of the first footplate 1718 thereby locking the first footplate 1718 to the first body portion 1726. It should be understood that the sleeve 1810 may be considered an oversized tube.

To remove the distractor 1714 and leave the footplates 1718, 1722 behind, the sleeve 1810 is disengaged or otherwise removed from the first body portion 1726 thereby allowing the ball detent 1742 to disengage from the recess 1796. Once the sleeve is disengaged, the actuator 1778 is pulled which in turn pulls the lock component 1758 proximally to thereby allow the fingers 1754 to disengage from the second footplate 1730. At this point the first and second footplates 1718, 1722 are released from the distractor 1714 and further pulling of the actuator 1778 pulls the distractor 1714 out of the patient while the first and second footplates 1718, 1722 remain behind. Because the second body portion 1730 can not be pulled through the first footplate 1718, the second body portion 1730 rides up the angled sides 1802 of the first footplate's central bridge portion 1786 as it is pulled proximally.

Figure 20A:
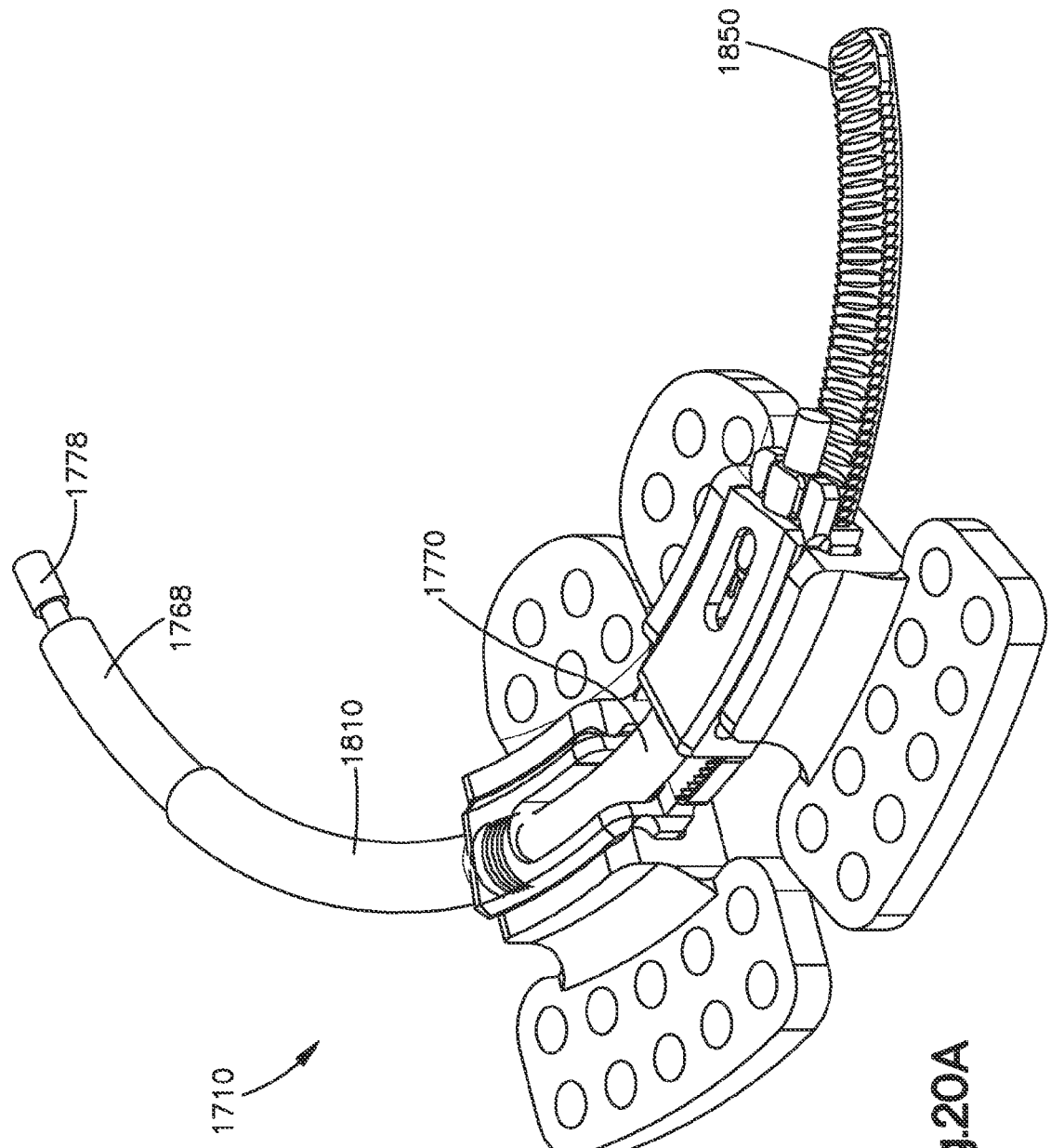
FIG. 20A is a perspective view of the distractor assembly shown in FIG. 19A including a distractor having a curved track.

As shown in FIGS. 20A and 20B the distractor assembly 1710 may include a curved track 1850 that is curved along a specific radius, such as a predetermined radius. In this embodiment, the activation extension 1768, the activation worm 1770, the actuator 1778, and the sleeve 1810 are made of a flexible material, or of a rigid material that is laser cut to be flexible.

In another embodiment and in reference to FIGS. 21A-21I, the distractor assembly may include other configurations that release the footplates from the distractor when a tube is removed. As shown, a distractor assembly 1910 includes a distractor 1914, a first footplate 1918 releasably attached to the distractor 1914, and a second footplate 1922 releasably attached to the distractor distal to the first footplate 1918. In the illustrated embodiment, the first footplate 1918 is configured to translate relative to the second footplate 1922.

As best shown in FIGS. 21A-21I, the distractor 1914 includes a first body portion 1950 that is configured to releasably hold the first footplate 1918 and a second body portion 1954 that is distal to the first body portion 1950 and configured to releasably hold the second footplate 1922. As shown, the first body portion 1950 is elongate in the longitudinal direction L and includes an elongate channel 1958 that extends through the first body portion 1950 in the longitudinal direction L.

An upper wall of the channel 1958 defines a spring finger 1972 that is configured to engage the first footplate 1918 to thereby couple the first footplate 1918 to the first body portion 1950. As best shown in FIG. 21C, the spring finger 1972 includes an upward extending protrusion 1976 at its end. That is, the finger 1972 includes a protrusion 1976 that extends vertically away from the central axis of the distractor 1914. The finger 1972 is configured to spring out and engage the first footplate 1918 to thereby couple the first footplate 1918 to the first body portion 1950. In this way, the first body portion 1950 may be considered a first coupler for coupling the first footplate 1918 to the distractor 1914.

As shown in FIGS. 21H and 21I, a proximal portion of the first body portion 1950 defines lateral ratchet tabs 1979 that are configured to engage teeth defined by an activation track. The ratchet tabs 1979 prevent reverse sliding of the first footplate 1918. The proximal portion of the first body portion 1950 also includes a release clip 1980 that forces the ratchet tabs 1979 outward during removal of the distractor 1914.

The second body portion 1954 is also elongate in the longitudinal direction L and includes a holding portion 1982 and an activation track 1986 that extends proximally from the holding portion 1982. The holding portion 1982 includes an elongate channel 1998 that extends through the holding portion 1982 in the longitudinal direction L. The channel 1998 of the second body portion 1954 is aligned with the channel 1958 of the first body portion 1950. An upper wall of the channel 1998 defines a spring finger 2002 having an upward extending protrusion 2006 at its end. That is, the finger 2002 includes a protrusion 2006 that extends vertically away from the central axis of the distractor 1914. The finger 2002 is configured to spring out and engage the second footplate 1922 to thereby couple the second footplate 1922 to the second body portion 1954. In this way, the second body portion 1954 may be considered a second coupler for coupling the second footplate 1922 to the distractor 1914

The activation track 1986 of the second body portion 1954 extends out from the holding portion 1982 and is configured to extend through a channel defined by a lower portion of the first footplate's central bridge portion. As shown in FIG. 21C, the activation track 1986 defines a plurality of grooves 2010 that are exposed to the channel 1958 of the first body portion 1950. The grooves 2010 are disposed along the longitudinal length of the activation track 1986 and are configured to be engaged by external threads defined by the activation mechanism.

Figure 21A:
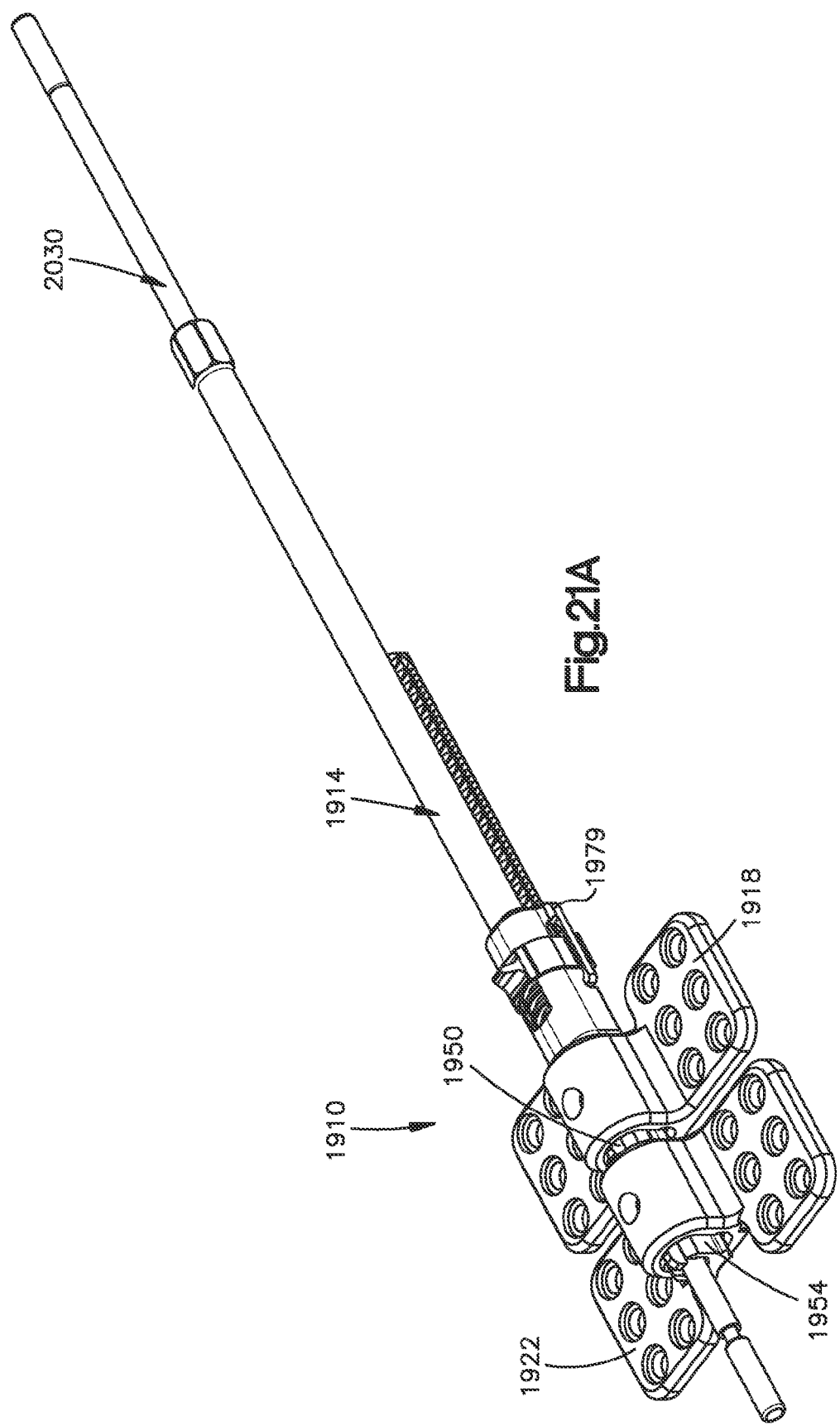
FIG. 21A is a perspective view of a distractor assembly according to another embodiment. The assembly including a distractor and first and second footplates releasably coupled to the distractor with a locking mechanism having a tube that when removed releases the footplates from the distractor.

As shown in FIGS. 21A-21I, the distractor 1914 further includes an activation mechanism 2014 having an activation extension 2018, and an activation worm 2022 that extends distally from the activation extension 2018. Both the activation extension 2018 and the activation worm 2022 define a longitudinally elongate bore 2024 that extend therethrough. As shown in FIG. 21C, the activation worm 2022 extends into the channel 1958 of the first body portion 1950 and engages the grooves 2010 defined on the activation track 1986. In particular, the activation worm 2022 includes threads 2026 that engage the grooves 2010 of the track such that rotation of the activation worm 2022 causes the first body portion 1950 and thus the first footplate 1918 to translate proximally.

As shown in FIG. 21C the distractor assembly 1910 further includes a locking mechanism 2030 that extends through the bore 2024 defined by the activation extension 2018, and activation worm 2022, through the channel 1998 of the second body portion 1954, and out the distal end of the distractor 1914. The locking mechanism 2030 includes a tube 2034 and a removal actuator 2038 that extends completely through the tube 2034. As shown, a distal end and a proximal end of the actuator 2038 includes a widened portion 2042. The widened portions 2042 may be ferrules that are crimped onto the actuator. To remove the tube 2034 from the actuator 2038, the proximal ferrule 2042 is cut off, to thereby allow the tube 2034 to be pulled proximally.

As shown in FIGS. 21F-21I, the first and second footplates 1918, 1922 each include a central bridge portion 2042 and wings 2046 that extend laterally out from the bridge portion 2042. Each central bridge portion 2042 includes a body 2050 that defines a longitudinally extending channel 2054. The channels 2054 are configured to receive the first and second body portions 1950, 1954 of the distractor 1914. As shown in FIG. 21I a lower portion of the first footplate's channel 2054 is substantially rectangular and is configured to receive the activation track 1986 that extends from the second body portion 1954. This arrangement allows the first body portion 1950 to translate along the track 1986 along a predetermined line.

To release the footplates 1918, 1922 from the distractor 1914 the tube 2034 of the locking mechanism 2030 is removed to thereby allow the spring fingers of the first and second body portions 1950, 1954 to flex. When the actuator 2038 is pulled proximally, the distractor 1914 will be pulled proximally along with the actuator 2038 leaving the footplates 1918, 1922 behind.

In another embodiment and in reference to FIGS. 22A-22H the distractor assembly may include a locking component that locks the distractor to the footplates. As shown, a distractor assembly 2110 includes a distractor 2114, a first footplate 2118 releasably coupled to the distractor 2114, and a second footplate 2122 coupled to the first footplate 2118. In the embodiment illustrated, the first footplate 2118 is configured to translate relative to the second footplate 2122.

As shown in FIGS. 22B-22D, the distractor 2114 includes a coupler 2126 that is releasably coupled to the first footplate 2118. The coupler 2126 includes a body 2130 that defines a T-slot 2134 along its bottom surface. The T-slot 2134 is defined by two downward extending walls 2138, each wall 2138 having a laterally inward extending flange 2142. The T-slot 2134 is configured to receive and hold a portion of the first footplate 2118. An upper portion of the coupler 2126 includes a longitudinally extending bore 2146. Below the bore 2146 is a clip 2150 that extends proximally and is configured to clip onto an activation mechanism.

In this regard, the distractor 2114 further includes an activation mechanism 2160 that is configured to drive the first footplate 2118 relative to the second footplate 2122. As shown, the activation mechanism 2160 includes an activation extension 2164 and an activation worm 2168 that extends distally from the activation extension 2164. The worm 2168 includes external threads that are configured to engage a track that extends from the second footplate. As shown in FIG. 21A, the clip 2150 of the coupler 2126 engages the activation worm 2168 when the activation worm 2168 is fully inserted. This firmly secures the activation mechanism 2160 to the coupler 2126. This also prevents inadvertent rotation under no load.

Figure 22H:
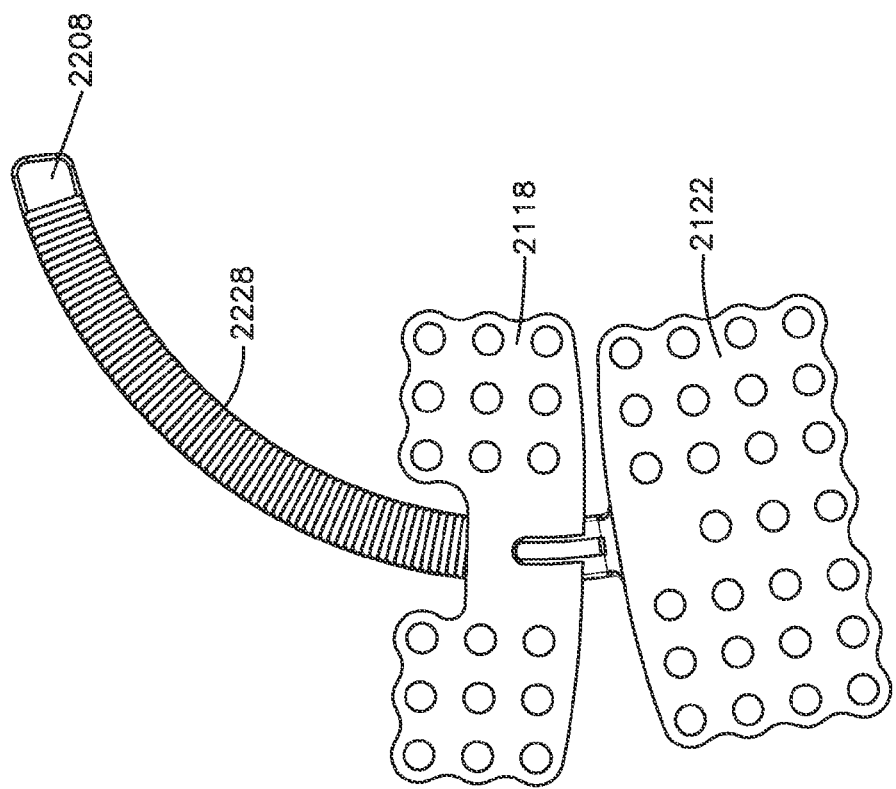
FIG. 22H is a bottom plan view of the first and second footplates shown in FIG. 22G.
Figure 22G:
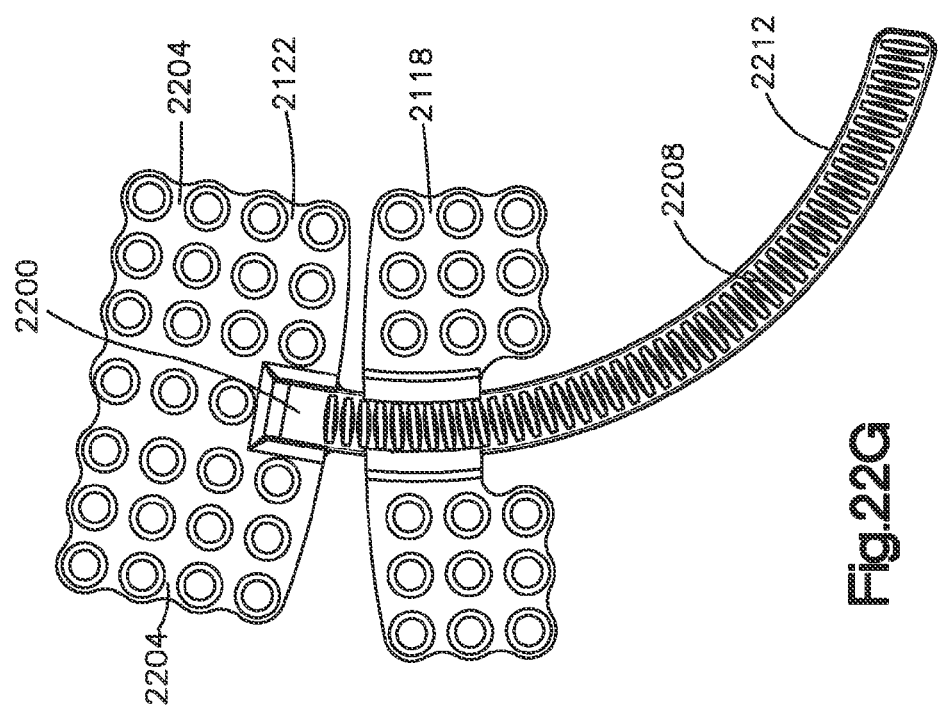
FIG. 22G is a top plan view of the first and second footplates of the distractor assembly shown in FIG. 22A.

As shown in FIGS. 22C, 22G, and 22H, the first footplate 2118 includes a central bridge portion 2170 and a wing 2174 that extends laterally out from each side of the central bridge portion 2170. As shown, the central bridge portion 2170 includes a body 2178 that defines a channel 2182 that extends therethrough. An upper wall of the channel 2182 defines a slot 2186 that extends along the entire length of the upper wall. A lower wall of the channel 2182 defines a ratchet tab 2190. The body 2178 further defines opposing longitudinally elongate slots 2194 that are configured to be engaged by the flanges 2142 of the coupler 2126.

The second footplate 2122 includes a central bridge portion 2200 and a wing 2204 that extends laterally out from opposing sides of the central bridge portion 2200. As shown, the central bridge portion 2200 includes a track 2208 that extends distally through the channel 2182 of the first footplate 2118. In the illustrated embodiment the track 2208 is curved along a predetermined arc. As shown the track 2208 includes grooves 2212 that are configured to be engaged by the activation worm 2168 such that rotation of the worm 2168 causes the first footplate 2118 to translate along the track 2208. A bottom surface of the track 2208 includes engagement features such as teeth 2228 that are configured to be engaged by the ratchet tab 2190 of the first footplate 2118 to prevent reverse sliding of the first footplate 2118 after distraction.

To lock the distractor 2114 to the first footplate 2118, the distractor assembly 2110 includes a locking mechanism 2234. The locking mechanism 2234 includes a sleeve 2238 that is disposed about the activation extension 2164 and defines external threads 2250. The locking mechanism 2234 further includes a nut 2254 having internal threads 2258 that engage the external threads 2250 of the sleeve 2238. Extending distally from the nut 2254 is a locking component 2262 that is configured to engage and lock the first footplate 2118 to the coupler 2126. In the illustrated embodiment, the lock component 2262 includes a shaft 2266 that extends distally from the nut 2254 and through the bore 2146 of the coupler 2126. Extending distally from the shaft 2266 is an engagement feature 2270 that defines a plate 2274 that is configured to engage the channel 2182 of the first footplate 2118 and force the first footplate 2118 against the coupler 2126 to thereby lock the first footplate 2118 to the coupler 2126.

In operation, the locking mechanism 2234 may be in a first position in which the engagement feature 2270 is locking the first footplate 2118 to the coupler 2126 as shown in FIG. 22E. To release the first footplate 2118 from the coupler 2126, the sleeve 2238 is rotated thereby causing the nut 2254 to translate distally. As the nut 2254 translates the engagement feature 2270 is also translated distally and disengages from the coupler 2126, as shown in FIG. 22F. At this point the footplates 2118, 2122 are released from the distractor 2114 and the distractor 2114 may be removed while the footplates 2118, 2122 remain behind.

The present inventions are illustrated by the description of several embodiments. The present invention, however, is not limited to the particular embodiments described herein. Rather the present invention encompasses any combination of the features of any of the embodiments and natural variations thereof, as will be understood by persons having ordinary skill in the art. Further while certain features are described as being first and second, it should be understood that either of the features may be considered first or second. For example, while the footplates are described as first and second footplates having different features, it should be understood that either footplate could be considered the first footplate or second footplate. Further, while the distractors have been described as forcing bone segments away from each other, it should be understood that the distractor disclosed may also be configured for reduction (i.e. forcing the bone segments toward each other).

What is claimed is:

1. A bone distractor assembly configured to distract first and second bone segments that are separated by a bone gap, the distractor assembly comprising:
   a first footplate defining a channel and including a ratchet tab;
   a second footplate including an extension that carries a track, the track configured to be received in the channel and defining a plurality of grooves configured to receive the ratchet tab; and
   a distractor defining external threads configured to engage internal threads defined by the first footplate such that the distractor is releasably coupled to the first footplate, the distractor having a distal end portion that includes an activation screw and is configured to engage the second footplate, such that rotation of the activation screw causes the second footplate to translate relative to the first footplate.

2. The distractor assembly of claim 1, wherein the activation screw defines a conical head having external threads.

3. The distractor assembly of claim 1, wherein the distractor includes a sleeve having a distal coupling portion configured to releasably lock the activation screw to the first footplate, the distractor further includes a body disposed within the sleeve, the body being coupled to the activation crew, and the distal coupling portion of the sleeve defines external threads that are configured to engage internal threads defined by the first footplate to thereby releasably lock the activation screw to the first footplate.

4. The distractor assembly of claim 1, wherein the first and second footplates are resorbable.

5. The distractor assembly of claim 1, wherein the distractor includes a coupling member at its proximal end and the activation screw at its distal end.

6. The distractor assembly of claim 5, wherein rotation of the coupling member causes rotation of the activation screw.

7. The distractor assembly of claim 1, wherein the distractor is releasably coupled to the second footplate.

8. The distractor assembly of claim 1, wherein first footplate includes a central bridge portion and a pair of wings extending laterally out from the central bridge portion, the pair of wings defining a plurality of holes configured to secure the pair of wings to bone.

9. The distractor assembly of claim 8, wherein the central bridge portion defines the channel.

10. The distractor assembly of claim 8, wherein the central bridge portion defines a second channel configured to receive the distractor.

11. The distractor assembly of claim 8, wherein the central bridge portion defines the ratchet tab, and the ratchet tab is configured to prevent reverse sliding once the second footplate is translated relative to the first footplate.

12. A bone distractor assembly configured to distract first and second bone segments that are separated by a bone gap, the distractor assembly comprising:
    a first footplate defining a channel and including a ratchet tab;
    a second footplate including an extension that carries a track, the track configured to be received in the channel and defining a plurality of grooves configured to receive the ratchet tab; and
    a distractor releasably coupled to the first footplate, the distractor having a proximal end and a distal end spaced from the proximal end, the distal end including an activation screw and configured to engage the second footplate, such that rotation of the activation screw causes the second footplate to translate relative to the first footplate,
        wherein the extension extends from the second footplate in a proximal direction towards the proximal end of the distractor when the track is received in the channel and the distractor is coupled to the first footplate.

13. The bone distractor assembly of claim 12, wherein the extension is configured to extend through the channel towards the proximal end of the distractor.

14. The bone distractor assembly of claim 12, wherein first footplate includes a central bridge portion and a pair of wings extending laterally out from the central bridge portion, the pair of wings defining a plurality of holes configured to secure the pair of wings to bone.

* * * * *